(12) United States Patent
Palmenberg et al.

(10) Patent No.: US 11,667,690 B2
(45) Date of Patent: Jun. 6, 2023

(54) RECOMBINANT CDHR3 PROTEIN FRAGMENTS INHIBIT RHINOVIRUS C BINDING AND REPLICATION

(71) Applicant: Wisconsin Alumni Research Foundation, Madison, WI (US)

(72) Inventors: Ann Carol Palmenberg, Madison, WI (US); Kelly Watters, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/058,934

(22) PCT Filed: May 30, 2019

(86) PCT No.: PCT/US2019/034580
§ 371 (c)(1),
(2) Date: Nov. 25, 2020

(87) PCT Pub. No.: WO2019/232164
PCT Pub. Date: Dec. 5, 2019

(65) Prior Publication Data
US 2021/0214413 A1 Jul. 15, 2021

Related U.S. Application Data

(60) Provisional application No. 62/768,191, filed on Nov. 16, 2018, provisional application No. 62/678,507, filed on May 31, 2018.

(51) Int. Cl.
| | | |
|---|---|---|
| *C07K 14/705* | (2006.01) | |
| *G01N 33/50* | (2006.01) | |
| *A61K 38/00* | (2006.01) | |
| *G01N 33/569* | (2006.01) | |

(52) U.S. Cl.
CPC ..... *C07K 14/705* (2013.01); *G01N 33/56983* (2013.01); *A61K 38/00* (2013.01)

(58) Field of Classification Search
CPC . C07K 14/705; G01N 33/56983; A61K 38/00
See application file for complete search history.

(56) References Cited

U.S. PATENT DOCUMENTS

| | | | | |
|---|---|---|---|---|
| 9,938,507 B2 * | 4/2018 | Gern | ........................ | C12N 7/00 |
| 10,280,405 B2 * | 5/2019 | Gern | ........................ | C12N 7/00 |
| 2002/0042386 A1 * | 4/2002 | Rosen | .................... | C07K 14/47 |
| | | | | 435/325 |
| 2017/0082609 A1 * | 3/2017 | Gern | .................. | G01N 33/5014 |

FOREIGN PATENT DOCUMENTS

WO 2002044340 A2 6/2002

OTHER PUBLICATIONS

Watters et al., 2018, CDHR3 extracellular domains EC1-3 mediate rhinovirus C interaction with cells and as recombinant derivatives, are inhibitory to virus infection, PLoS Pathogens, 14(12): e1007477 (21 pages).*
Perez, T. D., et al. "Cadherin adhesion: mechanisms and molecular interactions." Cell adhesion. Springer, Berlin, Heidelberg, 2004. 3-21.
Plummer Thj, et al. (1984) Demonstration of peptide:N-glycosidase F activity in endo-beta-N-acetylglucosaminidase F preparations. J Biol Chem 259: 10700-10704.
Pokutta, S., et al., Conformational changes of the recombinant extracellular domain of E-cadherin upon calcium binding. Eur J Biochem, 1994. 223: p. 1019-1026.
Quist AP, et al. (2000) Physiological role of gap-junctional hemichannels. Extracellular calcium-dependent isosmotic volume regulation. J Cel Biol 148: 1063-1074.
Shapiro L, et al. "Structure and biochemistry of cadherins and catenins." Cold Spring Harbor perspectives in biology 1.3 (2009): a003053.
Shapiro L., et al., Structural basis of cell-cell adhesion by cadherins. Nature, 1995. 374: p. 327-337.
Sheehy AM, et al. (2002) Isolation of a human gene that inhibits HIV-1 infection as is supressed by the viral Vif protein. Nature 418: 646-650.
Sherer, N.M., et al., Visualization of retroviral replication in living cells reveals budding into multivesicular bodies. Traffic., 2003. 4: p. 785-801.
Suzuki, Y., Sialobiology of influenza molecular mechanisms of host range variation of influenza viruses. Biological and Pharmaceutical Bulletin, 2004. 28: p. 399-408.
Froyanovsky, R.B., et al., Adhesisve and lateral E-cadherin dimers are mediated by the same interface. Mol and Dell Biol., 2003. 23: p. 7965-7972.
Turunen R, et al. (2016) Rhinovirus species and clinical characteristics in the first wheezing episode in children. J Med Virol 88: 2059-2068.
Wheelock MJ, et al. (2003) Cadherin-mediated cellular signaling. Curr Op Cell Biol 15: 509-514.
Yanai I, et al. (2005) Genome-wide midrange transcription profiles reveal expression level relationships in human tissue specification. Bioinformatics 21: 650-659.
Anonymous. CR201_G0018053—CDHR3 isoform 7—Pongo abelii (Sumatran orangutan)—CR201_GO018053 genen & protein, Mar. 28, 2018, XP055612503, retrieved from the Internet: URL:https://www.uniprot.org/uniprot/A0A2J8VKW9 [retrieved on Aug. 13, 2019].
Aricescu AR, et al. (2006) A time- and cost-efficient system for high-level protein production in mammalian cells. Acta Crystallogr D Biol Crystallogr 62: 1243-1250.

(Continued)

*Primary Examiner* — Amber D Steele
(74) *Attorney, Agent, or Firm* — Quarles & Brady, LLP

(57) ABSTRACT

The present invention provides soluble truncated peptides of CDHR3, recombinant variants thereof and methods of making these peptides. The present invention also provide methods of inhibiting rhinovirus C infection and an in vitro assay for screening for anti-viral agents against rhinovirus C.

18 Claims, 11 Drawing Sheets

Specification includes a Sequence Listing.

(56) References Cited

OTHER PUBLICATIONS

Ashraf S, et al (2013) Biological characteristics and propagation of human rhinovirus-C in differentiated sinus epithelial cells. Virology 436: 143-149.
Bizzintino J, et al. (2011) Association between human rhinovirus C and severity of acute asthma in children. Eur Respir J 37: 1037-1042.
Bochkov YA, et al. (2011) Molecular modeling, organ culture and reverse genetics for a newly identified human rhinovirus C. Nature Medicine 17: 627-632.
Bochkov YA, et al. (2015) Cadherin-related family member 3, a childhood asthma susceptibility gene product, mediates rhinovirus C binding and replication. Proc Natl Acad Sci USA 112: 5485-5490.
Bochkov YA, et al., Mutations in VP1 and 3A proteins improve binding and replication of rhinovirus C15 in HeLa-E8 cells. Virology, 2016. 499: p. 350-360.
Boggon, T.J., et al., C-cadherin ectodomain structure and implications for cell adhesion mechanisms. Science, 2002. 296: p. 1308-1313.
Bonnelykke K, et al. (2014) A genome-wide association study identifies CDHR3 as a susceptibility locus for early childhood asthma with severe exacerbations. Nature Genetics 46: 51-55.
Bonnelykke, K., et al. "Cadherin-related family member 3 genetics and rhinovirus C respiratory illnesses." American journal of respiratory and critical care medicine 197.5 (2018): 589-594.
Chen, X. et al., Advances in the biology and chemistry of sialic acids. ACS Chemical Biology, 2011. 5: p. 163-176.
Cox DW, et al. (2013) Human rhinovirus species C infection in young children with acute wheeze is associated with increased acute repiratory hospital admissions. Am J Respir Crit Care Med 188: 1358-1364.
Database Geneseq. "Human extracellular matrix protein from gene 18." Dec. 18, 2003. XP002793520, retrieved from EBI accession No. GSP:ADC10825 Database accession No. ADC10825.
Database Geneseq. "Human novel polypeptide #69." Aug. 30, 2002. XP002793521, retrieved from EBI accession No. GSP:ABG66734 Database accession No. ABG66734.
Dominguez Sr, et al. (2008) Multiplex MassTag PCR for respiratory pathogens in pediatric nasopharyngeal washes by conventional diagnostic testing shows a high prevalence of viruses belonging to a newly recognized rhinovirus clade. J Clin Virol 43: 219-222.
Gallois-Montbrun S, et al. (2007) Antiviral protein APO-BEC3G localizes to ribonucleoprotein complexes found in P bodies and stress granules. J Virol 81: 2165-2178.
Dern JE (2010) The ABCs of rhinoviruses, wheezing, and asthma. J Virol 84: 7418-7426.
Greve JM, et al. (1989) The major human rhinovirus receptor is ICAM-1. Cell 56: 839-847.
Greve JM, et al. Mechanisms of receptor-mediated rhinovirus neutralization defined by two soluble forms of ICAM-1. J Virol, 1991. 65: p. 6015-6023.
Griggs TF, et al. (2015) Production, purification, and capsid stability of rhinovirus C types. J Virol Methods 217: 18-23.
Griggs TF, et al. (2017) Rhinovirus C targets ciliated airway epithelial cells. Respiratory Research 18: 84.
Guo, H., et al., Regulation of homotypic cell-cell adhesion by branched N-glycosylation of N-cadherin extracellular EC2 and EC3 domains. J Biol Chem, 2009. 284: p. 34986-34997.
Halbleib JM, et al. (2006) Cadherins in development: cell adhesion, sorting, and tissue morphogenesis. Genes and Dev 20: 3199-3214.
Hao W, et al. (2012) Infection and propagation of human rhino-virus C in human airway epilethial cells. J Virol 86: 24-32.
Harrison, O.J., et al., The extracellular architecture of adherens junctions revealed by crystal structures of type I cadherins. Struct., 2011. 19: p. 244-256.

Haussinger, D., et al., Calcium-dependent homoassociation of Eclient cadherin by NMR Spectroscopy: changes in mobility, conformation and mapping of contact regions. J Mol Biol, 2002. 324: p. 823-839.
Hofer F, et al. (1994) Members of the low density lipoprotein receptor family mediate cell entry of a minor-group common cold virus. Proc Natl Acad Sci U S A 91: 1839-1842.
International Searching Authority. International Search Report and Written Opinion for application PCT/US2019/034580. dated Sep. 6, 2019. 16 pages.
Jartti T, et al. (2009) Bronchiolitis: age and previous wheezing episodes are linked to viral etiology and atopic characteristics. Pediatr Infect Dis J 28: 311-317.
Juven T, et al. (2000) Etiology of community-acquired pneumonia in 254 hospitalized children. Pediatr Infect Dis J 19:293-298.
Kartenbeck J, et al. (1991) Endocytosis of junctional cadherins in bovine kidney epithelial (MDBK) cells cultured in low Ca2+ ion medium. J Cel Biol 113: 881-892.
Kim D, et al. (2004) Protein structure prediction and analysis using the Robetta server. Nucleic Acid Res 32: 526-531.
Koch, A.W., et al., Calcium binding and homoassociation of E-cadherin domains. Biochemistry, 1997. 36: p. 7697-7705.
Langer, M.D., et al., N-glycosylation alters cadherin-mediated intercellular binding kinetics. J Cell Sci, 2012. 125: p. 2478-2485.
Last-Barney, K., et al., Detection of major group rhinoviruses by soluble intercellular adhesion molecule-1 (slCAM-1). Jornal of Virological Methods, 1991. 35: p. 255-264.
Lee W-M, et al. (2012) Human rhinovirus species and season of infection determine illness severity. Am J Respir Crit Care Med 186: 886-891.
Liu, Y., et al. (2015) Sialic acid-dependent cell entry of human enterovirus D68. Nature Communications.
Liu, Y., et al., Atomic structure of a rhinovirus C, a virus species linked to severe childhood asthma. Proc. Nat. Acad. Sci. USA, 2016. 113: p. 8997-9002.
Liu, Y., et al., Structure and inhibition of EV-D68, a virus that causes respiratory illness in children. Science, 2015. 347: p. 71-74.
Liwosz A, et al. (2006) N-glycosylation affects the molecular organization and stability of E-cadherin junctions. J Biol Chem 281: 23138-23149.
Marlovits, T.C., et al., Very-low-density lipoprotein receptor fragment shed from HeLa cells inhibits human rhinovirus infection. J Virol, 1998. 72: p. 10246-10250.
Mattey DL, et al. (1986) Splitting and internalization of the desmosomes of cultured kidney epithelial cells by reduction in calcium concentration. J Cell Sci 85: 113-124.
McErlean P, et al. (2007) Characterisation of a newly identified human rhinovirus, HRV-QPM, discovered in infants with bronchiolitis. J Clin Virol 39: 67-75.
Nagar, B., et al., Structural basis of calcium-induced E-cadherin rigidification and dimerization. Nature, 1996. 380: p. 360-364.
Nakagome, K., et al., Effects of rhinovirus species on viral replication and cytokine production. J Allergy Clin Immunol, 2014. 134: p. 332-341.
Nejsum LN, et al. (2007) A molecular mechanism directly linking E-cadherin adhesion to initiation of epithelial cell surface polarity. J Cel Biol 178: 323-335.
Niessen, C.M., et al., Tissue organization by cadherin adhesion molecules: Dynamic molecular and cellular mechanisms of morphogenetic regulation. Physiol Rev., 2011. 91: p. 691-731.
O'Doherty U, et al (2000) Human immunodeficiency virus type 1 spinoculation enhances infection through virus binding. J Virol 74: 10074-10080.
D'Neill MB, et al. (2017) Evolutionary genetics of a disease susceptibility locus in CDHR3. bioRxiv http://dx.doi.org/10.1101/186031.
Palmenberg, A.C., Rhinovirus C, asthma, and cell surface expression of virus receptor, CDHR3. J Virol, 2017. 91.

* cited by examiner

RECOMBINANT CDHR3 PROTEIN FRAGMENTS INHIBIT RHINOVIRUS C BINDING AND REPLICATION

CROSS-REFERENCE TO RELATED APPLICATIONS

This application is a national stage filing under 35 U.S.C. § 371 of International Patent Application No. PCT/US2019/034580, filed May 30, 2019, which claims priority to U.S. Provisional Application No. 62/678,507 filed on May 31, 2018 and U.S. Provisional Application 62/768,191 filed on Nov. 16, 2018, the contents of which are incorporated by reference in their entireties.

STATEMENT REGARDING FEDERALLY SPONSORED RESEARCH

This invention was made with government support under AI104317 awarded by the National Institutes of Health. The government has certain rights in the invention.

SEQUENCE LISTING

A Sequence Listing accompanies this application and is submitted as a txt file named "960296.04080_ST25_Replacement Listing.txt" which is 52,341 bytes in size and was created on Sep. 2, 2022. The sequence listing is electronically submitted and is incorporated herein by reference in its entirety.

BACKGROUND OF THE INVENTION

Rhinoviruses (RV) are a large group of non-enveloped, single-stranded, positive-sense RNA viruses in the Enterovirus genus of the Picornaviridae family. More than 160 types of rhinoviruses (RVs) are known. RVs are currently classified into three species (A, B and C) of Enteroviruses in the family Picornaviridae. RV-A and RV-B have been known for many years, but the discovery of RV-C in 2006 surprised the molecular and clinical virology communities.

The RV-C are clearly rhinoviruses, but unlike RV-A or RV-B, they are not readily propagated in typical cell culture systems. For example, conventional cell lines such as NCI-H358, WI-38, WisL, HEK293T, BEAS-2B, A549 and HeLa, do not support any detectable RV-C replication. The RV-C are not "new" in terms of evolution, but rather they were physically undetected by typical characterization methods that required cultured virus growth and induction of cytopathic effects, such as endpoint dilution (TCID50) or plaque assays. Initially, virus propagation was restricted to sinus mucosa organ tissues or to airway epithelial air-liquid-interface cultures (ALI) because the isolates proved refractive to standard cell culture [11,12]. These labor-intensive, low virus-titer systems did allow the determination that RV-C growth required a cellular receptor component distinct from intercellular adhesion molecule 1 (ICAM-1) or the low-density lipoprotein receptor (LDLR) used by the RV-A/B species [10,13,14].

Collectively, RV are the primary etiological agents of upper respiratory tract common colds, but many also induce more severe lower respiratory tract illnesses, including bronchitis and pneumonia [1-3]. Rhinovirus (RV)-C viruses (55 types), together with RV-A and RV-B viruses (100 types), are the leading cause of common colds. However, the RV-C lead to more severe respiratory infections among children than any other known rhinoviruses and it is now recognized these strains are associated with up to half of rhinovirus illnesses in young children.

In contrast to other RV, the RV-C utilize cadherin related family member 3 (CDHR3) as a cellular receptor. This childhood asthma susceptibility gene product is expressed in the human lower respiratory tract. In line with this etiology, RV-Cs cause a significantly higher rate of lower respiratory tract infections in children than in adults and are directly associated with childhood asthma exacerbations. Similar to influenza, RV-C infections peak in winter months. Currently, there are no vaccines or effective antiviral treatments available.

CDHR3 belongs to the cadherin superfamily of transmembrane calcium-dependent adhesion proteins. The better-described classical cadherins are expressed in a variety of tissues, where they mediate cell-cell interactions, usually through homologous protein contacts, or where they participate in cell signaling, epithelial polarity, and tissue development and organization [16-19]. CDHR3 expression, in contrast, is generally restricted to airway tissues, with protein display primarily on the apical surfaces of ciliated epithelial cells [20,21]. The biological role of CDHR3 in lung development or function is unknown. Cadherins are Ca++-dependent cell adhesion proteins whose primary job is holding cells together through homologous contacts on or between cell surfaces. The sequence of human CDHR3 (885 amino acids) predicts a linear arrangement of 6 extracellular (EC) repeat domains (7 β-strands each) preceded by a signal sequence and tailed with a transmembrane domain (TM) linked to cytoplasmic recognition units. The role of these domains in viral entry and infectivity is not known.

Therefore, there is a need for understanding the virus receptor interactions in order to produce antivirals, including soluble receptors and in vitro assays for screening potential antiviral therapies.

SUMMARY OF THE INVENTION

The present invention overcomes the aforementioned drawbacks by providing soluble truncated CDHR3 peptides and methods of making and using for both therapies and in in vitro screening assays to detect antiviral agents.

In one aspect, the invention provides a soluble truncated CDHR3 peptide comprising (A) (a) domain 1 of CDHR3 (domain 1 of SEQ ID NO:1, e.g., SEQ ID NO:2), (b) domain 1 and domain 2 of CDHR3 (domain 1 and 2 of SEQ ID NO:1); (c) domain 1 and domain 3 of CDHR3 (domain 1 and 3 of SEQ ID NO:1) or (d) domains 1, 2 and 3 of CDHR3 (domain 1, 2 and 3 of SEQ ID NO:1), and (B) at least one linker, wherein the at least one linker is selected from linker 1, linker 2, linker 3 and linker 4.

In some aspects, the soluble truncated peptide further comprises at least one of the following: (i) linker 1 (SEQ ID NO:15) before domain 1, (ii) linker 2 (SEQ ID NO:16) between domain 1 and 2, (iii) linker 3 (SEQ ID NO:17) between domain 2 and 3 and (iv) linker 4 (SEQ ID NO:18) after domain 3.

In another aspect, the disclosure provides a soluble truncated CDHR3 peptide comprising: (a) domain 1 (SEQ ID NO:2) of CDHR3 or (b) domain 1 of CDHR3 with a mutation at position 76 relative to SEQ ID NO1 (SEQ ID NO:31), wherein X is selected from the amino acids consisting of A, G, V, L, I, S, and T, preferably A.

In some embodiments, the soluble truncated CDHR3 peptide further comprises at least one linker, wherein the at least one linker is linker 1 (SEQ ID NO:15) before domain 1, linker 2 (SEQ ID NO:16 after domain 1, or both.

In another aspect, the present disclosure provides a vector comprising the nucleic acids encoding a soluble truncated CDHR3 peptide described herein.

In yet another aspect, the disclosure provides a method of making the soluble truncated recombinant peptides, the method comprising: (a) transforming bacteria cells with the vector encoding a soluble truncated CDHR3 peptide described herein; (b) inducing recombinant protein expression in the bacteria cells; (c) lysing bacterial cells and collecting the inclusion bodies comprising the soluble truncated peptide by centrifugation; (d) solubilizing the protein within the inclusion body; and (e) dialyzing and refolding the protein in buffer supplemented with Ca++ to produce soluble truncated recombinant peptides of CDHR3.

In yet another aspect, the disclosure provides a therapeutic composition for reducing or preventing Rhinovirus C entry into cells, the composition comprising a soluble truncated peptide described herein and Ca++ in a pharmaceutically acceptable carrier.

In yet another aspect, the disclosure provides a method for reducing the infection by human rhinovirus (HRV) C of a host cell susceptible to infection by HRV-C, comprising: contacting the virus with the soluble truncated peptide described herein in an amount effective to reduce the infectivity of the virus.

In a further aspect, the present disclosure provides an in vitro assay for testing an agent for anti-viral activity against rhinovirus C, the assay comprising the steps of: (a) contacting the agent with a soluble truncated peptide described herein and rhinovirus C; and (b) assaying the ability of the agent to disrupt binding of the soluble truncated peptide to the virus. In some aspect, the assay further comprises (c) incubating the rhinovirus pre-incubated with the peptide and the agent or with the agent alone with host cells, and measuring the infectivity of the rhinovirus in the host cell, wherein the truncated peptide is used as a positive control.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

The invention provides soluble truncated CDHR3 peptides which inhibit rhinovirus C binding to cells and inhibit viral infectivity. The present invention comprises specific regions (specifically the 1st domain of CDHR3) that are required to provide both the binding to RV-C cells and ability to block viral infectivity. These soluble truncated receptors provide the basis for a new in vitro assay for anti-RV-C drug development therapy.

Soluble Truncated Peptides and Compositions

Figure 1:
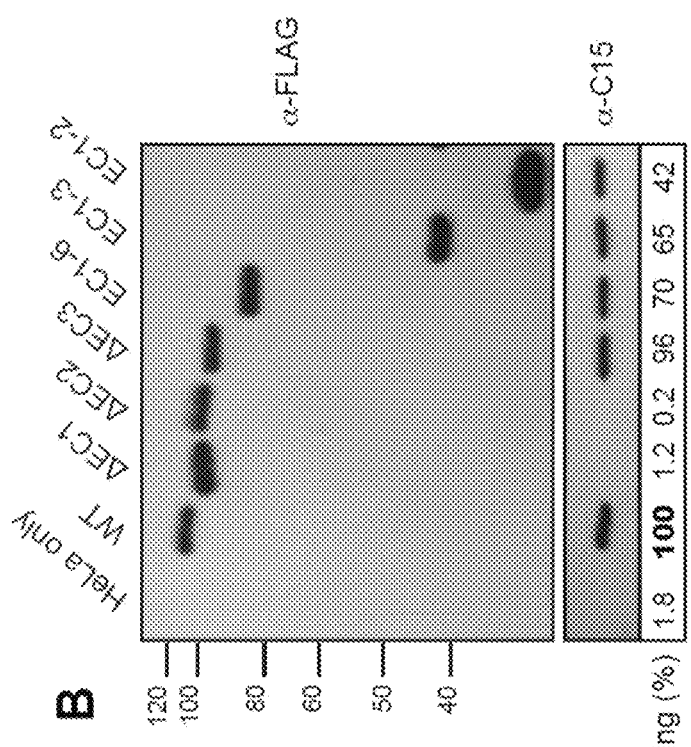
FIG. 1. Mapping RV-C binding domains in CDHR3. (A) Design of CDHR3 EC deletion constructs. (B) Cell lysates of HeLa cells transfected with these cDNAs were reacted with sucrose purified C15 virus ($10^7$ PFUe) as described in Methods. Western assays after immunoprecipitation with an α-His mAb detected CDHR3 (via α-FLAG) and captured virus (α-C15). Binding % is the observed C15 signal pixel count normalized to the CDHR3 protein (α-FLAG) signal in the panel above (Total Lab 100) relative to the WT CDHR3 lane (bold face).
Figure 1:
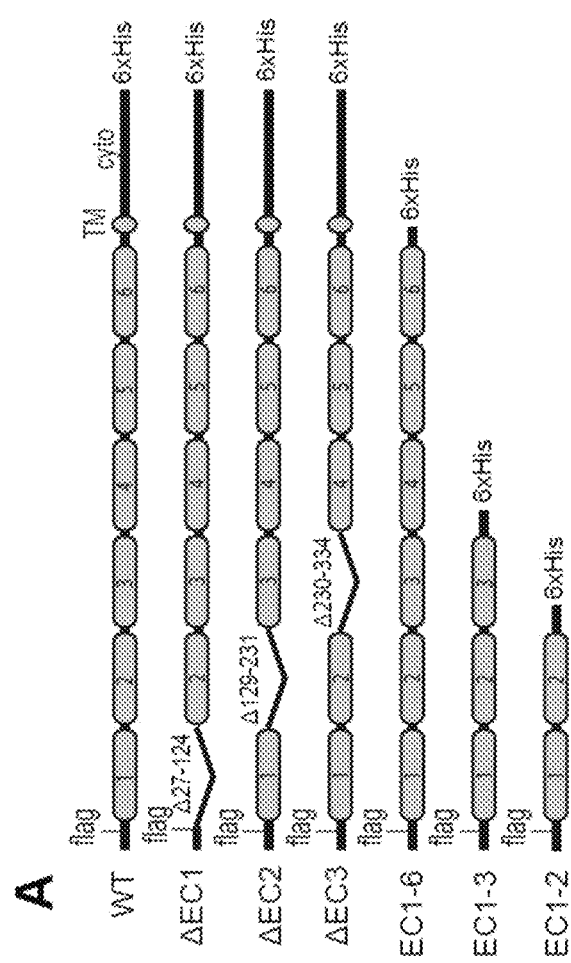
Figure 5:
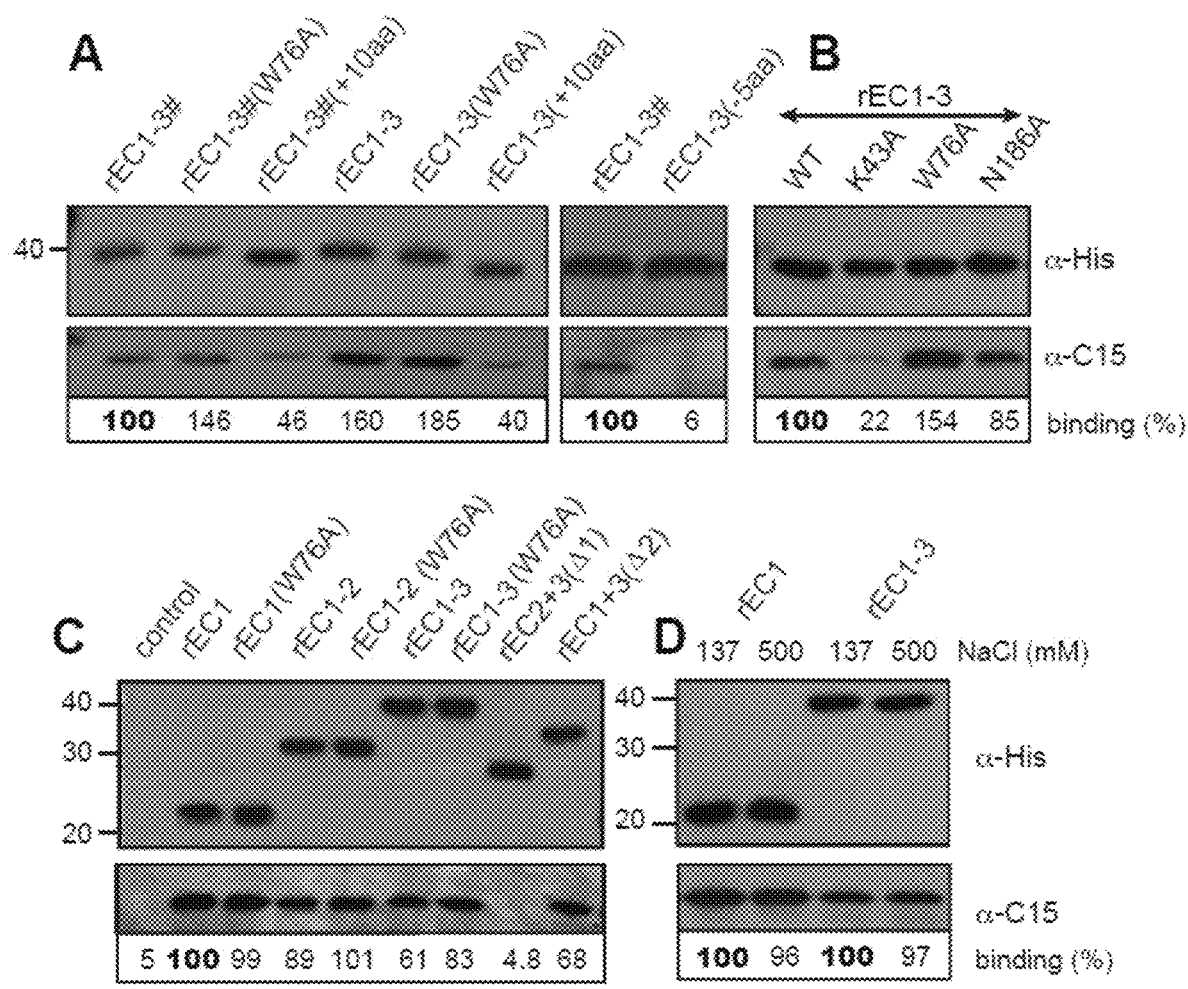
FIG. 5. Recombinant CDHR3 proteins. Bacterially produced CDHR3 fragments (100 pmol) with the indicated C-terminal extensions (A), point mutations (B), or rEC deletions (C) were incubated with C15 virus ($10^7$ PFUe). Immunoprecipitation with an α-His mAb was followed by Western analysis for bound proteins (α-His for CDHR3, and α-C15). As labeled here, "rEC1-3 #" refers to a peptide with CDHR3 residues 20-345; "rEC1-3" is similar except these fragments also have a C345A substitution. (D) Similar to A, the α-His extracted complexes were treated with standard (137 mM) or high (500 mM) NaCl conditions before collection and Western analyses. Each panel (ABCD) is a separate experiment. Binding % is the observed C15 signal pixel count normalized to the recombinant protein (α-His) signal in the panel above (Total Lab 100) relative to positive control (100) in each unit.

Full-length gene expression of CDHR3 in transfected Hela cells has been described (Bochkov, 2015, PNAS 112: 5485). The present invention, using the CDHR3 gene as starting material, produced a series of mammalian and bacterial expression vectors that express different recombinant proteins (see: FIGS. 1 and 5) comprising different arrangements of the 6 domains. The resulting recombinant proteins (see: Sequences in Table 1) tagged with N-proximal FLAG sequences and C-terminal 6×His sequences were isolated and subjected to a specific refolding protocol before testing for biological activity (Example 1). Protein numbering system for the truncated peptide is based on the synthetic sequence of CDHR3 (SEQ ID NO:1) which corresponds to GenBank aic58018.

The panel of deleted transfected versions of the CDHR3 gene was tested for virus binding in HeLa cell lysates. As demonstrated in the examples, truncated proteins synthesized in HeLa cells and containing EC domain 1 (SEQ ID NO:2), including constructs with EC domains 1-2 and 1-3 were uniquely necessary and sufficient for effective virus binding in IP pulldown assays.

The EC1 (SEQ ID NO:20 or 22 (with W76A mutation), EC1-2 (SEQ ID NO:23 or 25 (with W76A mutation)), EC1-3 (SEQ ID NO:24), and EC1+3(Δ2) (SEQ ID NO:26) sequences were engineered into bacterial expression vectors, including point mutations of W76 and C345 relative to SEQ ID NO:1. The rEC1 segment encoded residues 20-130, rEC1-2 encoded residues 20-237, rEC1-3 encoded residues 20-345, rEC2+3(Δ1) encoded residues 20-345 (Δ27-124), rEC1+3(Δ2) encoded residues 20-345 (Δ129-231), rEC1-3 (+10aa) encoded residues 20-355, and rEC1-3(-5aa) encoded residues 20-340 relative to SEQ ID NO:1 amino acid sequence. These units were amplified by PCR from the pHL-FLAG-CDHR3-His cDNAs described above and then ligated into pET11a vectors between the NheI and BamHI restriction sites.

To prevent spurious disulfide formation, most plasmids encoding EC3 segments had a point mutation converting Cys345 to Ala345 (C345A). Additional point mutations were engineered by standard, primer-directed two-step PCR. After much experimentation, a functional protocol for soluble protein isolation was achieved that produces biologically active recombinant proteins capable of binding RV-C15, in a manner similar to the transfection-derived materials previously tested as described in detail in Example 1 in Exhibit A. These recombinant CDHR3 proteins are refolded in the presence of Ca++ which is critical to proper refolding and activity of the proteins, and these *E. coli* derived proteins are not glycosylated as in the naturally occurring CDHR3 receptor. The protein fragment-binding to virus was independent of Asn-186 glycosylation. These peptides were tested and shown that all the constructs containing domain 1 were able to block viral infectivity and replication for at least 4 genotypes of RVC virus.

The present disclosure provides truncated engineered CDHR3 peptides comprising domain 1 (SEQ ID NO:2) of CDHR3 (SEQ ID NO:1). These soluble truncated peptides can include a heterologous tag and are able to bind to RVC virus and to block viral infectivity of RVC. Suitable soluble truncated peptides include (a) soluble truncated peptide comprising domain 1 (SEQ ID NO:2), (b) soluble truncated peptides comprising domain 1 with a W76X mutation (e.g. SEQ ID NO:31 wherein X is an amino acid selected from A, G, V, L, I, S, or T, preferably A (as demonstrated in SEQ ID NO:30)), (c) soluble truncated peptides comprising sequentially linker 1 (SEQ ID NO:15) and domain 1 (SEQ ID NO:2) (for example, SEQ ID NO:33); (d) soluble truncated peptides comprising linker 1 (SEQ ID NO:15) and domain 1 with a W76X mutation (SEQ ID NO:31) (for example, SEQ ID NO:34); (e) soluble truncated peptides comprising SEQ ID NO:20 or 22; (f) soluble truncated peptides comprising SEQ ID NO:21 and sequences which have at least 75% identity to the associated SEQ ID NOs. described, alternatively at least 80% sequence identity, alternatively at least 90% sequence identity, alternatively at least 95% sequence identity, alternatively at least 98% sequence identity to the associated SEQ ID NOs described. It is contemplated that these soluble truncated peptides further comprise an exogenous tag, for example, an N-terminus, C terminus tag or both. In some embodiments, the peptides comprise a C-terminus tag. In other examples, the peptides comprises an N-terminus tag. In some examples, the peptides comprise both a C- and N-terminus tag. For example, SEQ ID NO:19 and SEQ ID NO:21 show two suitable soluble truncated peptides comprising linker 1, domain 1, and suitable tags, however, the present invention contemplates the use of other suitable tags or agents.

As demonstrated in Example 1, the soluble truncated peptides comprising only domain 1 (e.g., rEC1 (SEQ ID NO:20 or 22) and sufficient linker sequences were found to be monomeric, thus do not require higher order oligomerization to be effective for viral binding or biological activity to prevent viral infection and replication in cells. Further, the single domain truncated peptides were also able once properly folded (after production in E. coli) to be removed from the Ca++ buffer and then reintroduced back into Ca++ containing buffer to allow for proper refolding, which was not observed for the longer truncated peptides containing domains 2 or 3 in addition to domain 1 (See FIG. 7D).

In one embodiment, the soluble truncated peptides comprises domain 1 (SEQ ID NO:2) and domain 2 (SEQ ID NO:3) and at least one linker (for example, linker 1 (SEQ ID NO:15), linker 2 (SEQ ID NO:16), linker 3 (SEQ ID NO:17), or a combination thereof). Suitable embodiments contemplated include soluble truncated peptides selected from (a) a soluble truncated peptide comprising domain 1 (SEQ ID NO:2), domain 2 (SEQ ID NO:3) and linker 1 (SEQ ID NO:15) before domain 1; (b) a soluble truncated peptide comprising domain 1 (SEQ ID NO:2), domain 2 (SEQ ID NO:3) and linker 1 (SEQ ID NO:15) before domain 1 and linker 2 (SEQ ID NO: 16) between domain 1 and domain 2 (e.g., SEQ ID NO:23); (c) a soluble truncated peptide comprising domain 1 with the W76X mutation (SEQ ID NO:31), domain 2 (SEQ ID NO:3) and linker 1 (SEQ ID NO:15) before domain 1; (d) a soluble truncated peptide comprising domain 1 with the W76X mutation (SEQ ID NO:31), domain 2 (SEQ ID NO:3) and linker 1 (SEQ ID NO:15) before domain 1 and linker 2 (SEQ ID NO:16) between domain 1 and domain 2; (e) SEQ ID NO:25; and sequences which have at least 75% identity to the associated SEQ ID Nos., alternatively at least 80% sequence identity, alternatively at least 90% sequence identity, alternatively at least 95% sequence identity, alternatively at least 98% sequence identity to the associated SEQ ID NOs. It is contemplated that these soluble truncated peptides further comprise an exogenous tag, for example, an N-terminus, C terminus tag or both. In some embodiments, the peptides comprise a C-terminus tag. For example, SEQ ID NO: 5 and SEQ ID NO:7 are two contemplated soluble truncated peptides which include both domain 1 and domain 2 and at least one tag, although other iterations are contemplated.

In some embodiments, the soluble truncated CDHR3 peptide consists essentially of (i) linker 1 (SEQ ID NO:15) and domain 1 (SEQ ID NO:2) of CDHR3, (ii) linker 1 (SEQ ID NO:15), domain 1 (SEQ ID NO:2), linker 2 (SEQ ID NO:16), and domain 2 (SEQ ID NO:3) of CDHR3; (iii) linker 1 (SEQ ID NO:15), domain 1 (SEQ ID NO:2), linker 2 (SEQ ID NO:16), domain 2 (SEQ ID NO:3, linker 3 (SEQ ID NO:17), domain 3 (SEQ ID NO:4) and linker 4 (SEQ ID NO:18) of CDHR3 or (iv) linker 1 (SEQ ID NO:15), domain 1, linker 3 (SEQ ID NO:17), domain 3 (SEQ ID NO: 4) and linker 4 (SEQ ID NO:18) of CDHR3 (as referenced in SEQ ID NO:1).

In some further embodiments, the peptides consist essentially of SEQ ID NO: 20, 22, 23-27, 30-31, 33, or 34 and at least one tag sequence. The tag may be at the N- or C-terminus. In some further embodiments, the peptides consists essentially of SEQ ID NO: 20, 22, 23-27, 3031, 33 or 34 and at least two tag sequences.

Experiments demonstrated in Example 1 also showed that mutation of amino acid Cys-345 to Ala (C345A) (as referenced to SEQ ID NO:1, located in linker 4) was important to the process of making biologically active receptor materials, specifically the recombinant bacterially-produced protein. When CDHR3 is truncated (to rEC1-3) in bacterial contexts, Cys-345 forms unwanted exogenous disulfide interactions which decrease the solubility of recombinant protein fragment. Mutation of this residue (C345A) increased virus accessibility and binding efficiency by eliminating spurious disulfide formation, which is demonstrated in the denaturing gel data confirming this finding. The binding of rEC1-3 to C15 virus is very tight (i.e. natural interaction) because it can withstand 500 mM NaCl.

A second mutation of Trp-76 to Ala (W76A) (located in domain 1 in reference sequence SEQ ID NO:1) also resulted in truncated peptides (bacterial or in eukaryotic cells) that bind higher quantities of virus. Not to be bound by any theory, this mutation (W76A) works by interfering with native protein dimerization (most cadherins form self-dimers) opening the protein to better virus interactions.

The combination of W76A and C345A is a preferable combination that works synergistically in the rEC1-3 format to increase virus-binding of the engineered soluble truncated peptides.

In some embodiments, when making a recombinant truncated peptide comprising rEC1-3 (with or without W76A), care must be taken in the exact length of the EC3 domain. If the sequence is extended slightly or partially deleted, the virus binding activity may be significantly diminished. Therefore, the present invention contemplates truncated peptides comprising domain 3 and linker 4 having less than 10 additional amino acids at the terminal end beyond position 345 in SEQ ID NO:1. Further, the truncated peptides contemplated herein include domain 3 sequence that is not truncated shorter than position 345 in SEQ ID NO:1.

The recombinant truncated peptide of rEC1, rEC1-2, rEC1-3 (C345A) or rEC1+3(Δ2) demonstrates inhibitory biological activity that prevents C15 virus from binding to susceptible HeLa cells, and consequently inhibits subsequent virus replication. The degree of inhibition is proportional to the amount of protein used to treat cells, as would be expected if these truncated peptides (a) bound directly to the virus, or (b) formed complexes with native cellular CDHR3, thereby blocking virus binding sites.

As described in more detail below, soluble truncated CDHR3 peptides comprising domain 1, domains 1 and 2, domains 1, 2, and 3, or domains 1 and 3 are able to bind to virus and the binding is independent of the peptide being glycosylated. EC domain 1 is necessary for effective blocking of viral infectivity. The present invention contemplates soluble truncated CDHR3 peptides comprising, consisting essentially of, or consisting of domain 1, domains 1 and 2, domains 1 and 3 or domains 1, 2 and 3 and, in some embodiments, having at least one mutation of the cysteine at position 345 (C345) relative to SEQ ID NO:1. In some preferred embodiments, the peptides further contain at least one tag that does not alter their viral binding or inhibitory properties. In preferred embodiments, the contemplated soluble truncated CDHR3 peptides do not contain domains 4, 5, or 6 of SEQ ID NO:1 as depicted in FIG. 2.

Figure 2:
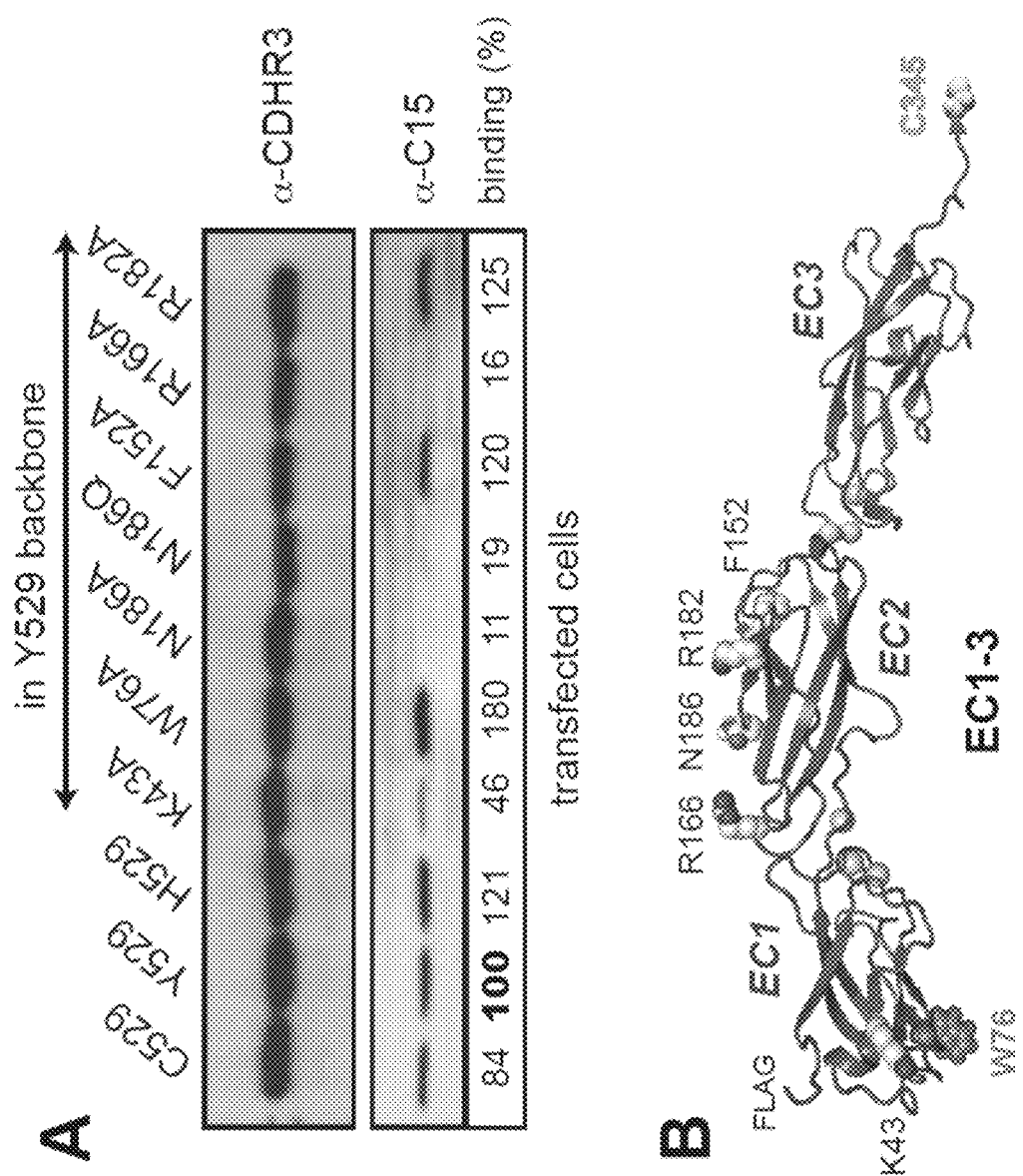
FIG. 2. CDHR3 mutations. (A) Lysates from HeLa cells transfected with full-length CDHR3 cDNAs encoding the specified point mutations were reacted with C15 virus. Immunoprecipitation and protein detection used an α-CDHR3 mAb reactive with the cytoplasmic domain. Captured virus was quantitated as in FIG. 1. (B) PyMol depiction of computed model by Robetta [23,56] of rEC1-3 segments show putative locations of mutations. Green spheres predict calcium binding sites, red depicts Asp+Glu sequences.
Figure 3:
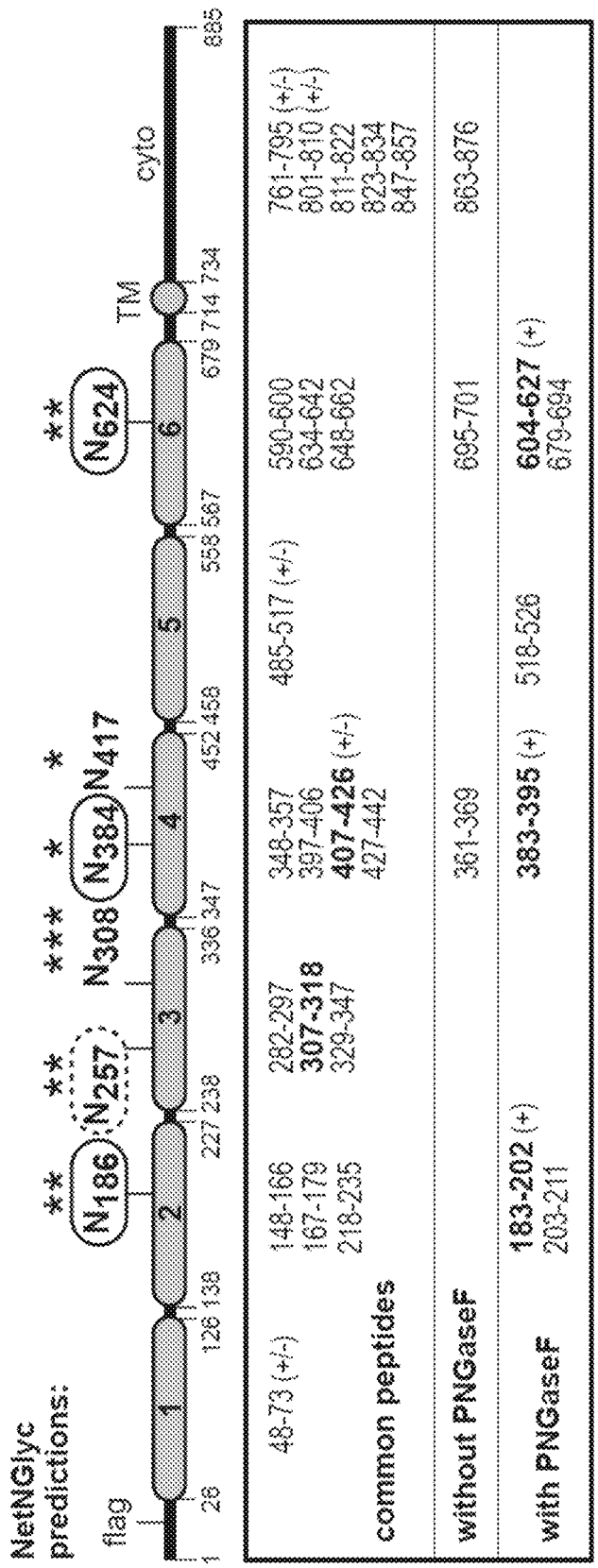
FIG. 3. CDHR3 glycosylation. HeLa cell lysates from cells transfected with cDNA for full-length CDHR3 (Y529) were gel fractionated. The CDHR3 band was treated (or not) with PNGaseF before trypsin digestion and analysis by mass spectrometry. Identified peptides are indicated: (+) deamide form of peptide; (+/−) amide and deamide forms. NetNGlyc strength is according to primary sequence data (* is low, *** is high). Protein numbering is from GenBank AIC58018, with EC delineation from the current structure model [23].
Figure 4:
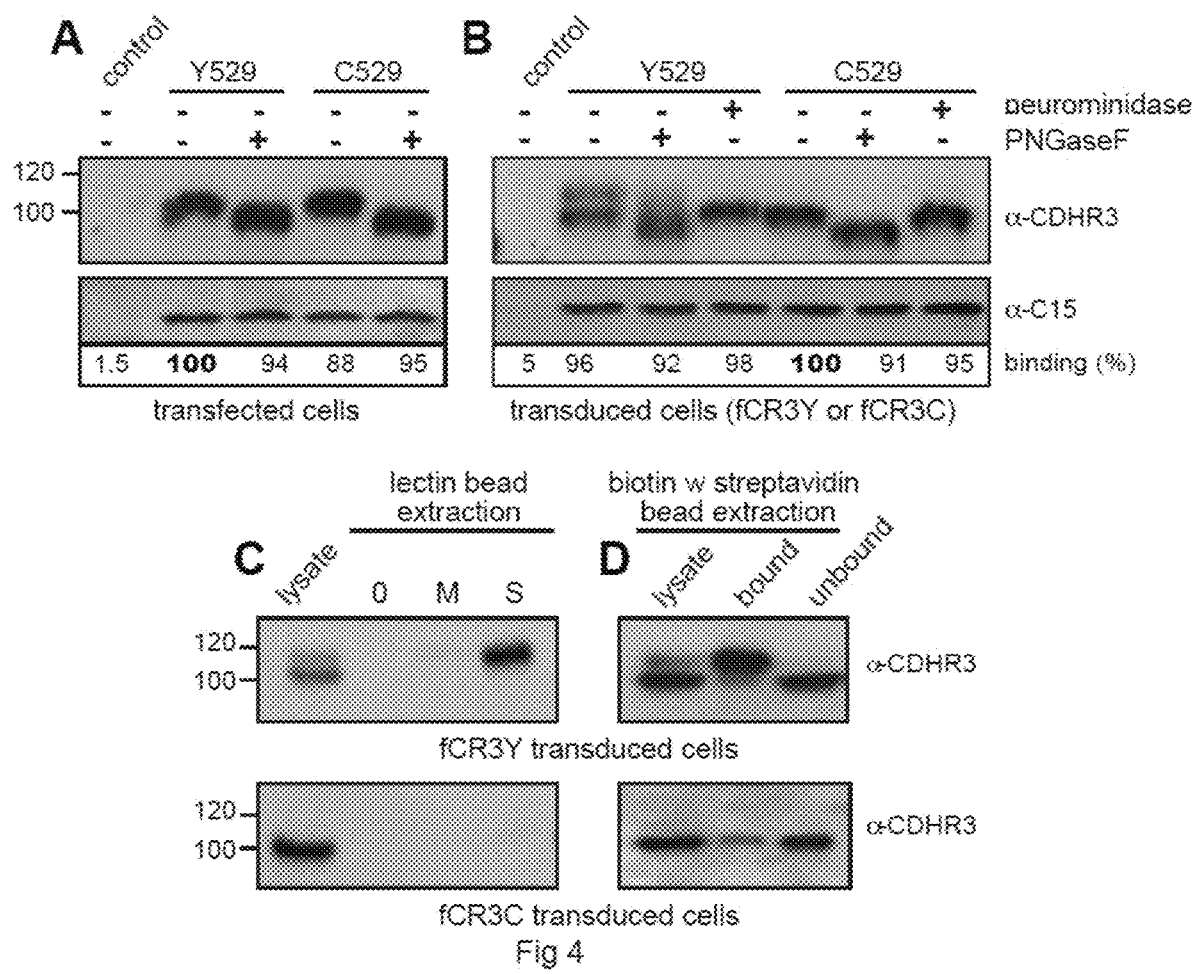
FIG. 4. Virus binding and CDHR3 glycosylation. Lysates from HeLa cells transfected (A) or transduced (B) with full-length cDNAs encoding Y529 or C529 CDHR3 proteins were reacted with C15 virus in the presence or absence of PNGaseF or neuraminidase as described in Methods. Immunoprecipitation and protein detection used an α-CD HR3 mAb reactive with the cytoplasmic domain. Captured virus was quantitated as in FIG. 1. (C) As in B, transduced cell lysates were treated (or not) with biotinylated Sambucus nigra (S) or Maackia amurensis (M) lectins before extraction with streptavidin agarose beads and protein detection with α-CDHR3. (D) Plated stably transduced HeLa cells expressing FLAG-Y529 or C529 CDHR3 were biotinylated and labeled cell surface proteins were isolated with streptavidin agarose beads.

The term "truncated" with regard to the specific protein/peptide sequence as used herein describes the soluble truncated CDHR3 peptides including at least domain 1, for example, domains 1 and 2, domains 1, 2 and 3 and domains 1 and 3 as depicted in FIG. 2 and FIG. 1A using numbering based on the synthetic sequence of CDHR3 (SEQ ID NO:1) which corresponds to GenBank aic58018 and which does not include the sequences of domains 4, 5 and 6 of wildtype CDHR3. The truncated peptides do not encompass full length CDHR3 sequence (CDHR3). The soluble truncated peptides contemplated herein encompass peptides having 350 amino acids or less of the full length CDHR3 domain. In some embodiments, the soluble truncated peptides include at least one mutation within the peptide sequence from SEQ ID NO:1, preferably at the cysteine at position C345 relative to SEQ ID NO:1. Further "of the truncated peptides" contemplates that the length of the peptide may add less than 10 amino acids relative to position 345 of SEQ ID NO:1 but there is no deletion of amino acids relative to position 345, as FIG. 5 demonstrated a 5 amino acid truncation results in loss of viral binding (e.g. 1-9 amino acids may be added after position 345 relative to SEQ ID NO:1, but no amino acid truncations shorter than amino acid 345 are contemplated).

In a preferred embodiment, the soluble truncated peptides do not contain amino acids of domains 4, 5, or 6 of CDHR3 of SEQ ID NO:1. In some embodiments, the truncated peptides encompass slight variation in the amino acid sequences that do not alter the functional properties of the peptide (e.g. does not disrupt the ability of the peptide to bind virus and to inhibit infectivity).

The invention encompasses truncated peptides that have more than one mutation, for example, the additional mutation at amino acid position 76 in domain 1 (as referenced in SEQ ID NO:1, e.g., W76X, wherein X is selected from A, G, V, L, I, S or T). For example, but not limited to, suitable sequences of the truncated peptides can be found in SEQ ID NO:22 or 31 which are domain 1 with a W76X mutation, and SEQ ID NO:30 which is domain 1 with W76A mutation. In contemplated soluble truncated peptides that contain domain 3 in addition to domain 1, suitable peptides have the mutation of amino acid position 76 in domain 1 (as referenced in SEQ ID NO:1) in addition to the cysteine mutation at position 345, the combination of which may increase the functionality of the peptides but does not greatly diminish the functionality of the peptide (e.g., does not reduce the functionality of the peptide by more than 20%).

The term "at least one mutation" includes additional amino acid mutations or substitutions within the contemplated soluble truncated peptides that do not greatly diminish (e.g. reduce by more than 20%) the functionality of the peptides in binding of virus or inhibiting infectivity.

As used herein, the term "mutated" or "mutation" refers to both substitutions of amino acids or a deletion of an amino acid within the wild type sequence to produce a modified sequence. In a preferred embodiment, the mutation is a substitution.

The soluble truncated peptides may be covalently or non-covalently attached to a heterologous tag which does not disrupt the functionality of the peptide (e.g., does not disrupt the ability of the peptide to bind virus and to inhibit infectivity). The heterologous tag is a sequence that is not naturally occurring in the CDHR3 protein or peptide.

A "peptide" is used interchangeably with the term "protein" and "polypeptide" and refers to a chain-type polymer formed by amino acid residues which are linked to each other via peptide bonds.

In one embodiment, the present invention provides a soluble truncated CDHR3 peptide comprising, consisting essentially of, or consisting of domain 1 and domain 3 of CDHR3 (SEQ ID NO:1) or sequence that is at least 90% identical to domains 1 and domains 3 of CDHR3, or domain 1, 2 and 3 of CDHR3 or sequence that is at least 90% identical to domains 1,2 and 3, and comprising at least one amino acid mutation comprising mutation of the cysteine at position 345 (C345) relative to SEQ ID NO:1 mutated to another amino acid, for example, an amino acid selected from the group consisting of alanine (A), glycine (G), valine (V), leucine (L), isoleucine (I), serine (S), and threonine (T). In a preferred embodiment, the cysteine is mutated to an alanine (e.g. C345A).

For clarity of the invention described herein, the domains of CDHR3 are domains of the CDHR3 protein found in SEQ ID NO:1 and all numbers refers to this full protein sequence that corresponds to Genbank #Locus:aic58018. As described herein, domain 1 (SEQ ID NO:2) is amino acids 26-128 of SEQ ID NO:1, domain 2 (SEQ ID NO:3) is amino acids 141-231 of SEQ ID NO:1; and domain 3 (SEQ ID NO:4) is amino acids 242-341 of SEQ ID NO:1. There are linker/spacer regions associated before/after each domain which are believed to be important for proper folding of the proteins. For use herein, the linker/spacers are numbered from N-terminus to C terminus as follows: linker 1 before domain 1 (SEQ ID NO:15, aa 20-25 of SEQ ID NO:1), linker 2 between domain 1 and 2 (SEQ ID NO:16, aa 129-140 of SEQ ID NO:1), linker 3 (SEQ ID NO:17, aa 232-241 of SEQ ID NO:1) located between domain 2 and domain 3, and linker 4 (SEQ ID NO:18, aa 342-345) located after domain 3 (C-terminus).

In one embodiment, a truncated peptide comprising or consisting essentially of domain 1, domain 2 and domain 3 and a sufficient amount of the linkers to allow proper folding of the domains, for example, linker 1, 2, 3 and 4.

In one embodiment, a truncated peptide comprising or consisting essentially of SEQ ID NO:2, SEQ ID NO:3, and SEQ ID NO:4 and linkers 1, 2, 3 and 4, and containing at least one mutation at the C-terminal cysteine in linker 4 (SEQ ID NO:4) to an amino acid selected from the group consisting of A, G, V, L, I, S, and T is contemplated. In some embodiments, linkers 1, 2, 3 and 4 are further included in the truncated peptide. In another embodiment, a truncated peptide comprises or consists essentially of SEQ ID NO:2 and SEQ ID NO:4 consecutive in the soluble truncated peptide and including linker 1, 3 and 4 is contemplated (e.g., consecutive SEQ ID NO:15 (linker 1)-SEQ ID NO:2 (domain 1)-SEQ ID NO:17 (linker 3)-SEQ ID NO:4 (domain 3)-SEQ ID NO:18 (linker 4), for example: SEQ ID NO:14).

In some embodiments, the truncated peptides comprise at least one mutation at the terminal cysteine (e.g. amino acid position C345 of SEQ ID NO:1) and in further embodiments, also include at least one mutation in amino acid at position 76 (W76) relative to SEQ ID NO:1, wherein each of the positions are mutated to an amino acid selected from the group consisting of alanine, glycine, valine, leucine, isoleucine, serine and threonine. In a preferred embodiment the two amino acids are mutated to alanine.

In one embodiment, the soluble truncated CDHR3 peptide comprises or consists essentially of domain 1, domain 2 and domain 3 of CDHR3 or a consecutive sequence at least 90% similar to domains 1, 2 and 3 wherein the terminal cysteine at position 345 relative to SEQ ID NO:1 is mutated to another amino acid, for example, an amino acid selected from the group consisting of alanine, glycine, valine, leucine and isoleucine, serine and threonine. In one embodiment, the soluble truncated peptide is amino acids 20-345 of SEQ ID NO:1 containing the mutation of C345A. In a further embodiment, the soluble truncated peptide is amino acids 20-345 of SEQ ID NO:1 containing the C345A and W76A mutations. In a further embodiment, the soluble truncated peptide comprises or consists essentially of amino acids 20-345 of SEQ ID NO:1 with the C345A mutation and a sequence comprising a tag, for example a HIS tag or a FLAG tag located at the N-terminus, C-terminus or both of the truncated peptide. In another embodiment, the truncated peptide sequence comprises the amino acids of an N-terminal FLAG tag, a C-terminal HIS tag or a combination thereof.

In some embodiments, the soluble truncated CDHR3 peptides containing domains 1, 2 and 3 or domains 1 and 3 have substantial identity of those domains to the domains identified in SEQ ID NO:1 but contain at least one amino acid mutation altered from the peptide sequence of SEQ ID NO:1 (preferably mutation of the W at position 76 in domain 1 or the terminal cysteine, e.g. C345 mutation relative to SEQ ID NO:1 wherein the mutation is to an amino acid selected from the group consisting of alanine, glycine, valine, leucine and isoleucine, serine and threonine). In some embodiments, the domains have at least 75% identity to the CDHR3 domains 1 2 and 3, alternatively at least 80% sequence identity, alternatively at least 90% sequence identity, alternatively at least 95% sequence identity. It is contemplated in some of these embodiments, there are at least two mutations within the soluble truncated CDHR3 peptides from the wild-type sequence of the truncated domains.

Protein and nucleic acid sequence identities are evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" or "percent similarity" is determined by comparing two optimally aligned sequences over a comparison window, wherein the portion of the polynucleotide or peptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantial similarity" of polynucleotide or peptide sequences means that a polynucleotide or peptide comprises a sequence that has at least 75% sequence identity. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 75%. Preferred percent identity of polypeptides can be any integer from 75% to 100%. More preferred embodiments include at least 75%, 80%, 85%, 86%, 87%, 88%, 89%, 90%, 91%, 92%, 93%, 94%, 95%, 96%, 97%, 98%, 98.7%, or 99%.

In another embodiment, the soluble truncated CDHR3 peptide consists essentially of (i) amino acids 20-345 of SEQ ID NO:1 with C345A mutation; (ii) amino acids 20-345 of SEQ ID NO:1 with C345A mutation and W76A mutation, (iii) amino acids 20-128 and 232-345 of SEQ ID NO:1 consecutive in the peptide and wherein the peptide contains C345A mutation; or (iv) amino acids 20-128 and 232-345 of SEQ ID NO:1 with C345A and W76A mutations, and optionally wherein any of the truncated peptides (i)-(iv) further comprise the amino acid sequence of a tag at the C-terminus, N terminus or both of the peptide sequence.

In one embodiment, the soluble truncated CDHR3 peptide consists essentially of the peptide of SEQ ID NO:19 (FLAG-CDHR3 EC1-HIS), SEQ ID NO:22 (FLAG-CDHR3-EC1-His W76A); SEQ ID NO:5 (FLAG_CDHR3 EC1-2), SEQ ID NO:6 (FLAG-CDHR3 EC1-3 HIS), SEQ ID NO:7 (FLAG-CDHR3 EC1-2 W76A), SEQ ID NO:8 (FLAG-CDHR3-W76A EC1-3-HIS) or SEQ ID NO:9 (FLAG-CDHR3 EC1+3 (Δ2)).

Suitable soluble truncated CDHR3 peptides of the present disclosure are truncated peptides that contain at least domain 1 (SEQ ID NO:2) or domain 1 with a W76X mutation (SEQ ID NO:31). In some embodiments, the soluble truncated CDHR3 peptides comprise or consist essentially of (a) domain 1 (SEQ ID NO:2) of CDHR3 or (b) domain 1 of CDHR3 with a mutation at position 76 relative to SEQ ID NO1 (e.g., SEQ ID NO:31), wherein X is selected from the amino acids consisting of A, G, V, L, I, S, and T, preferably in one embodiment, A).

In some embodiments, the soluble truncated CDHR3 peptide containing domain 1 (or domain 1 with W76X mutation) further comprises at least one linker, for example, linker 1 (SEQ ID NO:15) before domain 1, linker 2 (SEQ ID NO:16) after domain 1, or both. For example, suitable soluble truncated CDHR3 peptides of the present disclosure are SEQ ID NO:20, SEQ ID NO:22, SEQ ID NO:30, SEQ ID NO:33, or SEQ ID NO:34. In some embodiments, the soluble truncated CDHR3 peptide further comprises a heterologous tag. Suitable peptides with a heterologous tag include, but are not limited to, for example, SEQ ID NO:19 (FLAG-EC1-his) or SEQ ID NO: 21 (FLAG-EC1-his with W76A).

In some embodiments, the truncated CDHR3 peptides of the present disclosure are truncated peptides that contain at least domain 1 (SEQ ID NO:2) or domain 1 with a W76X mutation (SEQ ID NO:31) and further comprise additional subsequent sequence selected from the group consisting of (i) domain 2 of CDHR3 (SEQ ID NO:3); (ii) domain 3 of CDHR3 (SEQ ID NO:4); (iii) domain 2 (SEQ ID NO:3) and domain 3 (SEQ ID NO:4) of CDHR3; (d) at least one linker, wherein the at least one linker is before domain 1 (linker 1), between domain 1 and 2 (linker 2), between domain 2 and 3 (linker 3), or after domain 3 (linker 4), or (e) a combination of any one of (i)-(iii) and (iv). For example, the suitable linkers can be selected from (a) linker 1 (SEQ ID NO:15) before domain 1, (b) linker 2 (SEQ ID NO: 16) between domain 1 and 2; (c) linker 3 (SEQ ID NO:17) positioned between domain 2 and 3; (d) linker 4 (SEQ ID NO:18) positioned after domain 3, wherein X is, and (e) a combination of any of (a)-(d).

One suitable example of a soluble truncated protein comprises domain 1 (SEQ ID NO:2) and domain 3 of CDHR3 (SEQ ID NO:4) and at least linker 4 (SEQ ID NO:18). In another example, the soluble truncated protein comprises linker 1 (SEQ ID NO:15), domain 1 (SEQ ID NO:2), linker 3 (SEQ ID NO:17), domain 3 of CDHR3 (SEQ ID NO:4) and at least linker 4 (SEQ ID NO:18)

Other suitable truncated CDHR3 peptides comprise or consist essentially of sequentially: (a) linker 1 (SEQ ID NO:15), domain 1 (SEQ ID NO:2), linker 2 (SEQ ID NO:16), and domain 2 (SEQ ID NO:3); (b) linker 1 (SEQ ID NO:15), domain 1 with W76X mutation (SEQ ID NO:30), linker 2 (SEQ ID NO:16), and domain 2 (SEQ ID NO:3); (c) linker 1 (SEQ ID NO:15), domain 1 with W76X mutation (SEQ ID NO:30), linker 2 (SEQ ID NO:16), domain 2 (SEQ ID NO:3), and linker 3 (SEQ ID NO:17); (d) linker 1 (SEQ ID NO:15), domain 1 (SEQ ID NO:2), linker 2 (SEQ ID NO:16), domain 3 (SEQ ID NO:4) and linker 4 (SEQ ID NO:18); (e) linker 1 (SEQ ID NO:15), domain 1 with W76X mutation (SEQ ID NO:30), linker 2 (SEQ ID NO:16), domain 3 (SEQ ID NO:4) and linker 4 (SEQ ID NO:18); and (f) linker 1 (SEQ ID NO:15), domain 1 with W76X mutation (SEQ ID NO:30), linker 2 (SEQ ID NO:16), domain 2 (SEQ ID NO:3), and linker 3 (SEQ ID NO:17), domain 3 (SEQ ID NO:4) and linker 4 (SEQ ID NO:18). For example, suitable truncated CDHR3 peptides may be the amino acid sequence of any one of SEQ ID NO: 23-27.

In other examples, the soluble truncated CDHR3 peptide consists essentially of an amino acid sequence selected from the group consisting of: SEQ ID NO:2, 5-9, 19-27, 30-31, 33-34, and a sequence at least 90% identity to SEQ ID NO:2, 5-8, 19-27, 30-31 and 33-34. In a further example, the soluble truncated CDHR3 peptides is an amino acid sequence selected from the group consisting of SEQ ID NO, 5-9, 19 and 21, or an amino acid sequence having at least 90% identity to SEQ ID NO, 5-9, 19 and 21.

In another set of examples, the soluble truncated CDHR3 peptide comprises or consists essentially of (i) amino acids 20-345 of SEQ ID NO:1 with C345A mutation; (ii) amino acids 20-345 of SEQ ID NO:1 with C345A mutation and W76A mutation, (iii) amino acids 20-128 and 232-345 of SEQ ID NO:1 with C345A mutation; (iv) amino acids 20-128 and 232-345 of SEQ ID NO:1 with C345A and W76A mutations, (v) amino acids 20-237 of SEQ ID NO:1; (vi) amino acids 20-130 of SEQ ID NO:1; or (vi) amino acids 20-130 of SEQ ID NO:1 with W76A mutation. Some suitable examples of the truncated CDHR3 peptide are SEQ ID NO:6 (FLAG-CDHR3 EC1-3 HIS), SEQ ID NO:8 (FLAG-CDHR3-W76A EC1-3-HIS), SEQ ID NO:9 (FLAG-CDHR3 EC1+3 (Δ2)), SEQ ID NO:19 (FLAG-CDHR3-EC1) or SEQ ID NO:21.

All soluble truncated peptides described herein can be made in a suitable host cells line. Suitable host cells include prokaryotic or eukaryotic cells. Suitable eukaryotic cells include mammalian cells, for example, animal or human cells (including, but not limited to, for example, HeLa cells, HEK293S cells or CHO cells) by transfection or transduction of the cells with a vector encoding and capable of expressing the CDHR3 peptides. In some embodiments, the soluble truncated peptides are fully or partially glycosylated. In other embodiments, the proteins are not glycosylated. In another embodiment, a suitable host cell is a yeast cell.

In some embodiments, as demonstrated by the Examples, the soluble truncated peptides described herein may be completely unglycosylated as glycosylation is not necessary for viral binding or inhibiting viral infectivity of the peptides. In one embodiment, the peptides are made as recombinant proteins in bacterial cells by transfection of bacterial cells with a suitable vector encoding and able to express the recombinant truncated CDHR3 peptides. Suitable bacteria for producing recombinant protein are known in the art and include, but are not limited to E. coli. The recombinant truncated peptides are expressed in bacteria and contained within inclusion bodies within the bacteria. The inclusion bodies can be isolated and the proteins solubilized and refolded by the methods described herein, requiring refolding and preparing in a suitable carrier containing Ca++.

The term "soluble peptide" as used herein refers to the peptide that does not include the membrane-spanning and cytoplasmic domains present in the naturally occurring, non-soluble form.

In some embodiments, the truncated peptide further contains an exogenous or heterologous tag or agent. In some embodiments, the truncated peptide is directly or indirectly linked to an exogenous or heterologous tag or agent. The suitable tag or agent does not interfere with the functionality of the soluble truncated CDHR3 peptides' function in viral binding or inhibiting viral infectivity. Further, the exogenous or heterologous tag is not native to the CDHR3 protein nor derived from the human CDHR3 protein.

In some embodiments, the heterologous tag or agent is a polypeptide, wherein the polypeptide is translated concurrently with the soluble truncated CDHR3 peptide's nucleic acid sequence.

The term "tag" or "agent" as used herein includes any useful exogenous moiety that allows for the purification, identification, detection, diagnosing, imaging, or therapeutic use of the peptides of the present invention. The terms tag or agent includes epitope tags or detection markers, including, for example, enzymatic markers, fluorescence markers, radioactive markers, among others. The tags or agents are not naturally found in the peptide sequence. Additionally, the term agent includes therapeutic agents, small molecules, and drugs, among others. Suitable tags are known in the art and include, but are not limited to, affinity or epitope tags (non-limiting examples include, e.g., cMyc, HIS, FLAG, V5-tag, HA-tag, NE-tag), florescence tags (RFP, GFP, etc.). Suitable agents include agents that help with the bioavailability or targeting of the peptide. In some embodiments, the peptide is encoded in a nucleic acid sequence that encodes both the peptide and the tag (for example a FLAG, HIS or HA tag).

The present invention also contemplates purified and isolated nucleic acid sequences (e.g. DNA sequences) encoding the soluble truncated CDHR3 peptides, vectors comprising the DNA sequences able to express the soluble truncated CDHR3 peptide in host cells and host cells comprising the DNA or vectors capable of expressing the soluble truncated CDHR3 peptides. In one embodiment, the present invention provides nucleic acid sequences encoding the truncated peptides comprising domain 1 domain 1 with a W76 mutation; domain 1 and 2; domain 1 and 2 with a W76 mutation; domain 1, 2, and 3 of CDHR3 with a C345 mutation; domain 1, 2 and 3 with a W76 and C345 mutation; domain 1 and 3 of CDHR3 with a W76 and C345 mutation; and domain 1 and 3 of CDHR3 with a C345 mutation as described herein. In one example, the vector comprises the nucleic acid sequence selected from the group consisting of SEQ ID NO:10 (EC1-2), SEQ ID NO:11 (EC1-2 W76A), SEQ ID NO:12 (EC1-3), SEQ ID NO:13 (EC1-3W76A), SEQ ID NO:14 (EC1+3(Δ2)), SEQ ID NO:28 (EC1), or SEQ ID NO:29 (EC1 W76A).

In suitable exemplary embodiments, the DNA sequences contemplated herein include, but are not limited to, SEQ ID NO:10, SEQ ID NO:11, SEQ ID NO: 12, SEQ ID NO:13, SEQ ID NO:14, SEQ ID NO:28 or SEQ ID NO:29.

The term "vector" refers to a nucleic acid molecule capable of transporting another nucleic acid to which it has been linked and expressing the gene encoded within the nucleic acid sequence. One type of vector is a "plasmid", which refers to a circular double stranded DNA loop into which additional DNA segments may be ligated, specifically exogenous DNA segments of the targeted protein. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of exogenous genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors, such as viral vectors (e.g., replication defective retroviruses, adenoviruses and adeno-associated viruses), which serve equivalent functions.

In some embodiments, the heterologous sequence of the vector is a viral sequence. Suitable viral sequences include, but are not limited to, an adeno-associated viral sequence or a retroviral sequence. In a preferred embodiment, the heterologous nucleic acid sequence is a recombinant adeno-associated virus. In some embodiments, the virus is an adeno-associated virus (rAAV), a lentivirus, an adenovirus, a herpes simplex virus, a baculovirus, among others. Further embodiments include viruses made using the viral vectors described herein. Suitable methods for making the viruses are known in the art.

Vectors can also include additional selectable marker genes and other genetic elements known in the art.

A vector can preferably transduce, transform or infect a cell, thereby causing the cell to express the proteins encoded by the vector.

In one embodiment, the vectors can comprise a nucleic acid sequence selected from the group consisting of SEQ ID NO:10 (EC1-2), SEQ ID NO:11 (EC1-2 W76A), SEQ ID NO:12 (EC1-3), SEQ ID NO:13 (EC1-3W76A), SEQ ID NO:14 (EC1+3(Δ2)), SEQ ID NO:28 (EC1), and SEQ ID NO:29 (EC1 W76A).

Method of Producing Recombinant Peptides

In another embodiment, the invention provides a method of making the soluble truncated recombinant peptide described herein in bacterial cells. The method comprises the steps of: (a) transforming bacterial cells with the vector encoding and able to express the soluble truncated recombinant peptide; (b) lysing bacterial cells and collecting the inclusion bodies comprising the soluble peptide by centrifugation; (c) solubilizing the peptide within the inclusion body; and (d) dialyzing and refolding the peptide in buffer supplemented with Ca++(e.g., $CaCl_2$)) to produce soluble truncated recombinant peptides of CDHR3 In some embodiments, the method further comprises before step (b) inducing recombinant peptide expression in the bacteria cells. Methods of inducing bacterial cells are known in the art, and include, but are not limited to, Isopropyl β-D-1-thiogalactopyranoside (IPTG) for use in bacterial vectors containing a lac operator. Methods of solubilizing the protein and refolding the protein are known in the art and described in the examples. Suitably, the soluble truncated CDHR3 peptides described herein require the presence of Ca++(e.g. $CaCl_2$)) during the refolding and dialysis. The final soluble truncated CDHR3 peptides must be stored in a buffer containing Ca++(e.g. $CaCl_2$)). Suitable ranges of $CaCl_2$) in the buffer solution include from about 2 mM to 10 mM, preferably from 2 mM to 5 mM, for example, about 3 mM.

A specific protocol for making the rEC, rEC1-2, rEC1-3 and rEC1+3(Δ2) is described here. Bacterial plasmids for the expression of various CDHR3 rEC domains, linked to amino-terminal FLAG-tags and carboxyl-terminal 6×His tags, were constructed. The rEC1 segment encoded residues 20-130, rEC1-2 encoded residues 20-237, rEC1-3 encoded residues 20-345, rEC2+3(Δ1) encoded residues 20-345 (Δ27-124), rEC1+3(Δ2) encoded residues 20-345 (Δ129-231), rEC1-3(+10aa) encoded residues 20-355, and rEC1-3 (-5aa) encoded residues 20-340. These units were amplified by PCR from the pHL-FLAG-CDHR3-His cDNAs described above and then ligated into pET11a vectors between the NheI and BamHI restriction sites. To prevent spurious disulfide formation, most plasmids encoding EC3 segments had a point mutation converting Cys345 to Ala345 (C345A). Additional point mutations were engineered by standard, primer-directed two-step PCR. *Escherichia coli* BL21(DE3) pLysS cells, transformed with each plasmid were induced with IPTG (isopropyl-β-d-thiogalactopyranoside) for recombinant protein expression. The cells were collected by centrifugation, resuspended in lysis buffer (20 mM Tris, pH 8.0, 137 mM NaCl, 1% Triton-X100), and sonicated. The majority of recombinant material was insoluble and collected by centrifugation (20,000×g for 45 min at 4° C.). The pellets were washed (1 M NaCl, then 1 M urea, then water) and solubilized (6 M urea, 20 mM Tris, pH 8.0, 137 mM NaCl for 1 h at 25° C. or O/N at 4° C.). After clarification (20,000×g for 45 min at 4° C.), the supernatants of rEC1 and rEC1-2 proteins were purified under denaturing conditions (6 M urea, 20 mM Tris, pH 8.0, 137 mM NaCl) on HisTrap FF columns (GE Healthcare). After elution with 200 mM Imidazole, the proteins were diluted (to 0.1-0.2 mg/mL) in the solubilization buffer (above) supplemented with 3 mM $CaCl_2$) and then dialyzed (4 times, 8-12 hrs each, against 20 mM Tris, pH 8.0, 137 mM NaCl, 3 mM $CaCl_2$), 2 mM β-mercaptoethanol). Proteins containing the EC3 domain [rEC1-3, rEC2+3(Δ1), and rEC1+3(Δ2)] bound poorly to the HisTrap FF columns even under denaturing conditions so the clarified supernatants were diluted and refolded as described above. Refolded proteins were concentrated using Amicon Ultra centrifugal filters. The soluble receptors bind virus in an in vitro assay. We note that the bacterial constructs can be made without one of the tags, for example, without the FLAG tag and the C-terminal tag (for example the C terminal HIS tag) may be used for purification of the peptide. Other suitable tags are known in the art and contemplated to be able to be switched out the FLAG or HIS tag described above.

Therapeutic Compositions and Methods of Use

The present invention also contemplates therapeutic compositions for reducing or preventing rhinovirus C entry into cells. The therapeutic compositions comprise the soluble truncated peptides of CDHR3, Ca++(e.g. $CaCl_2$)) and a pharmaceutically acceptable carrier.

A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. Typically phosphate buffered saline or other saline solutions are physiologically acceptable carriers. Water is not contemplated as a suitable physiologically acceptable carrier. In some embodiments, additional components may be added to preserve the structure and function of the peptides of the present invention, but are physiologically acceptable for administration to a subject. Ca++(for example, but not limited to, $CaCl_2$)) is a necessary addition to the pharmaceutically acceptable carrier in order to preserve the function of the peptides' ability to bind to virus and inhibit viral entry.

Methods for reducing infection by human rhinovirus C in a host cell susceptible to infection by HRV-C are also contemplated. The methods comprise contacting the virus with an effective amount of the soluble truncated peptide or a pharmaceutical composition comprising the soluble truncated peptide described herein in an amount effective to reduce the infectivity of the virus. In some embodiments, the method is performed in vivo. Methods of performing in vivo include administering to a subject the soluble truncated peptide or pharmaceutical composition in an amount effective to reduce HRV-C infection within the subject.

Methods for treating a subject having human rhinovirus C infection are also contemplated in the present invention. The methods comprise administering to the subject an effective amount of the soluble truncated peptide or pharmaceutical composition comprising the soluble truncated peptide, wherein the effective amount is able to treat one or more symptoms of human rhinovirus C infection.

Routes of administering the soluble truncated peptides and therapeutic compositions in vivo are by appropriate contact with those areas of the body susceptible for infection by HRV, e.g., by any intranasal spray.

The term "treating" or "treatment" includes, but is not limited to, reducing, inhibiting or preventing one or more signs or symptoms associated with rhinovirus C infection. Treating also includes the ability to inhibit or reduce rhinovirus infection within the subject, including the ability to reduce the number of infective rhinovirus particles within the subject, for example, by reducing the number of rhinovirus particles in respiratory droplets or mucus. Symptoms of rhinovirus C infection include, but are not limited to, sore throat, runny nose, nasal congestion, sneezing and cough; muscle aches, fatigue, malaise, headache, muscle weakness, or loss of appetite.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The terms "effective amount" or "therapeutically effective amount" refer to an amount sufficient to effect beneficial or desirable biological and/or clinical results. In some embodiments, the "effective amount" is an amount able to inhibit viral infectivity by at least 50% or more, preferably by at least 75% or more, more preferably by at least 90% or more.

Suitable amounts of $CaCl_2$) or other soluble Ca++ salt for preparing compositions comprising the soluble truncated peptide include from about 2 mM to about 10 mM, preferably about 3 mM. Other suitable ranges in between are contemplated, including for example, 2 mM, 3 mM, 4 mM, 5 mM, 6 mM, 7 mM, 8 mM, 9 mM and 10 mM. An in vitro assay for testing anti-viral agents The soluble truncated peptides of CDHR3 can be used in assays for testing agents for anti-viral activity. Suitable in vitro assay for testing an agent for anti-viral activity against rhinovirus C are contemplated herein. In one embodiment, the assay comprising the steps of: (a) contacting the agent with the soluble truncated peptide of CDHR3; and (b) assaying the ability of the agent to disrupt binding of the soluble peptide to the virus. Some embodiments, further include the step of (c) incubating rhinovirus pre-incubated with the truncated peptide and the agent with host cells, and measuring the infectivity of the rhinovirus in the host cell. Suitable methods for testing inhibition of binding in a pull-down assay include, but are not limited to, for example, 1. a) mix virus+agent+soluble truncated peptide; b) then pull-down to test disruption virus-peptide binding
2. a) mix virus+agent; b) then test agent inhibition of virus binding to soluble truncated peptide
3. a) mix agent with soluble truncated peptide; b) then test agent inhibition of soluble truncated peptide to bind virus.

The soluble truncated peptides described herein are contemplated to be used in high-throughput screening methods for screening compounds and agents for anti-viral activity. Suitable methods are known in the art and can incorporate the novel soluble truncated peptides described herein.

In some embodiments, the truncated peptide is attached to a solid support, for example, tissue culture plates (including, but not limited to, 6-well, 12-well, 24-well, 48-well, 96-well, 384-well, etc.), membranes, glass slides or plates, among others.

Drugs or agent can be added to screen for inhibitory effects that disrupt this binding.

In some assays, the ability of the virus to bind to cells and infect cells in the presence of the soluble truncated peptide and test agent are assayed.

In some assays, the ability of the virus to bind cells in the presence of the test agent alone are assayed with soluble truncated peptide as a positive control for infection inhibition.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The invention will be more fully understood upon consideration of the following non-limiting examples.

EXAMPLES

Example 1: CDHR3 Extracellular Domain EC1-3 Mediates Rhinovirus C Interaction with Cells and as Recombinant Derivatives, are Inhibitory to Virus Infection This Example demonstrates that identification and production of soluble truncated recombinant CDHR3 peptides which inhibit rhinovirus C binding to cells and inhibit viral infectivity. As detailed below, specific regions (specifically any construct comprising the 1st domain of CDHR3) are required to provide both the binding to RV-C cells and ability to block viral infectivity. These soluble truncated receptors provide the basis for a new in vitro assay for anti-RV-C drug development therapy.

This Example in part demonstrates that soluble recombinant materials comprising domain 1 (e.g., rEC1), domain 1 and 2 (e.g., rEC1-2), domain 1 and 3(Δ2) (e.g., rEC1+3(Δ2)) or domains 1-3 (e.g., rEC1-3) when properly folded in the presence of Ca++, can recapitulate virus:receptor binding interactions and can inhibit RV-C infection of susceptible cells for at least 4 different virus genotypes.

Figure 8:
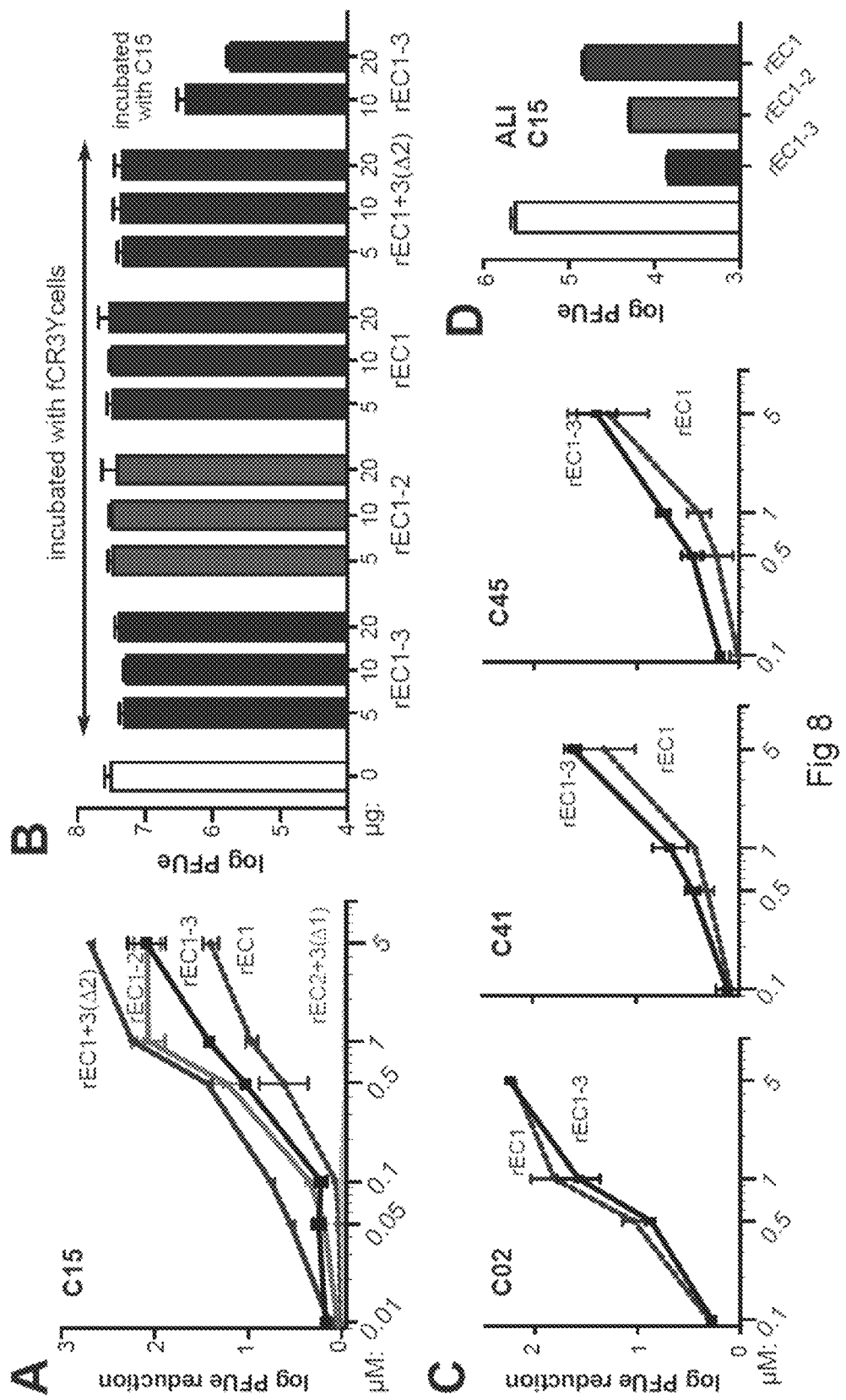
FIG. 8. Inhibition of RV-C infection. (A) C15 virus was preincubated with increasing amounts of the specified recombinant protein (0.05-5 µM) before infection of fCR3Y cells. Cells were washed after attachment and samples collected 24 hpi (triplicate). Virus titers (PFUe) were measured by qPCR. (B) fCR3Y cells were preincubated with or without the specified recombinant protein (5-20 µg) before being washed and infected with C15 virus, or with C15 virus pretreated with rEC1-3 (right lanes). Samples (duplicate) were collected 24 hpi and viral loads measure by qPCR. (C) fCR3Y cells were infected with C02, C41, or C45 virus ($10^7$ PFUe) that had been pretreated with the indicated recombinant protein as in A. Error bars are average of duplicate samples collected 24 hpi. (D) C15 ($10^6$ PFUe) was preincubated (1 h) with or without 1 µM of the specified recombinant protein (in 50 µL) before infection of differentiated nasal epithelial ALI cultures. Single replicate samples were collected 24 hpi for measurement of viral loads (qPCR).
Figure 9:
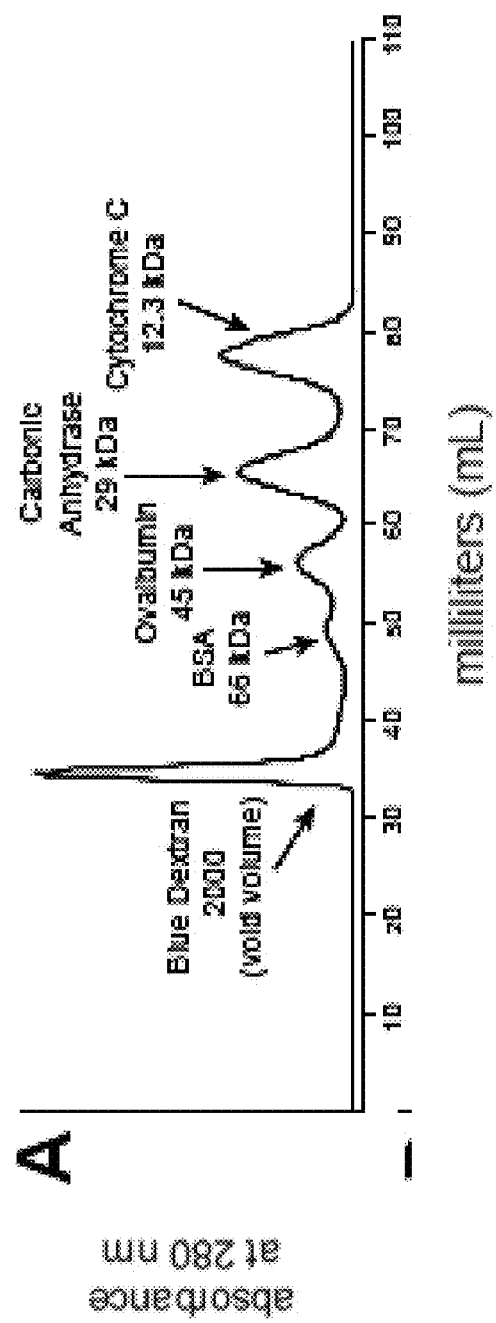
FIG. 9. Gel filtration chromatography of rEC CDHR3 proteins. A) Chromatogram of Gel-Filtration standards: Blue Dextran 2000 (1 mg, D4772, Sigma), BSA (0.5 mg, 23209, Thermo Scientific), Ovalbumin (0.8 mg, A7642, Sigma), Carbonic Anhydrase (1 mg, C2273, Sigma), Cytochrome C (1 mg, C7150, Sigma) separated on HiPrep 16/60 Sephacryl 5200 column (GE Healthcare). (B) Chromatograms of the specified refolded rEC CDHR3 protein preparations (0.5-1.5 mg) run on HiPrep 16/60 Sephacryl 5200 column. All standards and samples were run at 1 mL/min in 20 mM Tris (pH 8.0), 137 mM NaCl, and 2 mM $CaCl_2$).
Figure 9:
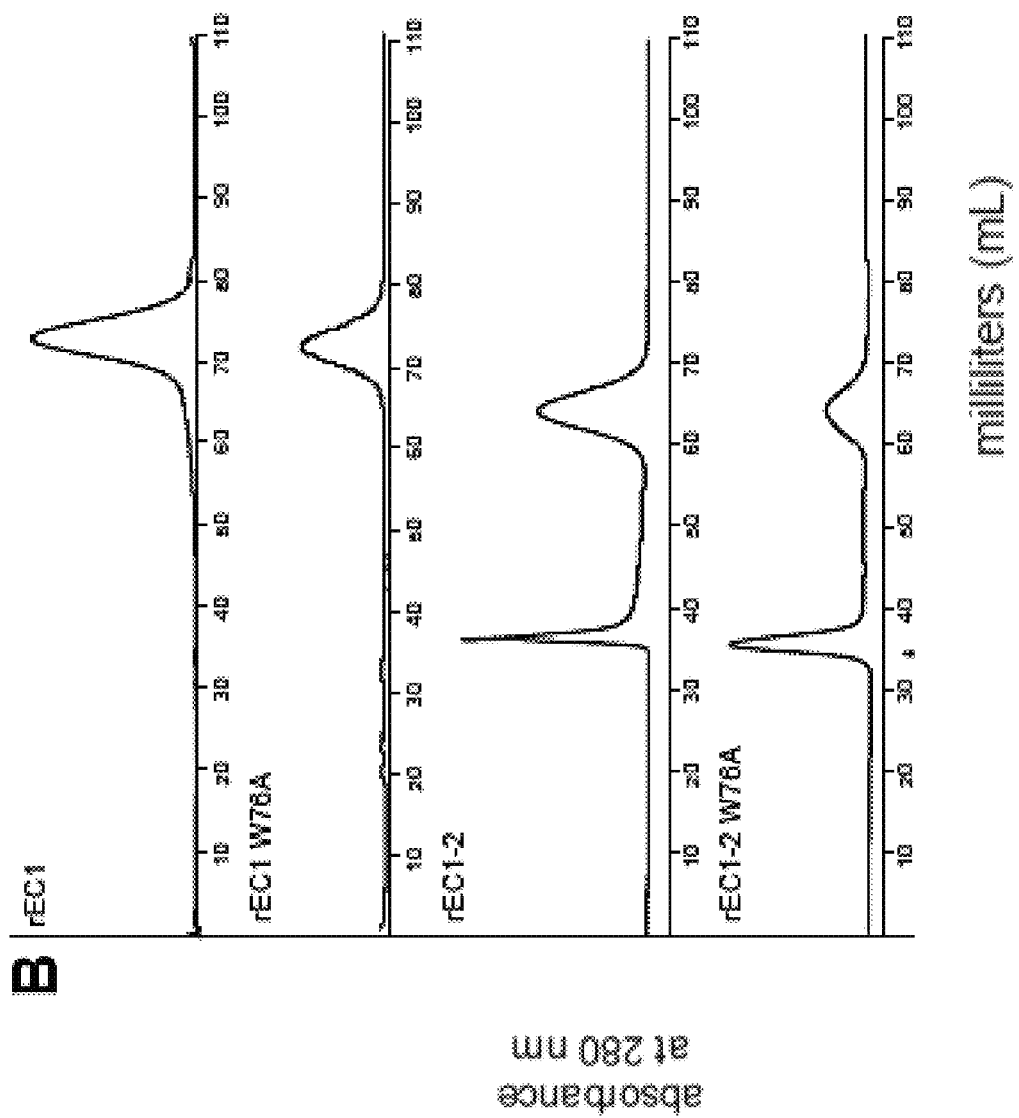
Figure 9:
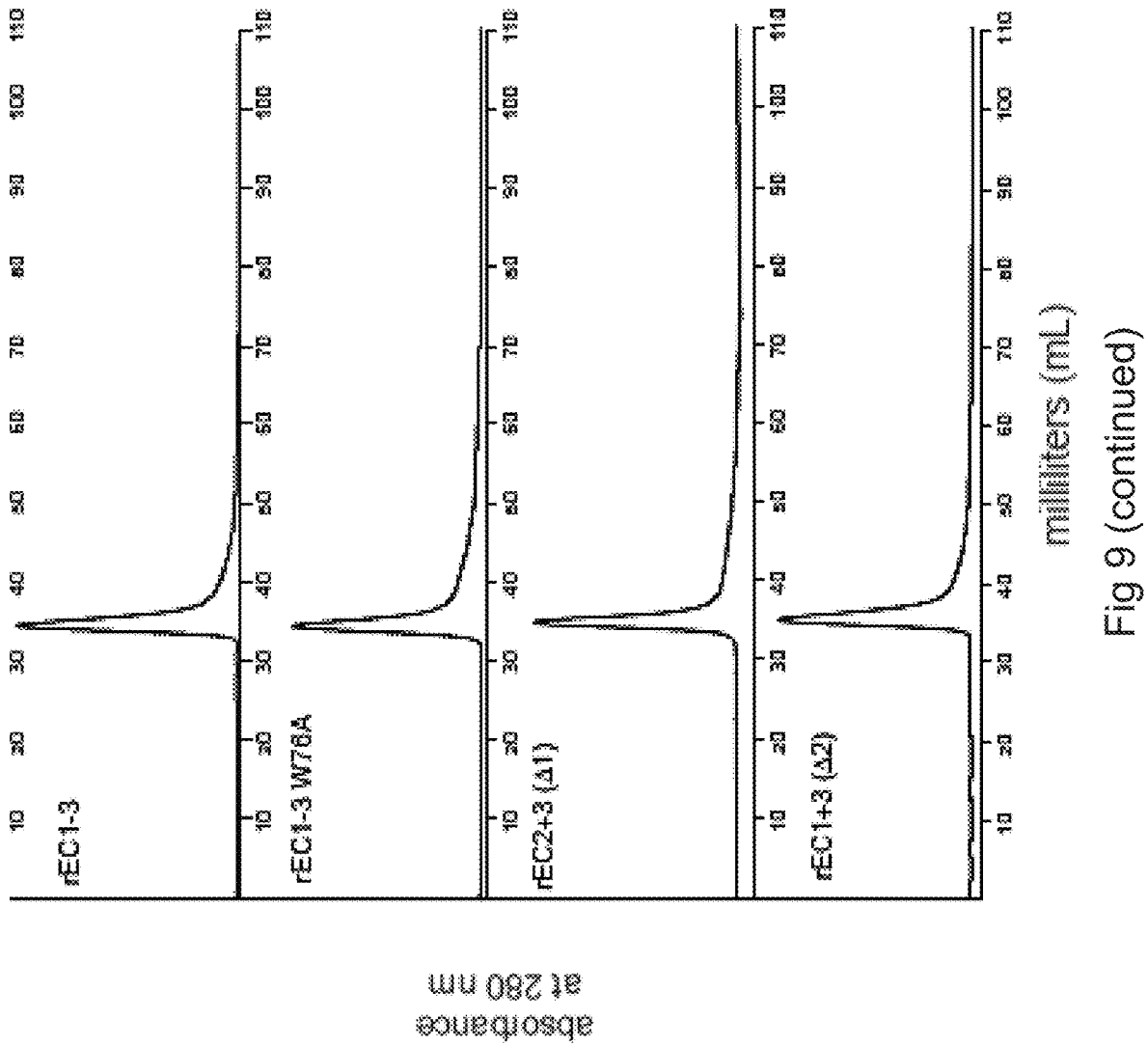

This Example in part further shows that the peptides described herein can be used to reduce viral infection. When pre-incubated with virus before inoculation of cell monolayers, all recombinant proteins containing EC1 inhibited infection in a dose dependent manner (FIG. 8a). Native cadherin proteins commonly form dimers or higher order oligomers on the surfaces of cells (18, 47). Although small amounts of the active proteins were inhibitory, the observed recombinant CDHR3 effects were highest when up to 5 μM of protein were added to each sample ($10^6$ plaque forming unit equivalent (PFUe) of C15). Thus, the mode of observed inhibition could have been due to recombinant protein blocking of CDHR3 receptor sites on each particle, or to direct association of these proteins with the native CDHR3, perhaps through oligomerization, masking the good receptors on the cell surface. The possibilities were distinguished by pre-incubation directly with cells, or directly with virus, before infectivity was tested. Pretreatment of fCR3Y cells with any recombinant protein at any of 3 concentrations, did not protect them from subsequent C15 infection (FIG. 8b). Inhibition required the virus to be pretreated with soluble CDHR3, and that protein needed to encode EC1. The same was true when the tests used additional strains of RV-C (FIG. 8c). Just like C15, C02, C41, and C45 infections were inhibited by soluble CDHR3 rEC1 and rEC1-3, in a dose dependent manner. Finally, we tested the ability of soluble CDHR3 to protect airway epithelial cells, which naturally express CDHR3 and are the primary site of RV infection, by using differentiated nasal epithelial ALI cultures. In a preliminary single-replicate experiment, C15 infection of these cells was also reduced by 1 μM rEC1, rEC1-2, and rEC1-3 (FIG. 8d).

Introduction for Example 1: A defining feature of all cadherins is their distinctive rod-like arrangement of linear tandem-repeat extracellular domains (EC). Collectively or individually, these units mediate the various cis and trans contacts needed for adhesion specificity [26]. Each domain of about 110 amino acids is distinct in sequence, but they typically configure into similar 7-stranded, anti-parallel "Greek key" motifs. The linked repeat units (usually 5) are preceded by a signal sequence and followed with a short transmembrane segment and a cytoplasmic tail. Calcium ions (2 or 3) chelated by multiple acidic residues, are set into each EC junction, and required for relative domain orientation as well as the overall rigidity of the long, slightly curved, rod-like conformations. Homotypic and heterotypic cadherins interact in cis (parallel orientation, same cell) and/or trans (anti-parallel orientation, opposing cell) by reciprocal ionic contacts on their various EC surfaces to provide adhesion functions [27]. The CDHR3 sequence (885 amino acids) encodes six EC repeats with the usual, easily defined amino and carboxyl extensions (FIG. 1). The Y529/C529 dichotomy is in EC5, predicted structurally at the interface with EC6, possibly affecting the calcium stability of that junction [23]. A correlate protein docking model relying on the recent structure resolution of RV-C15a [28] suggested that CDHR3 may interact with this virus exclusively through contacts in the first two domains, assuming a binding orientation that could putatively accommodate receptor monomers or trans-dimers [15]. These predictions, though, are strictly computational. Validation of any model, in lieu of an authentic co-structure, required formal characterization of actual RV-C interactions with multiple native and recombinant formats of CDHR3.

This Example demonstrates the development of relevant biochemical pull-down assays, leading to determination of the minimum forms of CHDH3 capable of direct virus interactions. As soluble recombinant materials, the required protein units, rEC1, rEC1-2, rEC1+3(Δ2) or rEC1-3, when properly folded in the presence of Ca++, could recapitulate virus:receptor binding interactions and could inhibit RV-C infection of susceptible cells for at least 4 different virus genotypes.

Results
Virus Binding to Cell-Expressed CDHR3

RV-C will bind and infect HeLa cells that are transfected or transduced for surface expression of full-length CDHR3 sequences [15]. During transfections however, the exterior protein presentation and therefore formal virus access is dependent on each individual cell's cDNA uptake as well as that sequence's innate display potential (e.g. C529 vs Y529). Transduced cells introduce additional surface variabilities by the very nature of clonal selection. A reproducible assay for virus binding, dependent only on the introduced CDHR3 sequence, was achieved by reacting C15 virus with whole-cell lysates, after transfection or transduction of preferred cDNAs. Except for the CDHR3 glycosylation status (see below) there was no indication in any experiment of virus preference for intra- or extracellular protein pool locales. Indeed, even the predominantly non-surface C529 materials readily interacted with virus, if given the chance as lysate extracts (e.g. see FIG. 2a).

The initial application of this assay tested the overall EC domain requirements (FIG. 1). Immunoprecipitations (IP) with mAbs to the CDHR3 carboxyl His tag (α-His) readily extracted virus if the transfections were with full-length, wild-type (WT) sequences. In agreement with the predicted interaction model, engineered removal of the entire gene segment downstream of EC1-2, including EC3-6, the TM and cytoplasmic domains, produced protein fragments (EC1-2), which remarkably, were still capable of reacting with virus. Consistent with this, internal deletions targeting the precise, short inter-domain linkers that removed just EC1 (i.e. ΔEC1), or just EC2 (i.e. ΔEC2), but not EC3 (i.e.

ΔEC3), created proteins that failed to extract virus. When the IP antibody was switched to α-FLAG, reactive with the amino-proximal sequences, no tested protein co-extracted virus, although all were recognized by the mAb (FIG. 1b). Therefore, while the first two extracellular domains (EC1-2) alone were sufficient to facilitate C15 binding, the process could be interfered with if the chosen IP mAb was sterically close to EC1, or in this case, the 8 amino acids adjacent upstream. A similar distance down-stream of EC2 was apparently not inhibitory if bound by the α-His mAb. Looking more closely at this region, the RV-C binding model suggested that within the EC1-2 sequence, Asn186 (N186) was a likely candidate for a putative sugar ligand contribution. Initially, this was considered of special importance because the C15a virion structure differs from RV-A/B, in that it has an unusual, species-conserved surface pocket, seemingly analogous to the sialic acid interaction site used by enterovirus D68 to mediate that receptor recognition [28,29]. Accordingly, N186 and 5 other amino acids modeled as putative EC1-2 surface features were tested in the lysate-binding assay (FIG. 2). The Asn site, when replaced with Ala or Gln, gave proteins that reacted poorly with virus (reduced to 11% and 19% respectively). The same was true for EC1 domain K43A and EC2 domain R166A changes (to Ala), where binding was also markedly diminished (to 46% and 16%). Other changes though, like F152A and R182A (EC2), and particularly W76A (EC1), if anything, promoted virus IP. The W76A enhancement in particular, was repeatable in multiple experiments and CDHR3 con-texts, usually averaging ~50-80% more virus pull-down than comparable WT sequences. Classical cadherins multimerize by intercalation of an amino-proximal conserved Trp into a hydrophobic pocket of the homotypic or heterotypic partner [30-32]. The CDHR3 W76, while not amino-terminal, is the only tryptophan within EC1-4. The precise quaternary arrangement of full-length CDHR3 in cells (or lysates) is difficult to assay at present. If CDHR3 W76 also participated in multimeric contacts, IP enhancement could well indicate that RV-C prefers lower order monomer or dimer receptor formats. This point was probed further in the design and subsequent testing of bacterial produced recombinant proteins.

CDHR3 Glycosylation

The N186 mutation data fit the binding model's putative expectations that glycosylation at this site might contribute to virus interactions. Almost all classical cadherins are post-translation-ally modified with glycans [31,33-35]. The sequence of CDHR3 predicts 6 possible N-linked sites (FIG. 3). O-linked sites cannot be projected with reliability. FLAG-CDHR3 Y529 protein from transfected HeLa cells was gel-fractionated before and after treatment with PNGaseF. Mass spectrometry then identified the trypsin-dependent peptide differences. PNGaseF reactions deaminate culpable Asn to Asp in the process of removing glycans so the peptide charge relative to sequence and new peak appearance are diagnostic of prior glycosylation [36]. The recovered CDHR3 peptides analyzed this way recapitulated ~80% of the sequence, definitively identifying N186, N384, and N624 as N-linked glycosylation sites. Fragments for N308 and N417 did not respond to enzyme treatment, nor was their amination status changed, indicating that at least for transfection-derived materials, these sites are not glycosylated. The modification status of N257 could not be determined because the appropriate fragment (40 amino acids) was not recovered from either treatment condition.

CDHR3 human protein variants Y529 and C529 from transfected HeLa cells migrate identically during gel fractionation (FIG. 2*a*), as does His529 (H529), a naturally occurring positional mutation found in a few other mammalian genomes like mice and horses [23,24]. Despite a differential surface exposure on intact cells [15] the co-migration of transfected Y529 and C529 was mirrored by equivalent band shifts after PNGaseF treatment of ~8 kDa (FIG. 4*a*) strongly suggestive of similar glycosylation patterns, and consistent with 3-4 N-linked sites. Both full-length sequences (Y529 and C529), in lysate format, bound C15 virus (FIG. 4*a*), presumably through the same EC1-2 contacts. Surprisingly though, PNGaseF treatment did not affect this process. De-glycosylation, which certainly removed the N186 modification, did not prevent subsequent virus interactions.

Unlike transfected cells, transduced cells expressing CDHR3 Y529 (fCR3Y) show 2 forms of protein upon Western analyses (FIG. 4*b*). The lower band (~100 kDa) was similar in size to that produced in transfected cells, or from C529 materials in any format (e.g. fCR3C transduced cells or C529 transfection). The upper band (~108 kDa) shifted when treated with neuraminidase indicating it displayed additional post-translational modification(s) involving supplemental sialylation. This shift was unique to CDHR3 Y529 when this protein was expressed constitutively in fCR3Y cells, instead of transiently (i.e. transfections). Sialic acids are frequently added or rearranged at the termini of N- and O-linked oligosaccharides, via α2-3 or α2-6 linkages [37,38]. The extra attachment(s) in Y529 was tested by the addition of biotinylated *Maackia amurensis* lectin II (MAL II) or biotinylated *Sambucus nigra* lectin (SNA), which respectively label proteins carrying α2-3 or α2-6 sialylated moieties. The Y529 upper band, when reacted with SNA-biotin was readily extracted with streptavidin beads, while very little protein was extracted with MAL II-biotin labeling (FIG. 4*c*). Neither lectin extracted the CDHR3 Y529 lower band or any C529 material from the stably transduced cells. Therefore, the standard CDHR3 glycosylations (i.e. at N186, N384, N624) in transduced or transfected cells do not initially terminate in sialic acids, although one or more glycan branch termini, and perhaps as many as 20 (by estimated molecular weight), subsequently become sialylated by α2-6 linkages, when the Y529 sequence is transduced into cells. The extra sialic acid modifications in Y529 transduced cells are surface dependent, because when intact fCR3Y cells were labeled with biotin, the slower migrating, upper form of CDHR3 was observed only in the extracellular (biotin-labeled, bound) protein fraction and not in the intracellular (unlabeled, unbound) fraction (FIG. 4*d*). Still, regardless of these modifications or how they originate, neither PNGaseF nor neuraminidase digestion of any expressed CDHR3 protein variants inhibited C15 binding (FIG. 4*b*). The predicted glycan binding site on the C15a virion surface, apparently does not capture any N-linked or sialic acid glyco-moiety contributed by CDHR3.

Virus Binding to Recombinant CDHR3 Proteins

The lysate binding assays mapped the segments and sequences of CDHR3 required for virus pull-down. In a formal sense though, those experiments could not preclude contributory partner interactions from other lysate components. Full-length CDHR3 proved insoluble when expressed in bacteria and not readily refolded. Accordingly, the next experiments focused on the EC1-3 domains. Like the successful lysate materials, the recombinant proteins were designed with amino-terminal FLAG-tags and carboxyl-terminal His-tags. The first constructions expressed native CDHR3 residues 20-345 (rEC1-3 #). The amino-terminal signal sequence (residues 1-19) was not included because it prevented high-level protein expression in bacteria. Produced this way, >90% of the bacterial inclusion body material was the desired protein, which upon denaturation (urea) and refolding (see Methods) was capable of binding virus (FIG. 5a). These first iterations though, had occasional solubility issues when residue C345, within rEC3-4 linker region, allowed spurious disulfide interactions. Shortening (-5aa) or lengthening (+10aa) the protein beyond this point was not nearly as effective, in terms of the tested virus binding efficiency, as a simple mutation of C345 to A345 within the plasmid backbone (e.g. rEC1-3). This context, after refolding and especially when augmented with an additional W76A mutation, was sufficient and highly effective in IP reactions (i.e. in buffer alone without other exogenous proteins), for purified C15 virus extractions. As with HeLa-produced proteins, W76A changes captured 50-60% more virus than the WT sequence (FIG. 5b). K43A again proved inhibitory (22%), but surprisingly, in this recombinant format, where there was a denaturation and refolding protocol, N186A retained most of its reactivity with virus (85% of WT).

The next plasmid series assayed domain requirements, successively eliminating EC1, EC2 and EC3 (FIG. 5c). The only inactive protein was that lacking EC1 [rEC2+3(Δ1)]. When the first domain was expressed alone or partnered with EC2 and/or with EC3, there was effective virus binding. The EC1 W76A mutation again seemed to improve virus binding whenever EC1 was linked to EC2 (rEC1-2) or to EC2 and EC3 together (rEC1-3), but not when EC1 was expressed by itself. Size exclusion experiments (FIG. 8) with Sephacryl 5200 showed the rEC1 protein ran as single monomer whether or not W76 was mutated, suggesting that W76 may not behave like the characteristic tryptophans of classical cadherins and "strand-swap" to mediate EC1-dependent trans-dimerization. Interestingly though, all proteins containing an EC3 domain [rEC1-3, rEC2+3(Δ1), or rEC1+3(Δ2)] were completely excluded from the Sephacryl filtration and probably of multimeric order. The rEC1-2 WT and W76A proteins showed both monomers and higher order oligomers in these analyses. Since we consistently observed better virus-binding efficiency to rEC1 and rE1-2 (100 and 87%), which are monomers, relative to rEC1-3 or rEC1+3(Δ2) (61% or 68%), which form higher order oligomers, it is probable that the virus may prefer to bind monomers of CDHR3 when interacting with cells, too.

The virus captured in these assays was not by weak interactions, because for EC1 containing proteins, it resisted disruption with 500 mM salt (FIG. 5d). Collectively, the results show that a direct interaction between purified virus and purified CDHR3 protein fragments does not require exogenous components, including glycosylation, and further suggest this binding is primarily mediated by the EC1 domain. N186 in EC2, and in fact, the whole EC2 domain itself, were not apparent contact requirements, but K43 (in EC1) undoubtedly plays a participating role.

Figure 6:
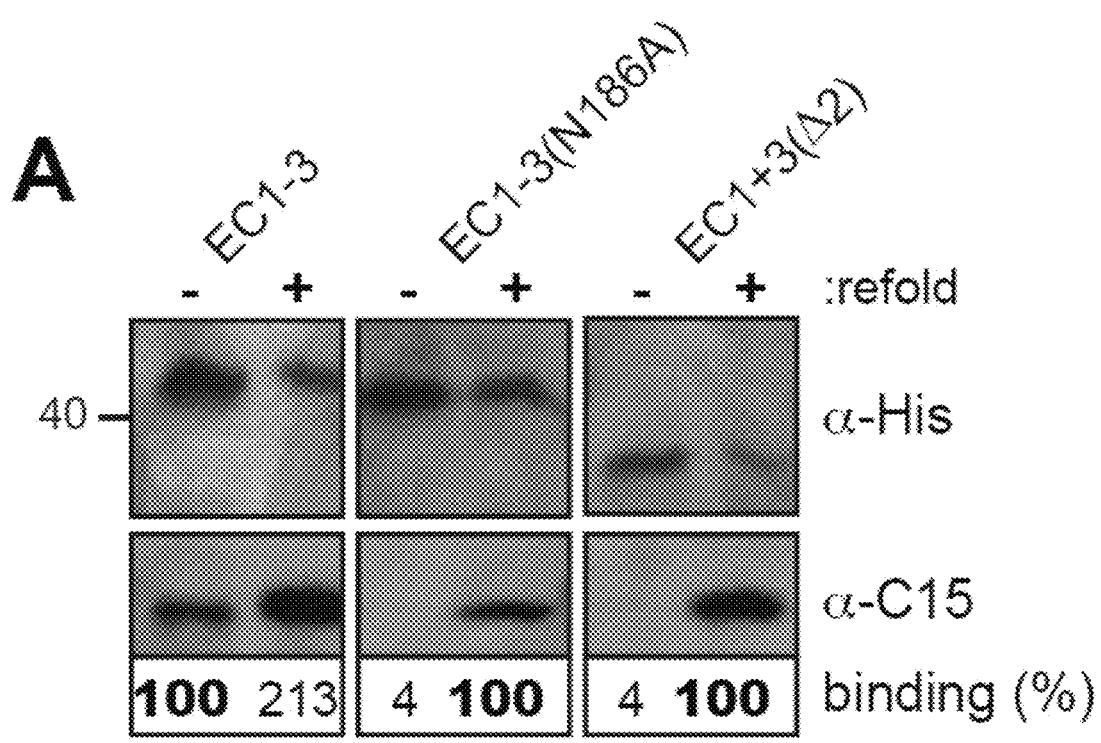
FIG. 6. Misfolding of EC2. Lysates from HeLa cells transfected with cDNAs (B) as in FIG. 1 were extracted with α-His mAb by IP to recover CDHR3 materials. (A) The recovered protein was refold (+) or not (−) according to the refolding protocol in Methods, then reacted with C15 virus. Immunoprecipitation and protein detection were with α-His mAb. Binding % for each protein pair is relative to the pixel count (Total Lab 100) of observed C15 signals normalized to the α-His protein levels (bold face).
Figure 6:
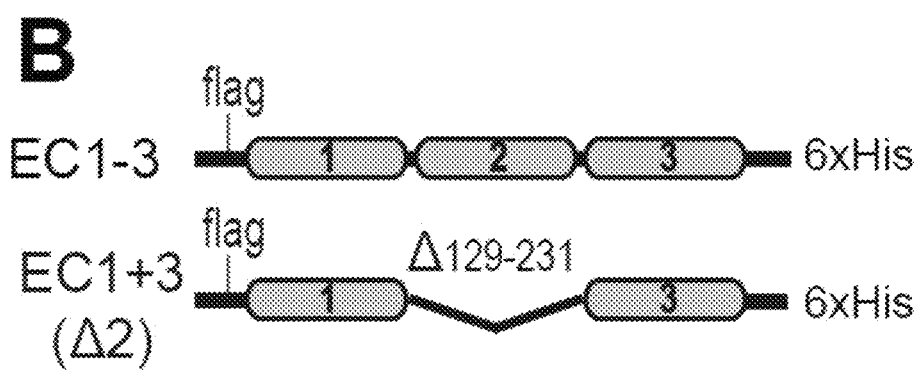

To resolve why prokaryotic (bacteria) and eukaryotic (transfections) expressed proteins showed apparently different virus interaction requirements for the EC2 domain and for N186, transfection plasmids encoding EC1-3 (N186 or N186A), and EC1+3(Δ2), were introduce into HeLa cells (FIG. 6b). The expressed proteins, extracted and recovered from cell lysates via their C-terminal His tags were reacted with C15 virus before and after a denaturation and refolding step, identical to that used for the bacterial materials. Refolding not only rejuvenated the EC1-3 protein (to 213%), it gave new activity to both other cell-expressed sequences. The ΔEC2 deletion, the N186A mutation, and presumably also R166A, as transfected lysates were inactive in these short contexts, and likely also in their full-length contexts (FIG. 1) because they were somehow improperly configured. Allowed to refold, they then bound virus. The slight migration shift (~2 kDa) between EC1-3 with and without N186A is that expected if these proteins differed by a single glycosylation unit. Therefore, in HeLa cells, the N186 glycan linkage may be required for proper domain folding.

A Requirement for Calcium

Figure 7:
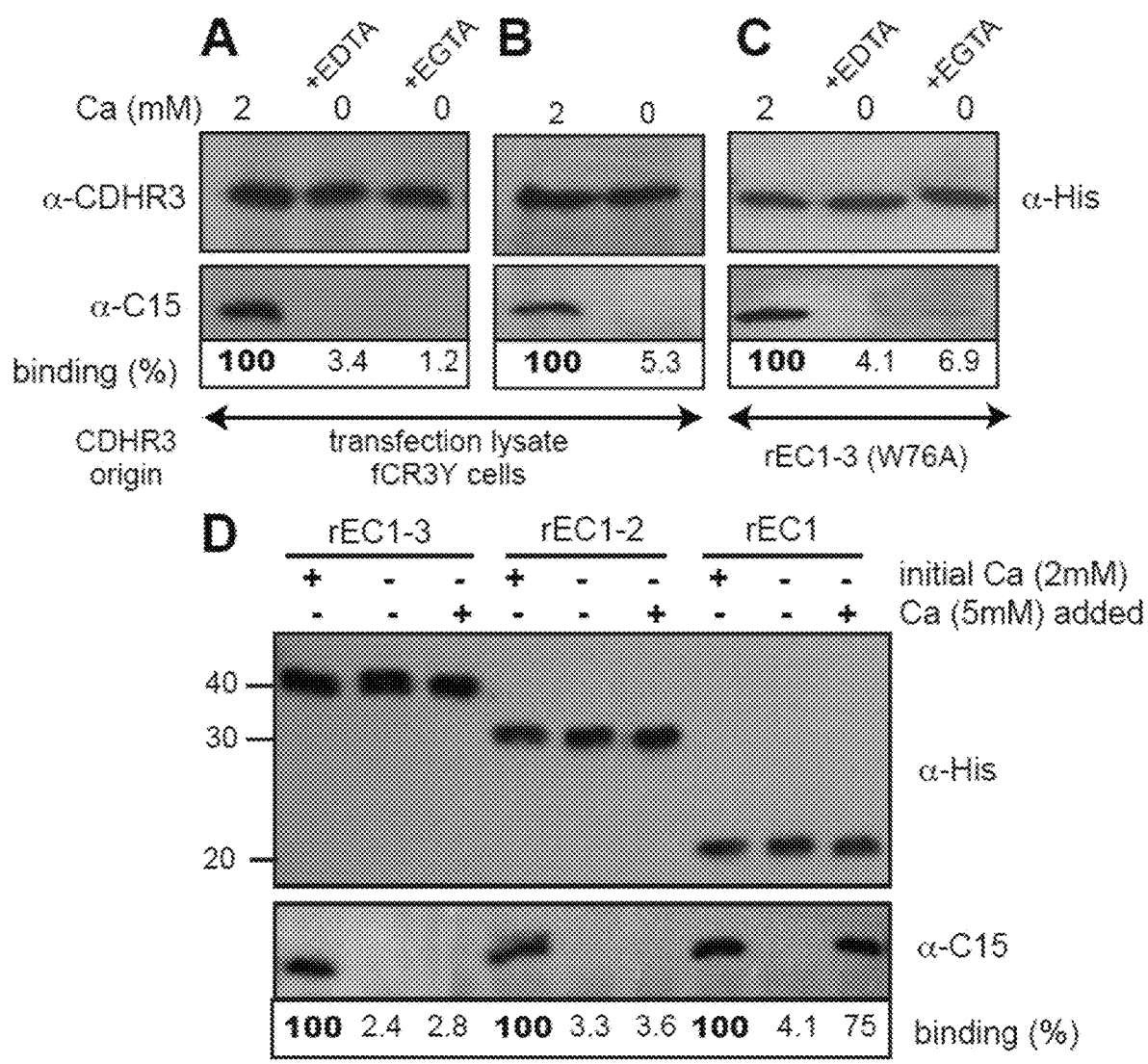
FIG. 7. Dependence of CDHR3 and C15 binding on calcium. Lysates transfected with cDNAs encoding Y529 CDHR3 protein were reacted with C15 virus in buffer with 2 mM calcium, 2 mM EDTA or EGTA (A), or in calcium-free buffer (B) and immunoprecipitated with an α-CDHR3 mAb reactive with the cytoplasmic domain. (C) Purified rEC1-3 protein (100 pmol) was reacted with C15 virus in buffer with 2 mM $CaCl_2$) or 2 mM EDTA or EGTA. (D) rEC1-3, rEC1-2, and rEC1 (100 pmol) protein were first reacted with C15 virus in buffer with or without 2 mM $CaCl_2$) for 1 h at 25 and then incubated another 2 hrs following the addition of 5 mM $CaCl_2$) to designated samples. Immunoprecipitation was with an α-His mAb. Each panel (ABCD) is a separate experiment. Binding % is the observed C15 signal pixel count normalized to the CDHR3 protein (α-His) signal in the panel above (Total Lab 100) relative to positive control (100) in each unit.

The rod-like arrangement of EC domains in classical cadherins is dependent upon calcium binding to multiple acidic clusters at the inter-domain junctions. Removal of calcium causes the proteins to collapse into more condensed structures [31,39,40] and can also affect the oligomerization status when the domains no longer orient properly [41,42]. The CDHR3 structure model predicts analogous acidic clusters at each EC junction [23], but modeling cannot accurately anticipate the exact ion placement or count. In the lysate assay with full-length HeLa-produced CDHR3, the addition of EDTA or EGTA reduced the virus binding to background levels (FIG. 7a). Remarkably, the same effect was achieved by simply diluting the lysate into a buffer lacking calcium (FIG. 7b). This was also observed with recombinant proteins, in that EDTA, EGTA (FIG. 7c) or simple omission of calcium (FIG. 7d, "0 initial") prevented virus extraction by IP. This suggests that one or more of the required ions must be able to diffuse from the EC junction (s), leading to a conformational change in the protein, or its oligomeric state, as required by the virus. When E-cadherin, is depleted of calcium, the protein collapse is reversible [39]. When calcium was added back (for 2 hrs) to soluble rEC1-3 or rEC1-2 that had been diluted into a calcium-free buffer, these proteins still could not bind C15 (FIG. 7d). However, virus binding to rEC1 could be restored upon re-addition of calcium. Likely, the diffusible, stabilizing calcium(s), normally at the interface of EC1 and EC2 can be rebound if EC1 is a monomer, and not linked to EC2. The calcium site must become sterically impaired by depletion-induced conformational changes at this junction when EC1 is linked to EC2 (or EC3).

Recombinant CDHR3 Inhibition of RV-C Infection

Soluble ICAM-1 and LDLR materials can bind their appropriate RV-A and RV-B isolates to inhibit virus infection of susceptible cells [43-45]. The soluble recombinant CDHR3 protein panel was tested for its ability to inhibit C15 infection of stably transduced fCR3Y cells. When pre-incubated with virus before inoculation of cell monolayers, all recombinant proteins containing EC1 inhibited infection in a dose dependent manner (FIG. 8a). Native cadherin proteins commonly form dimers or higher order oligomers on the surfaces of cells [18,46]. Although small amounts of the active proteins were inhibitory, the observed recombinant CDHR3 effects were highest when up to 5 μM of protein were added to each sample (106 plaque forming unit equivalent (PFUe) of C15). Thus, the mode of observed inhibition could have been due to recombinant protein blocking of CDHR3 receptor sites on each particle, or to direct association of these proteins with the native CDHR3, perhaps through oligomerization, masking the good receptors on the cell surface. The possibilities were distinguished by pre-incubation directly with cells, or directly with virus, before infectivity was tested. Pretreatment of fCR3Y cells with any recombinant protein at any of 3 concentrations, did not protect them from subsequent C15 infection (FIG. 8b). Inhibition required the virus to be pretreated with soluble CDHR3, and that protein needed to encode EC1. The same was true when the tests used additional strains of RV-C (FIG. 8c). Just like C15, C02, C41, and C45 infections were inhibited by soluble CDHR3 rEC1 and rEC1-3, in a dose dependent manner. Finally, we tested the ability of soluble CDHR3 to protect airway epithelial cells, which naturally express CDHR3 and are the primary site of RV infection, by using differentiated nasal epithelial ALI cultures. In a preliminary single-replicate experiment, C15 infection of these cells was also reduced by 1 µM rEC1, rEC1-2, and rEC1-3 (FIG. 8d).

Discussion

The binding of a virus to accessible external receptor(s) is an initiating step in host cell entry. CDHR3 cell surface display, mediated by the Y529 variant SNP of this gene, is required for optimal RV-C entry into cells [15]. The dominant human allele, encoding C529, shows much lower protein surface expression in transfected cells and consequently poorer cell-binding interactions with virus. For homozygous or heterozygous Y529 human carriers, especially children, there is a correlate higher rate of virus-induced asthma exacerbations [25]. The current study examined three important questions concerning these observations. First, we asked if there might be measurable discrepancies between the Y529 and C529 proteins, in addition to surface display, that could influence virus interactions? Second, if RV-C did bind directly with either or both proteins, could we devise reproducible assays to map the elements of CDHR3 or its glycosylation format that might be required for this interaction? Third, assuming CDHR3 like the ICAM-1 and LDLR receptors of the RV-A and RV-B could be isolated in a cell-free format, would such materials independently react with virus and potentially inhibit infections?

Cadherin proteins share a common architecture in that the tandem repeat EC domains (EC1-6 for CDHR3) assume a rigid, slightly curved elongated structure, anchored like a waving stalk in the cell membrane. The C-proximal cytoplasmic domain does the anchoring. The N-proximal distal domains (e.g. EC1-3) usually confer adhesion properties by mediating dimer formation or higher order arrangements [26]. The linked EC orientations and even the folding of individual EC units depend on multiple calcium ions bound at various Kd, between the EC junctions. The first challenge in examining CDHR3 was to devise a virus-binding assay that was not cell surface dependent. In transfected or stably transduced cells, the intracellular protein pools are frequently much larger than that which is membrane anchored [15]. Clarified cell lysates proved a ready source of assay materials, and we found no CDHR3 sequences, fragments or conditions that required cell anchoring for demonstrable reactivity with virus. Tested this way, C529, Y529 and H529 proteins were equivalently capable of virus IP (FIG. 2a). The H529 sequence was tested as a curiosity because it is one of the only (non-human) variations of the highly conserved ancestral Y529 allele [24].

The basic N-linked glycosylation sites of human C529 and Y529, mapped to N186 (EC2), N384 (EC4), and N624 (EC6). These proteins migrated equivalently on gels by molecular weight, indicating both must undergo similar Golgi transport and modification pathways on the way to the cell surface. But once there, the Y529 abides, and can be labeled with biotin, while the C529 somehow withdraws, or undergoes a faster surface cycling pattern and is not labeled with biotin. In mature, plated stably transduced cells (fCR3Y), the presumed longer surface "hang time" of constitutively expressed protein apparently then permits Y529 to undergo additional multiple sialyations with α2-6 linkages. Transfected cells, even for Y529 do not have detectable amounts of these modifications, perhaps because the signal strength is masked by the much larger cytoplasmic pool created by overexpression, or because Y529 does not have time to fully surface-mature within 24 hrs post-transfection.

Surprisingly, none of these parameters proved relevant to virus binding. Whether the materials were from transfections, transductions, or bacterially produced, virus could be extracted with almost any CDHR3 format, including after de-glycosylation, as long as a properly reconstituted EC1 domain was present. In fact, EC1 alone was sufficient to bind virus (FIG. 5*c*). Initially, a caveat to this was, that when expressed after transfection, ΔEC2, as well as EC2 point mutation derivatives N186A and N186Q also did not react with virus. Yet in a recombinant bacterially-derived format, rEC1+3(Δ2) was entirely active. This dichotomy, quite clearly had its origin in cell-dependent protein folding. During cell expression and Golgi maturation, EC2 and its glycosylation status at N186 must help the native EC1-2 segments fold. The bacterially-produced recombinant proteins (FIG. 5), or similar sequences synthesized in HeLa cells, all presented a virus-acceptable EC1 if they underwent an artificial refolding step through denaturation and dialysis (FIG. 6).

The R166A mutation, also in EC2, models immediately adjacent to the EC1-EC2 junction, a region predicted to have 11 Asp and Glu calcium-chelating residues within 5-9 Å of its location (FIG. 2*b*). Virus binding proved exquisitely sensitive to the presence of calcium, whether the CDHR3 materials were derived from cells or bacteria (FIG. 7). Not only could EDTA or EGTA prevent interactions, a simple dilution into calcium-free buffer had an equivalent effect. This property is characteristic of cadherins. E-cadherin binds 3 calcium ions between the EC1 and EC2 domains, two at 330 μM Kd and a third at a much higher 2 mM Kd, a value close to the extracellular calcium concentration [41,47]. For E-cadherin, calcium depletion and consequent protein unfolding is reversible [39], but this does not appear to be true for CDHR3 because rEC1-3 and rEC1-2 could not adopt a virus-acceptable conformation when calcium was added back after dilution into a calcium-free buffer (FIG. 7*d*). Interestingly, the readdition of calcium did facilitate proper protein refolding of the singular rEC1 protein. Presumably, CDHR3 needs calcium to fold properly, maintain that fold, and at least 1 or more crucial ion(s) at the EC1-2 junction are irreversibly lost by simple diffusion, likely due to conformational changes in EC2 that sterically prohibit proper calcium re-coordination. This point has also been proposed as functionally germane to the C529/Y529 surface display phenotypes [2]. Similar to R166 at the EC1-2 junction, Y529 is part of the EC5-6 junction. If conversion to C529 were to influence the inter-domain calcium binding and the consequent topography of stalk, an improperly configured protein would be withdrawn from the cell surface, as are similar calcium-depleted cadherins in their natural cycle [48,49]. We are currently testing this hypothesis by determining the NMR structures of cadmium-labeled CDHR3 rEC4-6 domains.

An innate property of all cadherins on cell surfaces or in solution is to find dimeric and/or oligomeric partners. Most certainly the EC3 domain of our proteins promotes self-association because, although soluble upon refolding, proteins containing this domain flow directly through a Sephacryl 5200 column and therefore are of dimer or higher order (FIG. 8). There is only one native, internal CDHR3 cysteine disulfide, linking C566 to C592 within EC6 [23], but the rEC1-3 proteins formed spurious, exogenous disulfides upon refolding, unless C345 was mutated. Even with this change, the protein panel of rEC fragments was still capable of self-assembly. We are currently working with several physical sorting and crystallographic techniques to define the exact nature, order and residue contributors of these self-interactions.

Consistent with what is known for other cadherins, we presumed the W76A mutation acts positively by reducing (trans) oligomer states, thereby freeing more EC1 units for productive virus binding. However, the rEC1 protein appears to be monomeric with or without this mutation. While W76 may not mediate EC1-EC1 dimerization like the tryptophans of other cadherins, it could still be involved in inter-protein interactions with other CDHR3 EC domains.

Alternatively, W76 may lie within or near the virus-contact interface, and elimination of the bulky aromatic side chain may allow tighter virus binding. Ongoing (NMR and cryoEM) structural studies with rCDHR3 proteins should provide some insight on the positive effects we observe for the W76A mutant.

When the panel of recombinant proteins was tested in infectivity inhibition assays, all inhibited virus replication in fCR3Y cells in a dose-dependent manner except rEC2+3 (Δ1) (FIG. 8*a*), which also could not IP virus. We have initiated a collaborative cryoEM determination of the C15 virus complexed with rEC1-3 (with W76A) and rEC1. It will take time for those data collections to achieve sufficient resolution, although we expect they will confirm the protein interactions and format predictions described here. Our original computational docking model suggested elements of both EC1 and EC2, including an N186 glycan, made virus contact [28]. We now know only the EC1 part of this prediction is true. It is more likely that dimers of CDHR3, probably mediated by EC3 cis interactions, present dual EC1 domains to the virus. The unique EC1 contacts, perhaps including K43, are the primary determinants.

EC2 is not required, nor is its glycosylation, except perhaps to help the protein fold properly. Apparently, soluble recombinant proteins contributed in this format are sufficient to inhibit infection of stably transduced fCR3Y HeLa and differentiated nasal epithelial ALI cultures. The observed inhibition phenomenon was common to 4 tested genotypes of virus, indicating that all RV-C virions likely share the same receptor landing pad and would respond to these soluble recombinant CDHR3 sequences in a similar manner. We believe these new reagents have great potential utility in RV-C research as useful tools for investigating CDHR3 biology and function, possibly with future antiviral applications.

Materials and Methods

Eukaryotic Expression Plasmids and Transfections

Plasmids for transient eukaryotic expression of FLAG-tag-CDHR3 C529 and Y529 variants (pCDHR3-FLAG-0529 and pCDHR3-FLAG-Y529), which have a FLAG-tag (DYKDDDDK) (SEQ ID NO: 35) inserted between the CDHR3 signal sequence (residues 1-19) and its EC1 (residue 20), were previously described [15]. The protein numbering system is from GenBank: AIC58018. Additional plasmids encoding single point mutations (K43A, W76A, F152A, R166A, R182A, N186A, N186Q and Y529H) were engineered by two-step PCR into the pCDHR3-FLAG-Y529 plasmid. Analogous units for the expression of various FLAG-tag CDHR3 EC deletion mutants, which included additional carboxy-terminal 6×His tags, were engineered within pHLsec vectors (generously provided by Yue Liu, Michael Rossmann) based on pLEXm plasmid backbones [50]. Pilot experiments indicated that when this vector's innate secretory sequence was linked to the native CDHR3 signal sequence, protein expression was inhibited in transfected cells. Therefore, the 5' regions of the CDHR3 EC deletion sequences, encoded only the native signal sequence and its inserted FLAG-tag, as engineered into pHLsec vector backbones between BamHI and KpnI restriction sites. pHL-FLAG-CDHR3-His constructs included: WT (CDHR3 residues 1-885, Y529), ΔEC1 (1-885, Δ27-124), ΔEC2 (1-885, Δ129-231), ΔEC3 (1-885, Δ230-334), EC1-6 (1-689), EC1-3 (1-345), EC1-2 (1-237). Transfection protocols used 3 μg cDNA reacted with lipofectamine 2000 (3 μL, Invitrogen) in Opti-MEM media (Invitrogen) according to manufacturer's recommendations, and plated HeLa cells (ATCC CRL-1958 in Eagle's medium, 10% NBCS; 6-well dishes; 37° C.) grown to 80% confluence. The cells were incubated 24 h (37° C. under 5% C02) before collection, lysis and immunoprecipitation assays.

Transformed Cell Lines

Amplicons containing the C529 and Y529 FLAG-tagged variants of CDHR3 were amplified by PCR from pCDHR3-FLAG cDNAs and then ligated into MIGR1-based IRES-neo retroviral plasmids (NG) which express neomycin resistance [51,52]. Viral vector generation required 293T cell transfection with pNG-FLAG-CDHR3 plasmids (4 μg), pMDGag-Pol (4 μg, packaging plasmid), and a vesicular stomatitis virus G protein-encoding (VSV-G) envelope plasmid (2 μg) in 500 μL of Opti-MEM with 20 μL of polyethylenimine. The transfection medium was replaced 12 h post-transfection, then subsequently harvested and filtered (0.45 μm, at 48 h). After infection of HeLa cells (ATCC CRL-1958) with this material by spinoculation [53] and incubation for genome integration, stably transformed cells were selected with G418 (400 μg/mL, Geneticin) and cloned. The cells were maintained in suspension culture [37° C.; Eagle's medium, 10% newborn calf serum (NBCS), 2% fetal bovine serum (FBS) under 5% CO2]. The final transduced HeLa cell lines expressing full-length C529 and Y529 FLAG-tagged variants of CDHR3 were designated fCR3C and fCR3Y, respectively.

CDHR3 N-Linked Glycosylation

Cells (2×106) transfected with pCDHR3-FLAG-Y529 were lysed in PBS (100 μL, 0.5% SDS and 40 mM DTT) and then heated (10 min, 95° C.). The denatured lysate was diluted 2-fold into PBS and 1% NP40 and then equivalent samples were incubated with or without PNGaseF (1 U, 1 h, 37° C., Sigma F8435). The proteins (25 μL lysates) were fractionated by SDS-PAGE and visualized by Coomassie Brilliant Blue staining. Bands corresponding to glycosylated (~100 kDa) and de-glycosylated (~93 kDa) CDHR3 gel regions were cut out and submitted for analysis to the Mass Spectrometry/Proteomics facility at the University of Wisconsin Biotechnology Center for MS/MS analysis after in-gel trypsin digestion.

Recombinant CDHR3

Bacterial plasmids for the expression of various CDHR3 rEC domains, linked to amino-terminal FLAG-tags and carboxy-terminal 6×His tags, were constructed. The rEC1 segment encoded residues 20-130, rEC1-2 encoded residues 20-237, rEC1-3 encoded residues 20-345, rEC2+3(Δ1) encoded residues 20-345 (Δ27-124), rEC1+3(Δ2) encoded residues 20-345 (Δ129-231), rEC1-3(+10aa) encoded residues 20-355, and rEC1-3(-5aa) encoded residues 20-340. These units were amplified by PCR from the pHL-FLAG-CDHR3-His cDNAs described above and then ligated into pET11a vectors between the NheI and BamHI restriction sites. To prevent spurious disulfide formation, most plasmids encoding EC3 segments had a point mutation converting Cys345 to Ala345 (C345A). Additional point mutations were engineered by standard, primer-directed two-step PCR. *Escherichia coli* BL21(DE3) LysS cells, trans-formed with each plasmid were induced with IPTG (isopropyl-β-d-thio-galactopyranoside) for recombinant protein expression. The cells were collected by centrifugation, resuspended in lysis buffer (20 mM Tris, pH 8.0, 137 mM NaCl, 1% Triton-X100), and sonicated. The majority of recombinant material was insoluble and collected by centrifugation (20,000×g for 45 min at 4° C.). The pellets were washed (1 M NaCl, then 1 M urea, then water) and solubilized (6 M urea, 20 mM Tris, pH 8.0, 137 mM NaCl for 1 h at 25° C. or O/N at 4° C.). After clarification (20,000×g for 45 min at 4° C.), the supernatant of rEC1 and rEC1-2 proteins were purified under denaturing conditions (6 M urea, 20 mM Tris, pH 8.0, 137 mM NaCl) on HisTrap FF columns (GE Healthcare). After elution with 200 mM Imidazole, the proteins were diluted (to 0.1-0.2 mg/mL) in the solubilization buffer (above) supplemented with 3 mM CaCl$_2$) and then dialyzed (4 times, 8-12 hrs each, against 20 mM Tris, pH 8.0, 137 mM NaCl, 3 mM CaCl$_2$), 2 mM β-mercaptoethanol). Proteins containing the EC3 domain [rEC1-3, rEC2+3(Δ1), and rEC1+3(Δ2)] bound poorly to the HisTrap FF columns even under denaturing conditions so the clarified supernatants were diluted and refolded as described above. Refolded proteins were concentrated using Amicon Ultra centrifugal filters.

Viruses

Recombinant RV-C isolates C02, C15, C41, and C45 were produced by transfecting full-length T7 RNA transcripts synthesized in vitro (Ribomax, Promega) from linearized plasmid cDNAs into HeLa cells [54]. The C02 and C45 sequence encoded a D41K substitution in protein 3A, to increase virus replication in these cells. In contrast to the more prolific, HeLa-adapted C15a sequence, these recombinants do not encode a T125K substitution in capsid protein VP1. Therefore, like their parental clinical isolates, they do not bind heparan sulfate and their cell interactions are entirely dependent upon CDHR3 presentation [54]. Virus purification was by centrifugation of cell lysates through 30% sucrose cushions as described [55].

Virus Binding/Immunoprecipitation Assays

CDHR3 proteins expressed in transfected or stably trans-formed HeLa cells (~2×106 cells scraped, collected in PBS, pelleted) were harvested 24 h after transfection or plating. The cells were pelleted (1.5 min at 1500×g), resuspended and then lysed (350 μL, 20 mM Tris, 137 mM NaCl, 2 mM CaCl$_2$), 2 mM PMSF, 1% Triton x-100). The lysates were clarified (16,000×g, 20 min) and then incubated with sucrose purified C15 virus (107 PFUe) and with antibody (0.8 μL, α-CDHR3, HPA011218, Sigma; or 1 μg α-His Tag, HIS.H8, Millipore) overnight at 4° C. before being reacted with protein-G sepharose beads (1 h, 25° C.). When required, glycosylases PNGaseF (1 U, Sigma F8435) or neuraminidase (0.04 U, Sigma 10269611001) were included during the overnight incubations. After reaction and collection, the beads were washed (3×, lysis buffer) and bound proteins eluted with SDS (boiling), before SD S-PAGE fractionation and visualization by Western blot analysis. For experiments with bacterially-expressed materials, the refolded protein samples (100 pmol) were incubated with virus (107 PFUe, 1 h, 25° C.) and with the α-His Tag antibody (350 μL, 20 mM Tris, 137 mM NaCl, 2 mM CaCl$_2$), 1% Triton x-before reactions with protein-G sepharose beads and treatment as above.

Biotinylation Assays

The sialylation status of CDHR3 expressed in fCR3Y or fCR3C was tested by incubating (1 h, 25° C.) cell lysates (~2×106 cells in 300 μL, PBS 1% TritonX-100) with 5 ng biotinylated *Sambucus nigra* lectin (SNA) or *Maackia amurensis* lectin II (MAL II, Vector Labs) before addition to streptavidin beads (1 h, 25° C.). Collected beads were washed (3×PBS) before the bound protein was eluted (in 30 μL 2% SDS, with boiling), fractionated by SD S/PAGE and then visualized by Western blot analysis. Extracellular expression of CDHR3 was examined by treating plated cells (~2×106 per sample) with EZ-Link Sulfo-NHS-Biotin (2 mM, Thermo-Fisher, in PBS for 1 h at 25° C.). The cells were then washed (3×, 50 mM Tris, pH 8.0; 3×PBS), harvested, lysed (300 μL, PBS 1% TritonX-100). The clarified lysates were reacted with streptavidin beads (1 h, 25° C.). The bound samples were processed for protein detection as above.

Western Analyses

After SDS-PAGE resolution, proteins were electro-transferred to polyvinylidene difluoride membranes (Immobilon-P, Millipore). The membranes were blocked (1 h, 10% NFD milk in TBST: 20 mM Tris pH 7.6, 150 mM NaCl, 0.5% Tween20) then incubated with a primary antibody (1% NFD milk in TBST, overnight, 4° C.) before washing (3×TBST) and reaction with an appropriate secondary antibody (1 h, 20° C.). Commercial antibodies included: α-CDHR3 (rabbit Ab HPA011218 IgG, Sigma, 1:2000), α-FLAG (rabbit mAb F2555, IgG, Sigma, 1:2000), α-His Tag, (murine mAb HIS.H8 IgG, Millipore, 1:4000), HRP-conjugated α-mouse IgG (goat Ab A1068, Sigma (1:4000), and HRP-conjugated α-rabbit IgG (goat Ab A0545, Sigma, 1:4000). α-C15 (18C4 and 30C12, 1:5000) are custom murine mAbs (1 mg/mL, GeneScript) raised to the VP1 "finger" peptide sequence [28] characteristically exposed on the surface of this RV-C virion structure. For band visualization, the membranes were rinsed (3×, TBST), incubated (1 min) with enhanced chemiluminescence substrate (GE healthcare) and then exposed to film.

Infection Inhibition Assays

Typically, virus (3×106 PFUe) was incubated (1 h, 25° C.) with or without refolded recombinant CDHR3 protein (0.01 to 5 μM) in binding buffer (100 μL, 20 mM Tris pH 8.0, 137 mM NaCl, 2 mM CaCl$_2$)) before dilution into Eagle's medium (250 μL). Inoculation was onto plated, stably transformed fCR3Y cells. After attachment (30 min at 25° C., 15 min at 34° C.), the cells were washed (2× with PBS) to remove unattached virus and incubated (24 h at 34° C.) before harvest (lysis in 350 RLT buffer, Qiagen) and assessment of virus replication. Alternatively, the cells were directly incubated with recombinant CDHR3 protein (0-20 μg in 100 μL binding buffer, diluted into 250 μL Eagle's medium, 30 min 25° C., then 15 min 34° C.) and then washed (2×, PBS) before being exposed to virus as above. The cells were washed (2× with PBS) to remove unattached virus, before incubation (24 h at 34° C.), harvest and virus measurements. Viral loads (PFUe) were determined by RT-qPCR according to standardized RNA preparations after total RNA extraction from harvested cells (RNeasy Mini kits, Qiagen). The RT-qPCR reactions used Power SYBR Green PCR mix (Life Technologies) and RV-C specific primers as previously described [10]. For experiments with differentiated primary nasal epithelial cells, cells were obtained from nasal turbinates using ASI Rhino-Pro curette (Arlington Scientific) and cultured at air-liquid interface in collagen-coated Transwell polycarbonante inserts as previously described [10,11]. Fully differentiated cultures (2 months old) were washed with PBS and inoculated with C15 virus (106 PFUe) preincubated (1 h, 25° C.) with or without 1 µM recombinant CDHR3 protein (50 µL 20 mM Tris pH 8.0, 137 mM NaCl, 2 mM $CaCl_2$)). After attachment (30 min at 25° C., 15 min at 34° C.), the cells were washed (3× with PBS) to remove unattached input virus and incubated (24 h at 34° C.) before harvest for assessment of virus replication as described above.

REFERENCES

1. Gern J E (2010) The ABCs of rhinoviruses, wheezing, and asthma. J Virol 84: 7418-7426.
2. Jartti T, Lehtinen P, Vuorinen T, Ruuskanen O (2009) Bronchiolitis: age and previous wheezing episodes are linked to viral etiology and atopic characteristics. Pediatr Infect Dis J 28: 311-317.
3. Juven T, Mertsola M, Waris M, Leinonen M, Meurman O, et al. (2000) Etiology of community-acquired pneumonia in 254 hospitalized children. Pediatr Infect Dis J 19: 293-298. PMID: 10783017
4. Lee W-M, Lemanske R F, Evans M D, Vang F, Pappas T, et al. (2012) Human rhinovirus species and season of infection determine illness severity. Am J Respir Crit Care Med 186: 886-891.
5. Turunen R, Jartti T, Bochkov Y A, Gern J, Vuorinen T (2016) Rhinovirus species and clinical characteristics in the first wheezing episode in children. J Med Virol 88: 2059-2068.
6. Bizzintino J, Lee W-M, Laing I A, Vang F, Pappas T, et al. (2011) Association between human rhinovirus C and severity of acute asthma in children. Eur Respir J 37: 1037-1042.
7. Cox D W, Bizzintino J, Ferrari G, Khoo S-K, Zhang G, et al. (2013) Human rhinovirus species C infection in young children with acute wheeze is associated with increased acute reparatory hospital admissions. Am J Respir Crit Care Med 188: 1358-1364.
8. McErlean P, Shackelton L A, Lambert S B, Nissen M D, Sloots T P, et al. (2007) Characterisation of a newly identified human rhinovirus, HRV-QPM, discovered in infants with bronchiolitis. J Clin Virol 39: 67-75.
9. Dominguez S R, Briese T, Palacios G, Hui J, Villari J, et al. (2008) Multiplex MassTag PCR for respiratory pathogens in pediatric nasopharyngeal washes by conventional diagnostic testing shows a high prevalence of viruses belonging to a newly recognized rhinovirus Glade. J Clin Virol 43: 219-222.
10. Bochkov Y A, Palmenberg A C, Lee W-M, Rathe J A, Amineva S P, et al. (2011) Molecular modeling, organ culture and reverse genetics for a newly identified human rhinovirus C. Nature Medicine 17: 627-632.
11. Ashraf S, Brockman-Schneider R, Bochkov Y A, Pasic T R, Gern J E (2013) Biological characteristics and propagation of human rhinovirus-C in differentiated sinus epithelial cells. Virology 436: 143-149.
12. Hao W, Bernard K, Patel N, Ulbrandt N, Feng H, et al. (2012) Infection and propagation of human rhino-virus C in human airway epithelial cells. J Virol 86: 24-32.
13. Greve J M, Davis G, Meyer A M, Forte C P, Yost S C, et al. (1989) The major human rhinovirus receptor is ICAM-1. Cell 56: 839-847. PMID: 2538243
14. Hofer F, Gruenberger M, Kowalski H, Machat H, Huettinger E, et al. (1994) Members of the low density lipoprotein receptor family mediate cell entry of a minor-group common cold virus. Proc Natl Acad Sci USA 91: 1839-1842. PMID: 8127891
15. Bochkov Y A, Watters K, Ashraf S, Griggs T F, Devries M K, et al. (2015) Cadherin-related family member 3, a childhood asthma susceptibility gene product, mediates rhinovirus C binding and replication. Proc Natl Acad Sci USA 112: 5485-5490.
16. Wheelock M J, Johnson K R (2003) Cadherin-mediated cellular signaling. Curr Op Cell Biol 15: 509-514. PMID: 14519384
17. Nejsum L N, Nelson J (2007) A molecular mechanism directly linking E-cadherin adhesion to initiation of epithelial cell surface polarity. J Cel Biol 178: 323-335.
18. Niessen C M, Leckband D, Yap A S (2011) Tissue organization by cadherin adhesion molecules: Dynamic molecular and cellular mechanisms of morphogenetic gegulation. Physiol Rev 91: 691-731.
19. Halbleib J M, Nelson W I (2006) Cadherins in development: cell adhesion, sorting, and tissue morphogenesis. Genes and Dev 20: 3199-3214.
20. Yanai I, Benjamin H, Shmoish M, Chalifa-Caspi V, Shklar M, et al. (2005) Genome-wide midrange transcription profiles reveal expression level relationships in human tissue specification. Bioinformatics 21: 650-659.
21. Griggs T F, Bochkov Y A, Basnet S, Pasic T R, Brockman-Schneider R A, et al. (2017) Rhinovirus C targets ciliated airway epithelial cells. Respiratory Research 18: 84.
22. Bonnelykke K, Sleiman P, Nielsen K, Kreiner-Moller E, Mercader J M, et al. (2014) A genome-wide association study identifies CDHR3 as a susceptibility locus for early childhood asthma with severe exacerbations. Nature Genetics 46: 51-55.
23. Palmenberg A C (2017) Rhinovirus C, asthma, and cell surface expression of virus receptor, CDHR3. J Virol 91.
24. O'Neill M B, Laval G, Teixeira J C, Palmenberg A, Pepperell C S (2017) Evolutionary genetics of a disease susceptibility locus in CDHR3. bioRxiv.
25. Bonnelykke K, Coleman A T, Evans M D, Thorsen J, Waage J, et al. (2018) Cadherin-related family member 3 genetics and rhinovirus C respiratory illnesses. Am J Respir Crit Care Med 197: 589-594.
26. Shapiro L, Weis W I (2009) Structure and biochemistry of Cadherins and Catenins. Cold Spring Harb Perspect Biol.
27. Perez T D, Nelson W I (2004) Cadherin adhesion: mechanism and molecular interactions. Handbook of Experimental Pharmacology 165: 3-21.
28. Liu Y, Hill M G, Klose T, Chen Z, Watters K E, et al. (2016) Atomic structure of a rhinovirus C, a virus species linked to severe childhood asthma. Proc Nat Acad Sci USA 113: 8997-9002.
29. Liu Y, Sheng J, Baggen J, Meng G, Xiao C, et al. (2015) Sialic acid-dependent cell entry of human enterovirus D68. Nature Communications.
30. Shapiro L, Fannon A M, Kwong P D, Thompson A, Lehmann M S, et al. (1995) Structural basis of cell-cell adhesion by cadherins. Nature 374: 327-337.
31. Boggon T J, Murray J, Chappuis-Flament S, Wong E, Gumbiner B M, et al. (2002) C-cadherin ectodomain structure and implications for cell adhesion mechanisms. Science 296: 1308-1313.
32. Troyanovsky R B, Sokolov E, Troyanovsky S M (2003) Adhesisve and lateral E-cadherin dimers are mediated by the same interface. Mol and Cell Biol 23: 7965-7972.
33. Langer M D, Guo H, Shashikanth N, Pierce J M, Leckband D (2012) N-glycosylation alters cadherin-mediated intercellular binding kinetics. J Cell Sci 125: 2478-2485.

34. Liwosz A, Lei T, Kukuruzinska M A (2006) N-glycosylation affects the molecular organization and stability of E-cadherin junctions. J Biol Chem 281: 23138-23149.

35. Guo H, Johnson H, Randolph M, Pierce M (2009) Regulation of homotypic cell-cell adhesion by branched N-glycosylation of N-cadherin extracellular EC2 and EC3 domains. J Biol Chem 284: 34986-34997.

36. Plummer T H J, Elder J H, Alexander S, Phelan A W, Tarentino A L (1984) Demonstration of peptide:N-glycosidase F activity in endo-beta-N-acetylglucosaminidase F preparations. J Biol Chem 259: 10700-10704. PMID: 6206060

37. Suzuki Y (2004) Sialobiology of influenza molecular mechanisms of host range variation of influenza viruses. Biological and Pharmaceutical Bulletin 28: 399-408.

38. Chen X, Varki A (2011) Advances in the biology and chemistry of sialic acids. ACS Chemical Biology 5: 163-176.

39. Pokutta S, Herrenknecht K, Kemler R, Engel J (1994) Conformational changes of the recombiant extracellular domain of E-cadherin upon calcium binding. Eur J Biochem 223: 1019-1026. PMID: 8055942

40. Nagar B, Overduin M, Ikura M, Rini J M (1996) Structural basis of calcium-induced E-cadherin rigidification and dimerization. Nature 380: 360-364.

41. Koch A W, Pokutta S, Lustig A, Engel J (1997) Calcium binding and homoassociation of E-cadherin domains. Biochemistry 36: 7697-7705.

42. Haussinger D, Ahrens T, Sass H-J, Pertz O, Engel J, et al. (2002) Calcium-dependent homoassociation of E-cadherin by NMR Spectroscopy: changes in mobility, conformation and mapping of contact regions. J Mol Biol 324: 823-839. PMID: 12460580

43. Last-Barney K, Marlin S D, McNally E J, Cahill C, Jeanfavre D, et al. (1991) Detection of major group rhinoviruses by soluble intercellular adhesion molecule-1 (sICAM-1). Journal of Virological Methods 35: 255-264.

44. Greve J M, Forte C P, Marlor C W, Meyer A M, Hoover-Litty H, et al. (1991) Mechanisms of receptor-mediated rhinovirus neutralization defined by two soluble forms of ICAM-1. J Virol 65: 6015-6023. PMID: 1681115

45. Marlovits T C, Abrahamsberg G, Blaas D (1998) Very-low-density lipoprotein receptor fragment shed from HeLa cells inhibits human rhinovirus infection. J Virol 72: 10246-10250. PMID: 9811769

46. Harrison O J, Jin X, Hong S, Bahna F, Ahlsen G, et al. (2011) The extracellular architecture of adherens junctions revealed by crystal structures of type 1 cadherins. Struct 19: 244-256.

47. Quist A P, Rhee S K, Lin H, Lal R (2000) Physiological role of gap-junctional hemichannels. Extracellular calcium-dependent isosmotic volume regulation. J Cel Biol 148: 1063-1074.

48. Kartenbeck J, Schmelz M, Franke W W, Geiger B (1991) Endocytosis of junctional cadherins in bovine kidney epithelial (MDBK) cells cultured in low Ca2+ ion medium. J Cel Biol 113: 881-892.

49. Mattey D L, Garrod D R (1986) Splitting and internalization of the desmosomes of cultured kidney epithelial cells by reduction in calcium concentration. J Cell Sci 85: 113-124. PMID: 3793787

50. Aricescu A R, Lu W, Jones E Y (2006) A time- and cost-efficient system for high-level protein production in mammalian cells. Acta Crystallogr D Biol Crystallogr 62: 1243-1250.

51. Sheehy A M, Gaddis N C, Choi J D, Malim M H (2002) Isolation of a human gene that inhibits HIV-1 infection as is supressed by the viral Vif protein. Nature 418: 646-650.

52. Gallois-Montbrun S, Kramer B, Swanson C M, Byers H, Lynham S, et al. (2007) Antiviral protein APO-BEC3G localizes to ribonucleoprotein complexes found in P bodies and stress granules. J Virol 81: 2165-2178.

53. O'Doherty U, Swiggard W J, Malim M H (2000) Human immunodeficiency virus type 1 spinoculation enhances infection through virus binding. J Virol 74: 10074-10080. PMID: 11024136

54. Bochkov Y A, Watters K E, Basnet S, Sijapati S, Hill M G, et al. (2016) Mutations in VP1 and 3A proteins improve binding and replication of rhinovirus C15 in HeLa-E8 cells. Virology 499: 350-360.

55. Griggs T F, Bochkov Y A, Nakagome K, Palmenberg A C, Gern J E (2015) Production, purification, and capsid stability of rhinovirus C types. J Virol Methods 217: 18-23.

56. Kim D, Chivian D, Baker D (2004) Protein structure prediction and analysis using the Robetta server. Nucleic Acid Res 32: 526-531.

Each publication, patent, and patent publication cited in this disclosure (including any listed in Exhibit A) is incorporated in reference herein in its entirety. The present invention is not intended to be limited to the foregoing examples, but encompasses all such modifications and variations as come within the scope of the appended claims.

Sequence Listing Statement

The application includes the sequence listing that is concurrently filed in computer readable form. This sequence listing is incorporated by reference herein.

Protein Sequences

SEQ ID NO:1 CDHR3 Synthetic Sequence: Genbank Accession AIC58018 (885 Aa)-Accession KJ900485.1

Bold: domain 1 (SEQ ID NO:2)

Underline: Domain 2 (SEQ ID NO:3)

Bold/italic: Domain 3 (SEQ ID NO:4) with C345 highlighted and underlined

[Domain 1: 26-128, Domain 2: 141-231, Domain 3: 242-341]]

Signal Peptide: aa 1-20

Linker 1 (Aa 21-25), Linker 2 (Aa 129-140), Linker 3 (Aa232-241) and Linker 4 (Aa 342-345 with c-to-a-Mutation, the c is Bold-Italic Below)

1 mqeaiillal lgamsggeal hlillpatgn vaensppgts vhkfsvklsa slspvipgfp 61 qivnsnplte afrvnwlsgt yfevvttgme qldfetgpni fdlqiyvkde vgvtdlqvlt 121 vqvtdvnepp qfqgnlaegl hlyiveranpgfiyqveafdpedtsrniplsyflisppks 181 frmsangtlf stteldfeag hrsfhlivev rdsgglkast elqvnivnln devprftspt 241 rvytvleels pgtivanita edpddegfps hllysittvs kyfminqltg tiqvaqridr 301 dagelrqnpt islevlvkdr pyggqenriq itfivedvnd npatcqkftf simvpertak
361 gtllldlnkf cfdtddseapn nrfnftmpsg vgsgsrflqd pagsgkivli gdldyenpsn
421 laagnkytvi iqvqdvappy yknnvyvyil tspenefpli fdrpsyvfdv serrpartry
481 gqvratdkdl pqssllysis tggaslqypn vfwinpktge lqlvtkvdce ttpiyilriq
541 atnnedtssv tvtvnileen dekpictpns yflalpvdlk vgtniqnfld tctdldsspr
601 sfrysigpgn vnnhftfspn agsnvtrlll tsrfdyaggf dkiwdykllv yvtddnlmsd
661 rkkaealvet gtvtlsikvi phpttiittt prprvtyqvl rknvyspsaw yvpfvitlgs
721 illlgllvyl vvllakaihr hcpcktgknk epltkkgetk taerdvvvet iqmntifdge
781 aidpvtgety efnsktgark wkdpltqmpk wkesshqgaa prrvtagegm gslrsanwee
841 delsgkawae daglgsrneg gklgnpknrn pafmnraypk phpgk

TABLE 1

| Recombinant CDHR3 protein sequences* | |
|---|---|
| FLAG-CDHR3 EC1-His SEQ ID NO: 19 (SEQ ID NO: 20 = italicized: aa 20-130 of SEQ ID NO: 1) | MASDYKDDDDK *LHLILL PATGNVAENSPPGTSVHKFSVKLSAS LSPVIPGFPQIVNSNPLTEAFRVNWLSGTYFEVVTTGMEQLDFET GPNIFDLQIYVKDEVGVTDLQVLTVQVTDVNEPP*GGTKHHHHHH |
| FLAG-CDHR3 EC1-His W76A SEQ ID NO: 21 (SEQ ID NO: 22 = ital.: aa 20-130 of SEQ ID NO: 1 with W76A mutation) | MASDYKDDDDK *LHLILL PATGNVAENSPPGTSVHKFSVKLSAS LSPVIPGFPQIVNSNPLTEAFRVNALSGTYFEVVTTGMEQLDFET GPNIFDLQIYVKDEVGVTDLQVLTVQVTDVNEPP*GGTKHHHHHH (W76A = bold/underline) |
| FLAG-CDHR3 E1-2-His SEQ ID NO: 5 (SEQ ID NO: 23: ital = aa from SEQ ID NO: 1) | MASDYKDDDDK *LHLILL PATGNVAENSPPGTSVHKFSVKLSAS LSPVIPGFPQIVNSNPLTEAFRVNWLSGTYFEVVTTG MEQLDFETGPNIFDLQIYVKDEVGVTDLQVLTVQVTDVNE* PPQF QGNLAEGL HLYIVERANPGFIYQVEAFDPEDTSRNI *PLSYFLISPPKSFRMSANGTLFSTTELDFEAGHRSFHLIVEVRDSG GLKASTELQVNIVNLNDEVPRFT*GGTKHHHHHH |
| FLAG-CDHR3 EC1-3-His SEQ ID NO: 6 (SEQ ID NO: 24: ital = aa from SEQ ID NO: 1 with a C to a mutation at position 345) | MASDYKDDDDK *LHLILL PATGNVAENSPPGTSVHKFSVKLSAS LSPVIPGFPQIVNSNPLTEAFRVNWLSGTYFEVVTTG MEQLDFETGPNIFDLQIYVKDEVGVTDLQVLTVQVTDVNE* PPQF QGNLAEGL HLYIVERANPGFIYQVEAFDPEDTSRNI *PLSYFLISPPKSFRMSANGTLFSTTELDFEAGHRSFHLIVEVRDSG GLKASTELQVNIVNLND* EVPRFTSPTR V *YTVLEE LSPGTIVANITAEDPDDEGFPSHLLYSITTVSKYFMINQLTGTIQV AQRIDRDAGELRQNPTISLEVLVKDRPYGGQENR IQITFIVEDVNDN* PATA GTKHHHHHH |
| FLAG-CDHR3 W76A EC1-2-His SEQ ID NO: 7 (SEQ ID NO: 25: ital = aa from SEQ ID NO: 1) | MASDYKDDDDK *LHLILL PATGNVAENSPPGTSVHKFSVKLSAS LSPVIPGFPQIVNSNPLTEAFRVN* A *LSGTYFEVVTTG MEQLDFETGPNIFDLQIYVKDEVGVTDLQVLTVQVTDVNE* PPQF QGNLAEGL HLYIVERANPGFIYQVEAFDPEDTSRNI *PLSYFLISPPKSFRMSANGTLFSTTELDFEAGHRSFHLIVEVRDSG GLKASTELQVNIVNLNDEVPRFT*GGTKHHHHHH |
| FLAG-CDHR3 W76A EC1-3-His SEQ ID NO: 8 (SEQ ID NO: 26: ital = aa from SEQ ID NO: 1 with a C to a mutation at position 345) | MASDYKDDDDK *LHLILL PATGNVAENSPPGTSVHKFSVKLSAS LSPVIPGFPQIVNSNPLTEAFRVN* A *LSGTYFEVVTTG MEQLDFETGPNIFDLQIYVKDEVGVTDLQVLTVQVTDVNE* PPQF QGNLAEGL HLYIVERANPGFIYQVEAFDPEDTSRNI *PLSYFLISPPKSFRMSANGTLFSTTELDFEAGHRSFHLIVEVRDSG GLKASTELQVNIVNLND* EVPRFTSPTR V *YTVLEE LSPGTIVANITAEDPDDEGFPSHLLYSITTVSKYFMINQLTGTIQV AQRIDRDAGELRQNPTISLEVLVKDRPYGGQENR IQITFIVEDVNDN* PATA GTKHHHHHH |
| FLAG-CDHR3 EC1+3(Δ2) SEQID NO: 9 (SEQID NO: 27: ital = aa from SEQ ID NO: 1 with a C to a mutation at position 345) | MASDYKDDDDK *LHLILL PATGNVAENSPPGTSVHKFSVKLSAS LSPVIPGFPQIVNSNPLTEAFRVNWLSGTYFEVVTTG MEQLDFETGPNIFDLQIYVKDEVGVTDLQVLTVQVTDVNE* EVPR FTSPTR V *YTVLEELSPGTIVANITAEDPDDEGFPSH LLYSITTVSKYFMINQLTGTIQVAQRIDRDGELRQNPTISLEVLV KDRPYGGQENRIQITFIVEDVNDN* PATA GTKHHHHHH |

*The tag sequences denoted below are not necessary for the binding and inhibitory activity of the proteins. The tags are tools for the ability to purify the proteins, and other suitable tags/methodology may be used. The present disclosure contemplated peptides and proteins with and without tags.
Bold at beginning and end of sequences: non-CDHR3 cloning tags
Bolded H-start of Domain 2;
Bolded V-start of Domain 3
underline: linker sequences (Linker 1: LHLILL SEQ ID NO:15); Linker 2:PPWFQGNLAEGL (SEQ ID NO:16); Linker3:EVPRFTSPTR (SEQ ID NO:17), Linker4: PATX (SEQ ID NO:18) wherein X is an amino acid selected from A, G, V, L, I, S, or T, preferably PATA (SEQ ID NO:32)
italic—sequences from SEQ ID NO:1

Domain 1 with a W76A mutation: (SEQ ID NO: 30)
PATGNVAENSPPGTSVHKFSVKLSASLSPVIPGFPQI-
VNSNPLTEAFRVN<u>A</u>LSGTYFEVVTTGM EQLD-
FETGPNIFDLQIYV<span style="text-decoration:overline">K</span>DEVGVTDLQVLTVQVTDVNE Domain 1 with a W76X mutation: (SEQ ID NO: 31) wherein X is an amino acid selected from A, G, V, L, I, S, or T, preferably A
PATGNVAENSPPGTSVHKFSVKLSASLSPVIPGFPQI-
VNSNPLTEAFRVN<u>X</u>LSGTYFEVVTTGM EQLD-
FETGPNIFDLQIYV<span style="text-decoration:overline">K</span>DEVGVTDLQVLTVQVTDVNE Domain 1+Linker 1 (SEQ ID NO:33)
<u>LHLILL</u>PATGNVAENSPPGTSVHKFSVKLSASLSPVIP
GFPQIVNSNPLTEAFRVNWLSGTYFEV VTTGMEQLD-
FETGPNIFDLQIYVKDEVGVTDLQVLTVQVTDVNE Domain 1 W76X+Linker 1 (SEQ ID NO:34)
<u>LHLILL</u>PATGNVAENSPPGTSVHKFSVKLSASLSPVIP
GFPQIVNSNPLTEAFRVN<u>X</u>LSGTYFEV VTTGMEQLD-
FETGPNIFDLQIYVKDEVGVTDLQVLTVQVTDVNE

---

The invention claimed is:

1. A soluble truncated CDHR3 peptide consisting of:
   (a) SEQ ID NO:2,
   (b) SEQ ID NO:31, wherein X of SEQ ID NO: 31 is selected from the group consisting of A, G, V, L, I, S, and T and wherein X correlates to residue W76 of full-length CDHR3 (SEQ ID NO: 1),
   (c) a polypeptide having at least 90% identity to SEQ ID NO: 2,
   (d) a polypeptide having at least 90% identity to SEQ ID NO: 31, wherein X of SEQ ID NO: 31 is selected from the group consisting of A, G, V, L, I, S, and T, or
   (e) any one of the polypeptides of (a)-(d) further comprising a linker peptide of SEQ ID NO: 15, SEQ ID NO: 16 or both.

2. The soluble truncated CDHR3 peptide of claim 1, wherein the peptide further comprises at least one linker, wherein the at least one linker is SEQ ID NO:15 attached to the N-terminus of the CDHR3 peptide, SEQ ID NO:16 attached to the C-terminus of the CDHR3 peptide, or both.

3. The soluble truncated CDHR3 peptide of claim 1, wherein the soluble truncated CDHR3 peptide further comprises amino acids encoding a heterologous tag.

4. The soluble truncated CDHR3 peptide of claim 1, wherein X is alanine.

5. The soluble truncated CDHR3 peptide of claim 1, wherein the soluble truncated CDHR3 peptide is covalently or non-covalently linked to a heterologous tag.

6. The soluble truncated CDHR3 peptide of claim 5, wherein the tag is a FLAG tag or a HIS tag.

7. A therapeutic composition for reducing or preventing rhinovirus C entry into cells, the composition comprising any one of the soluble truncated CDHR3 peptides of claim 1 and Ca++ in a pharmaceutically acceptable carrier.

8. A vector comprising the nucleic acids encoding the soluble truncated CDHR3 peptide of claim 1.

9. A cell comprising the vector of claim 8.

10. The cell of claim 9, wherein the cell is a bacterial cell.

11. A method of making the soluble truncated recombinant peptide of CDHR3, the method comprising:
    (a) transforming bacterial cells with the vector of claim 8;
    (b) inducing recombinant protein expression in the bacterial cells;
    (c) lysing bacterial cells and collecting by centrifugation the inclusion bodies comprising the soluble truncated peptide;
    (d) solubilizing the protein within the inclusion body; and
    (e) dialyzing and refolding the protein in buffer supplemented with Ca++ to produce soluble truncated recombinant peptides of CDHR3.

12. The method of claim 11, wherein the buffer of (e) is a pharmaceutically acceptable buffer supplemented with about 1-10 mM $CaCl_2$.

13. A method for reducing the infection by human rhinovirus C (HRV-C) of a host cell susceptible to infection by HRV-C, comprising: contacting the HRV-C with the soluble truncated CDHR3 peptide of claim 1 in an amount effective to reduce the infectivity of the HRV-C.

14. The method of claim 13, wherein the method is performed in vivo.

15. An in vitro assay for testing an agent for anti-viral activity against rhinovirus C, the assay comprising the steps of:
    (a) contacting the agent with the soluble truncated CDHR3 peptide of claim 1 and rhinovirus C; and
    (b) assaying the ability of the agent to disrupt binding of the soluble truncated CDHR3 peptide of claim 1 to rhinovirus C.

16. The assay of claim 15, wherein the assay further comprises:
    (c) incubating the rhinovirus C pre-incubated with the soluble truncated CDHR3 peptide of claim 1 and the agent or with the agent alone with host cells, and measuring the infectivity of the rhinovirus C in the host cell and utilizing the soluble truncated CDHR3 peptide as a positive contra.

17. The assay of claim 16, wherein the soluble truncated CDHR3 peptide of claim 1 is attached to a solid support.

18. The assay of claim 17, wherein the solid support is a tissue culture dish or plate.

* * * * *

SEQUENCE LISTING

```
<160> NUMBER OF SEQ ID NOS: 35

<210> SEQ ID NO 1
<211> LENGTH: 885
<212> TYPE: PRT
<213> ORGANISM: Artificial Sequence
<220> FEATURE:
<223> OTHER INFORMATION: CDHR3

<400> SEQUENCE: 1

Met Gln Glu Ala Ile Ile Leu Leu Ala Leu Leu Gly Ala Met Ser Gly
1               5                   10                  15

Gly Glu Ala Leu His Leu Ile Leu Leu Pro Ala Thr Gly Asn Val Ala
            20                  25                  30

Glu Asn Ser Pro Pro Gly Thr Ser Val His Lys Phe Ser Val Lys Leu
        35                  40                  45

Ser Ala Ser Leu Ser Pro Val Ile Pro Gly Phe Pro Gln Ile Val Asn
    50                  55                  60

Ser Asn Pro Leu Thr Glu Ala Phe Arg Val Asn Trp Leu Ser Gly Thr
65                  70                  75                  80

Tyr Phe Glu Val Val Thr Thr Gly Met Glu Gln Leu Asp Phe Glu Thr
                85                  90                  95

Gly Pro Asn Ile Phe Asp Leu Gln Ile Tyr Val Lys Asp Glu Val Gly
            100                 105                 110

Val Thr Asp Leu Gln Val Leu Thr Val Gln Val Thr Asp Val Asn Glu
        115                 120                 125

Pro Pro Gln Phe Gln Gly Asn Leu Ala Glu Gly Leu His Leu Tyr Ile
    130                 135                 140

Val Glu Arg Ala Asn Pro Gly Phe Ile Tyr Gln Val Glu Ala Phe Asp
145                 150                 155                 160

Pro Glu Asp Thr Ser Arg Asn Ile Pro Leu Ser Tyr Phe Leu Ile Ser
                165                 170                 175

Pro Pro Lys Ser Phe Arg Met Ser Ala Asn Gly Thr Leu Phe Ser Thr
            180                 185                 190

Thr Glu Leu Asp Phe Glu Ala Gly His Arg Ser Phe His Leu Ile Val
        195                 200                 205

Glu Val Arg Asp Ser Gly Gly Leu Lys Ala Ser Thr Glu Leu Gln Val
    210                 215                 220

Asn Ile Val Asn Leu Asn Asp Glu Val Pro Arg Phe Thr Ser Pro Thr
225                 230                 235                 240

Arg Val Tyr Thr Val Leu Glu Glu Leu Ser Pro Gly Thr Ile Val Ala
                245                 250                 255

Asn Ile Thr Ala Glu Asp Pro Asp Asp Glu Gly Phe Pro Ser His Leu
            260                 265                 270

Leu Tyr Ser Ile Thr Thr Val Ser Lys Tyr Phe Met Ile Asn Gln Leu
        275                 280                 285
```

-continued

```
Thr Gly Thr Ile Gln Val Ala Gln Arg Ile Asp Arg Asp Ala Gly Glu
    290                 295                 300
Leu Arg Gln Asn Pro Thr Ile Ser Leu Glu Val Leu Val Lys Asp Arg
305                 310                 315                 320
Pro Tyr Gly Gly Gln Glu Asn Arg Ile Gln Ile Thr Phe Ile Val Glu
                325                 330                 335
Asp Val Asn Asp Asn Pro Ala Thr Cys Gln Lys Phe Thr Phe Ser Ile
            340                 345                 350
Met Val Pro Glu Arg Thr Ala Lys Gly Thr Leu Leu Leu Asp Leu Asn
        355                 360                 365
Lys Phe Cys Phe Asp Asp Ser Glu Ala Pro Asn Asn Arg Phe Asn
370                 375                 380
Phe Thr Met Pro Ser Gly Val Gly Ser Gly Ser Arg Phe Leu Gln Asp
385                 390                 395                 400
Pro Ala Gly Ser Gly Lys Ile Val Leu Ile Gly Asp Leu Asp Tyr Glu
                405                 410                 415
Asn Pro Ser Asn Leu Ala Ala Gly Asn Lys Tyr Thr Val Ile Ile Gln
            420                 425                 430
Val Gln Asp Val Ala Pro Pro Tyr Tyr Lys Asn Asn Val Tyr Val Tyr
        435                 440                 445
Ile Leu Thr Ser Pro Glu Asn Glu Phe Pro Leu Ile Phe Asp Arg Pro
    450                 455                 460
Ser Tyr Val Phe Asp Val Ser Glu Arg Arg Pro Ala Arg Thr Arg Val
465                 470                 475                 480
Gly Gln Val Arg Ala Thr Asp Lys Asp Leu Pro Gln Ser Ser Leu Leu
                485                 490                 495
Tyr Ser Ile Ser Thr Gly Gly Ala Ser Leu Gln Tyr Pro Asn Val Phe
            500                 505                 510
Trp Ile Asn Pro Lys Thr Gly Glu Leu Gln Leu Val Thr Lys Val Asp
        515                 520                 525
Cys Glu Thr Thr Pro Ile Tyr Ile Leu Arg Ile Gln Ala Thr Asn Asn
    530                 535                 540
Glu Asp Thr Ser Ser Val Thr Val Thr Val Asn Ile Leu Glu Glu Asn
545                 550                 555                 560
Asp Glu Lys Pro Ile Cys Thr Pro Asn Ser Tyr Phe Leu Ala Leu Pro
                565                 570                 575
Val Asp Leu Lys Val Gly Thr Asn Ile Gln Asn Phe Lys Leu Thr Cys
            580                 585                 590
Thr Asp Leu Asp Ser Ser Pro Arg Ser Phe Arg Tyr Ser Ile Gly Pro
        595                 600                 605
Gly Asn Val Asn Asn His Phe Thr Phe Ser Pro Asn Ala Gly Ser Asn
    610                 615                 620
Val Thr Arg Leu Leu Leu Thr Ser Arg Phe Asp Tyr Ala Gly Gly Phe
625                 630                 635                 640
Asp Lys Ile Trp Asp Tyr Lys Leu Leu Val Tyr Val Thr Asp Asp Asn
                645                 650                 655
Leu Met Ser Asp Arg Lys Lys Ala Glu Ala Leu Val Glu Thr Gly Thr
            660                 665                 670
Val Thr Leu Ser Ile Lys Val Ile Pro His Pro Thr Thr Ile Ile Thr
        675                 680                 685
Thr Thr Pro Arg Pro Arg Val Thr Tyr Gln Val Leu Arg Lys Asn Val
    690                 695                 700
Tyr Ser Pro Ser Ala Trp Tyr Val Pro Phe Val Ile Thr Leu Gly Ser
```

```
                705                 710                 715                 720
        Ile Leu Leu Leu Gly Leu Leu Val Tyr Leu Val Val Leu Leu Ala Lys
                        725                 730                 735

Ala Ile His Arg His Cys Pro Cys Lys Thr Gly Lys Asn Lys Glu Pro
                        740                 745                 750

Leu Thr Lys Lys Gly Glu Thr Lys Thr Ala Glu Arg Asp Val Val Val
                        755                 760                 765

Glu Thr Ile Gln Met Asn Thr Ile Phe Asp Gly Glu Ala Ile Asp Pro
                        770                 775                 780

Val Thr Gly Glu Thr Tyr Glu Phe Asn Ser Lys Thr Gly Ala Arg Lys
        785                 790                 795                 800

Trp Lys Asp Pro Leu Thr Gln Met Pro Lys Trp Lys Glu Ser Ser His
                        805                 810                 815

Gln Gly Ala Ala Pro Arg Arg Val Thr Ala Glu Gly Met Gly Ser
                        820                 825                 830

Leu Arg Ser Ala Asn Trp Glu Glu Asp Glu Leu Ser Gly Lys Ala Trp
                        835                 840                 845

Ala Glu Asp Ala Gly Leu Gly Ser Arg Asn Glu Gly Gly Lys Leu Gly
                        850                 855                 860

Asn Pro Lys Asn Arg Asn Pro Ala Phe Met Asn Arg Ala Tyr Pro Lys
        865                 870                 875                 880

Pro His Pro Gly Lys
                        885

<210> SEQ ID NO 2
<211> LENGTH: 103
<212> TYPE: PRT
<213> ORGANISM: Artificial Sequence
<220> FEATURE:
<223> OTHER INFORMATION: CDHR3 Domain 1

<400> SEQUENCE: 2

Pro Ala Thr Gly Asn Val Ala Glu Asn Ser Pro Gly Thr Ser Val
1               5                   10                  15

His Lys Phe Ser Val Lys Leu Ser Ala Ser Leu Ser Pro Val Ile Pro
                20                  25                  30

Gly Phe Pro Gln Ile Val Asn Ser Asn Pro Leu Thr Glu Ala Phe Arg
            35                  40                  45

Val Asn Trp Leu Ser Gly Thr Tyr Phe Glu Val Thr Thr Gly Met
    50                  55                  60

Glu Gln Leu Asp Phe Glu Thr Gly Pro Asn Ile Phe Asp Leu Gln Ile
65                  70                  75                  80

Tyr Val Lys Asp Glu Val Gly Val Thr Asp Leu Gln Val Leu Thr Val
                85                  90                  95

Gln Val Thr Asp Val Asn Glu
                100

<210> SEQ ID NO 3
<211> LENGTH: 91
<212> TYPE: PRT
<213> ORGANISM: Artificial Sequence
<220> FEATURE:
<223> OTHER INFORMATION: CDHR3 Domain 2

<400> SEQUENCE: 3

His Leu Tyr Ile Val Glu Arg Ala Asn Pro Gly Phe Ile Tyr Gln Val
1               5                   10                  15
```

```
Glu Ala Phe Asp Pro Glu Asp Thr Ser Arg Asn Ile Pro Leu Ser Tyr
            20                  25                  30

Phe Leu Ile Ser Pro Pro Lys Ser Phe Arg Met Ser Ala Asn Gly Thr
        35                  40                  45

Leu Phe Ser Thr Thr Glu Leu Asp Phe Glu Ala Gly His Arg Ser Phe
    50                  55                  60

His Leu Ile Val Glu Val Arg Asp Ser Gly Gly Leu Lys Ala Ser Thr
65                  70                  75                  80

Glu Leu Gln Val Asn Ile Val Asn Leu Asn Asp
                85                  90

<210> SEQ ID NO 4
<211> LENGTH: 100
<212> TYPE: PRT
<213> ORGANISM: Artificial Sequence
<220> FEATURE:
<223> OTHER INFORMATION: CDHR3 Domain 3

<400> SEQUENCE: 4

Val Tyr Thr Val Leu Glu Glu Leu Ser Pro Gly Thr Ile Val Ala Asn
1               5                   10                  15

Ile Thr Ala Glu Asp Pro Asp Glu Gly Phe Pro Ser His Leu Leu
            20                  25                  30

Tyr Ser Ile Thr Thr Val Ser Lys Tyr Phe Met Ile Asn Gln Leu Thr
        35                  40                  45

Gly Thr Ile Gln Val Ala Gln Arg Ile Asp Arg Asp Ala Gly Glu Leu
    50                  55                  60

Arg Gln Asn Pro Thr Ile Ser Leu Glu Val Val Lys Asp Arg Pro
65                  70                  75                  80

Tyr Gly Gly Gln Glu Asn Arg Ile Gln Ile Thr Phe Ile Val Glu Asp
                85                  90                  95

Val Asn Asp Asn
            100

<210> SEQ ID NO 5
<211> LENGTH: 239
<212> TYPE: PRT
<213> ORGANISM: Artificial Sequence
<220> FEATURE:
<223> OTHER INFORMATION: FLAG-CDHR3 EC1-2-His

<400> SEQUENCE: 5

Met Ala Ser Asp Tyr Lys Asp Asp Asp Lys Leu His Leu Ile Leu
1               5                   10                  15

Leu Pro Ala Thr Gly Asn Val Ala Glu Asn Ser Pro Pro Gly Thr Ser
            20                  25                  30

Val His Lys Phe Ser Val Lys Leu Ser Ala Ser Leu Ser Pro Val Ile
        35                  40                  45

Pro Gly Phe Pro Gln Ile Val Asn Ser Asn Pro Leu Thr Glu Ala Phe
    50                  55                  60

Arg Val Asn Trp Leu Ser Gly Thr Tyr Phe Glu Val Thr Thr Gly
65                  70                  75                  80

Met Glu Gln Leu Asp Phe Glu Thr Gly Pro Asn Ile Phe Asp Leu Gln
                85                  90                  95

Ile Tyr Val Lys Asp Glu Val Gly Val Thr Asp Leu Gln Val Leu Thr
                100                 105                 110

Val Gln Val Thr Asp Val Asn Glu Pro Pro Gln Phe Gln Gly Asn Leu
            115                 120                 125
```

```
Ala Glu Gly Leu His Leu Tyr Ile Val Glu Arg Ala Asn Pro Gly Phe
            130                 135                 140

Ile Tyr Gln Val Glu Ala Phe Asp Pro Glu Asp Thr Ser Arg Asn Ile
145                 150                 155                 160

Pro Leu Ser Tyr Phe Leu Ile Ser Pro Lys Ser Phe Arg Met Ser
                165                 170                 175

Ala Asn Gly Thr Leu Phe Ser Thr Thr Glu Leu Asp Phe Glu Ala Gly
            180                 185                 190

His Arg Ser Phe His Leu Ile Val Glu Val Arg Asp Ser Gly Gly Leu
            195                 200                 205

Lys Ala Ser Thr Glu Leu Gln Val Asn Ile Val Asn Leu Asn Asp Glu
            210                 215                 220

Val Pro Arg Phe Thr Gly Gly Thr Lys His His His His His
225                 230                 235

<210> SEQ ID NO 6
<211> LENGTH: 346
<212> TYPE: PRT
<213> ORGANISM: Artificial Sequence
<220> FEATURE:
<223> OTHER INFORMATION: FLAG-CDHR3 EC1-3-His

<400> SEQUENCE: 6

Met Ala Ser Asp Tyr Lys Asp Asp Asp Lys Leu His Leu Ile Leu
1               5                   10                  15

Leu Pro Ala Thr Gly Asn Val Ala Glu Asn Ser Pro Gly Thr Ser
                20                  25                  30

Val His Lys Phe Ser Val Lys Leu Ser Ala Ser Leu Ser Pro Val Ile
            35                  40                  45

Pro Gly Phe Pro Gln Ile Val Asn Ser Asn Pro Leu Thr Glu Ala Phe
50                  55                  60

Arg Val Asn Trp Leu Ser Gly Thr Tyr Phe Glu Val Val Thr Thr Gly
65                  70                  75                  80

Met Glu Gln Leu Asp Phe Glu Thr Gly Pro Asn Ile Phe Asp Leu Gln
                85                  90                  95

Ile Tyr Val Lys Asp Glu Val Gly Val Thr Asp Leu Gln Val Leu Thr
            100                 105                 110

Val Gln Val Thr Asp Val Asn Glu Pro Pro Gln Phe Gln Gly Asn Leu
            115                 120                 125

Ala Glu Gly Leu His Leu Tyr Ile Val Glu Arg Ala Asn Pro Gly Phe
            130                 135                 140

Ile Tyr Gln Val Glu Ala Phe Asp Pro Glu Asp Thr Ser Arg Asn Ile
145                 150                 155                 160

Pro Leu Ser Tyr Phe Leu Ile Ser Pro Lys Ser Phe Arg Met Ser
                165                 170                 175

Ala Asn Gly Thr Leu Phe Ser Thr Thr Glu Leu Asp Phe Glu Ala Gly
            180                 185                 190

His Arg Ser Phe His Leu Ile Val Glu Val Arg Asp Ser Gly Gly Leu
            195                 200                 205

Lys Ala Ser Thr Glu Leu Gln Val Asn Ile Val Asn Leu Asn Asp Glu
            210                 215                 220

Val Pro Arg Phe Thr Ser Pro Thr Arg Val Tyr Thr Val Leu Glu Glu
225                 230                 235                 240

Leu Ser Pro Gly Thr Ile Val Ala Asn Ile Thr Ala Glu Asp Pro Asp
                245                 250                 255
```

```
Asp Glu Gly Phe Pro Ser His Leu Leu Tyr Ser Ile Thr Thr Val Ser
                260                 265                 270

Lys Tyr Phe Met Ile Asn Gln Leu Thr Gly Thr Ile Gln Val Ala Gln
            275                 280                 285

Arg Ile Asp Arg Asp Ala Gly Glu Leu Arg Gln Asn Pro Thr Ile Ser
        290                 295                 300

Leu Glu Val Leu Val Lys Asp Arg Pro Tyr Gly Gly Gln Glu Asn Arg
305                 310                 315                 320

Ile Gln Ile Thr Phe Ile Val Glu Asp Val Asn Asp Asn Pro Ala Thr
                325                 330                 335

Ala Gly Thr Lys His His His His His His
            340                 345

<210> SEQ ID NO 7
<211> LENGTH: 239
<212> TYPE: PRT
<213> ORGANISM: Artificial Sequence
<220> FEATURE:
<223> OTHER INFORMATION: FLAG-CDHR3 EC1-2-His W76A

<400> SEQUENCE: 7

Met Ala Ser Asp Tyr Lys Asp Asp Asp Lys Leu His Leu Ile Leu
1               5                   10                  15

Leu Pro Ala Thr Gly Asn Val Ala Glu Asn Ser Pro Pro Gly Thr Ser
            20                  25                  30

Val His Lys Phe Ser Val Lys Leu Ser Ala Ser Leu Ser Pro Val Ile
        35                  40                  45

Pro Gly Phe Pro Gln Ile Val Asn Ser Asn Pro Leu Thr Glu Ala Phe
    50                  55                  60

Arg Val Asn Ala Leu Ser Gly Thr Tyr Phe Glu Val Val Thr Thr Gly
65                  70                  75                  80

Met Glu Gln Leu Asp Phe Glu Thr Gly Pro Asn Ile Phe Asp Leu Gln
                85                  90                  95

Ile Tyr Val Lys Asp Glu Val Gly Val Thr Asp Leu Gln Val Leu Thr
            100                 105                 110

Val Gln Val Thr Asp Val Asn Glu Pro Pro Gln Phe Gln Gly Asn Leu
        115                 120                 125

Ala Glu Gly Leu His Leu Tyr Ile Val Glu Arg Ala Asn Pro Gly Phe
    130                 135                 140

Ile Tyr Gln Val Glu Ala Phe Asp Pro Glu Asp Thr Ser Arg Asn Ile
145                 150                 155                 160

Pro Leu Ser Tyr Phe Leu Ile Ser Pro Pro Lys Ser Phe Arg Met Ser
                165                 170                 175

Ala Asn Gly Thr Leu Phe Ser Thr Thr Glu Leu Asp Phe Glu Ala Gly
            180                 185                 190

His Arg Ser Phe His Leu Ile Val Glu Val Arg Asp Ser Gly Gly Leu
        195                 200                 205

Lys Ala Ser Thr Glu Leu Gln Val Asn Ile Val Asn Leu Asn Asp Glu
    210                 215                 220

Val Pro Arg Phe Thr Gly Gly Thr Lys His His His His His His
225                 230                 235

<210> SEQ ID NO 8
<211> LENGTH: 346
<212> TYPE: PRT
<213> ORGANISM: Artificial Sequence
```

<220> FEATURE:
<223> OTHER INFORMATION: FLAG-CDHR3 EC1-3-His W76A

<400> SEQUENCE: 8

Met Ala Ser Asp Tyr Lys Asp Asp Asp Lys Leu His Leu Ile Leu
1               5                   10                  15

Leu Pro Ala Thr Gly Asn Val Ala Glu Asn Ser Pro Gly Thr Ser
            20                  25                  30

Val His Lys Phe Ser Val Lys Leu Ser Ala Ser Leu Ser Pro Val Ile
            35                  40                  45

Pro Gly Phe Pro Gln Ile Val Asn Ser Asn Pro Leu Thr Glu Ala Phe
50                      55                  60

Arg Val Asn Ala Leu Ser Gly Thr Tyr Phe Glu Val Val Thr Thr Gly
65                  70                  75                  80

Met Glu Gln Leu Asp Phe Glu Thr Gly Pro Asn Ile Phe Asp Leu Gln
                85                  90                  95

Ile Tyr Val Lys Asp Glu Val Gly Val Thr Asp Leu Gln Val Leu Thr
            100                 105                 110

Val Gln Val Thr Asp Val Asn Glu Pro Pro Gln Phe Gln Gly Asn Leu
        115                 120                 125

Ala Glu Gly Leu His Leu Tyr Ile Val Glu Arg Ala Asn Pro Gly Phe
    130                 135                 140

Ile Tyr Gln Val Glu Ala Phe Asp Pro Glu Asp Thr Ser Arg Asn Ile
145                 150                 155                 160

Pro Leu Ser Tyr Phe Leu Ile Ser Pro Pro Lys Ser Phe Arg Met Ser
                165                 170                 175

Ala Asn Gly Thr Leu Phe Ser Thr Thr Glu Leu Asp Phe Glu Ala Gly
            180                 185                 190

His Arg Ser Phe His Leu Ile Val Glu Val Arg Asp Ser Gly Gly Leu
        195                 200                 205

Lys Ala Ser Thr Glu Leu Gln Val Asn Ile Val Asn Leu Asn Asp Glu
    210                 215                 220

Val Pro Arg Phe Thr Ser Pro Thr Arg Val Tyr Thr Val Leu Glu Glu
225                 230                 235                 240

Leu Ser Pro Gly Thr Ile Val Ala Asn Ile Thr Ala Glu Asp Pro Asp
                245                 250                 255

Asp Glu Gly Phe Pro Ser His Leu Leu Tyr Ser Ile Thr Thr Val Ser
            260                 265                 270

Lys Tyr Phe Met Ile Asn Gln Leu Thr Gly Thr Ile Gln Val Ala Gln
        275                 280                 285

Arg Ile Asp Arg Asp Ala Gly Glu Leu Arg Gln Asn Pro Thr Ile Ser
290                 295                 300

Leu Glu Val Leu Val Lys Asp Arg Pro Tyr Gly Gly Gln Glu Asn Arg
305                 310                 315                 320

Ile Gln Ile Thr Phe Ile Val Glu Asp Val Asn Asp Asn Pro Ala Thr
                325                 330                 335

Ala Gly Thr Lys His His His His His His
            340                 345

<210> SEQ ID NO 9
<211> LENGTH: 243
<212> TYPE: PRT
<213> ORGANISM: Artificial Sequence
<220> FEATURE:
<223> OTHER INFORMATION: FLAG-CDHR3 EC1+3(delta2)

<400> SEQUENCE: 9

```
Met Ala Ser Asp Tyr Lys Asp Asp Asp Lys Leu His Leu Ile Leu
1               5                   10                  15

Leu Pro Ala Thr Gly Asn Val Ala Glu Asn Ser Pro Pro Gly Thr Ser
            20                  25                  30

Val His Lys Phe Ser Val Lys Leu Ser Ala Ser Leu Ser Pro Val Ile
            35                  40                  45

Pro Gly Phe Pro Gln Ile Val Asn Ser Asn Pro Leu Thr Glu Ala Phe
        50                  55                  60

Arg Val Asn Trp Leu Ser Gly Thr Tyr Phe Glu Val Thr Thr Gly
65                  70                  75                  80

Met Glu Gln Leu Asp Phe Glu Thr Gly Pro Asn Ile Phe Asp Leu Gln
                85                  90                  95

Ile Tyr Val Lys Asp Glu Val Gly Val Thr Asp Leu Gln Val Leu Thr
            100                 105                 110

Val Gln Val Thr Asp Val Asn Glu Glu Val Pro Arg Phe Thr Ser Pro
        115                 120                 125

Thr Arg Val Tyr Thr Val Leu Glu Glu Leu Ser Pro Gly Thr Ile Val
    130                 135                 140

Ala Asn Ile Thr Ala Glu Asp Pro Asp Asp Glu Gly Phe Pro Ser His
145                 150                 155                 160

Leu Leu Tyr Ser Ile Thr Thr Val Ser Lys Tyr Phe Met Ile Asn Gln
                165                 170                 175

Leu Thr Gly Thr Ile Gln Val Ala Gln Arg Ile Asp Arg Asp Ala Gly
            180                 185                 190

Glu Leu Arg Gln Asn Pro Thr Ile Ser Leu Glu Val Leu Val Lys Asp
        195                 200                 205

Arg Pro Tyr Gly Gly Gln Glu Asn Arg Ile Gln Ile Thr Phe Ile Val
    210                 215                 220

Glu Asp Val Asn Asp Asn Pro Ala Thr Ala Gly Thr Lys His His His
225                 230                 235                 240

His His His
```

<210> SEQ ID NO 10
<211> LENGTH: 654
<212> TYPE: DNA
<213> ORGANISM: Artificial Sequence
<220> FEATURE:
<223> OTHER INFORMATION: CDHR3 EC1-2

<400> SEQUENCE: 10

```
ctacacctaa tcctcttacc tgctacaggc aatgtggcag agaattctcc acctgggact    60
tcagtgcaca gtttctctgt gaagttatca gcatcattgt cacctgtgat cccaggattt   120
ccccagatag tcaactcaaa tcccctcact gaagctttta gggtgaattg gctgtcaggc   180
acctactttg aggttgtcac cactgggatg aacaactag attttgaaac aggaccaaac   240
atatttgatt tgcagattta tgtgaaggat gaggttggtg tcacagacct tcaagtcctg   300
actgtccagg taacagatgt gaacgagcca cctcagtttc aaggcaactt ggcagaaggt   360
ctacacctct acatagtaga aagagcaaac cctggattca tttaccaggt tgaggccttc   420
gatccagaag acacaagccg aaacattccc ctcagttatt tcctgatttc tccccaaag   480 agcttcagaa tgtctgctaa tggcacccte ttctccacaa cagaattgga ctttgaagca   540
ggacacagaa gtttccatct catcgtggag gtgagggaca gtggaggcct caaagcctcc   600
```
acagagctcc aggtgaacat cgtgaacctc aacgacgaag tccctcgctt tacc    654

<210> SEQ ID NO 11
<211> LENGTH: 654
<212> TYPE: DNA
<213> ORGANISM: Artificial Sequence
<220> FEATURE:
<223> OTHER INFORMATION: CDHR3 EC1-2 W76A

<400> SEQUENCE: 11
ctacacctaa tcctcttacc tgctacaggc aatgtggcag agaattctcc acctgggact    60
tcagtgcaca gttttctgt gaagttatca gcatcattgt cacctgtgat cccaggattt    120
ccccagatag tcaactcaaa tcccctcact gaagctttta gggtgaatgc gctgtcaggc    180
acctactttg aggttgtcac cactgggatg aacaactag attttgaaac aggaccaaac    240
atatttgatt tgcagattta tgtgaaggat gaggttggtg tcacagacct tcaagtcctg    300
actgtccagg taacagatgt gaacgagcca cctcagtttc aaggcaactt ggcagaaggt    360
ctacacctct acatagtaga aagagcaaac cctggattca tttaccaggt tgaggccttc    420
gatccagaag acacaagccg aaacattccc ctcagttatt tcctgatttc tcccccaaag    480
agcttcagaa tgtctgctaa tggcacccte ttctccacaa cagaattgga ctttgaagca    540
ggacacagaa gtttccatct catcgtggag gtgagggaca gtggaggcct caaagcctcc    600
acagagctcc aggtgaacat cgtgaacctc aacgacgaag tccctcgctt tacc    654

<210> SEQ ID NO 12
<211> LENGTH: 978
<212> TYPE: DNA
<213> ORGANISM: Artificial Sequence
<220> FEATURE:
<223> OTHER INFORMATION: CDHR3 EC1-3

<400> SEQUENCE: 12
ctacacctaa tcctcttacc tgctacaggc aatgtggcag agaattctcc acctgggact    60
tcagtgcaca gttttctgt gaagttatca gcatcattgt cacctgtgat cccaggattt    120
ccccagatag tcaactcaaa tcccctcact gaagctttta gggtgaattg gctgtcaggc    180
acctactttg aggttgtcac cactgggatg aacaactag attttgaaac aggaccaaac    240
atatttgatt tgcagattta tgtgaaggat gaggttggtg tcacagacct tcaagtcctg    300
actgtccagg taacagatgt gaacgagcca cctcagtttc aaggcaactt ggcagaaggt    360
ctacacctct acatagtaga aagagcaaac cctggattca tttaccaggt tgaggccttc    420
gatccagaag acacaagccg aaacattccc ctcagttatt tcctgatttc tcccccaaag    480
agcttcagaa tgtctgctaa tggcacccte ttctccacaa cagaattgga ctttgaagca    540
ggacacagaa gtttccatct catcgtggag gtgagggaca gtggaggcct caaagcctcc    600
acagagctcc aggtgaacat cgtgaacctc aacgacgaag tccctcgctt taccagcccg    660
acacgagtgt acacagtcct ggaggaactg agtccaggaa ccatcgtggc caatatcaca    720
gcggaggatc ctgatgatga aggttttccc agccacctcc tctacagcat taccactgtt    780
agcaaatatt tcatgataaa tcagttgact ggtacaatcc aagtggccca aaggatagac    840
cgagatgcag gtgaattgag acaaaatccc accatttccc tggaagttct agtgaaggac    900
agaccatatg ggggtcagga gaatcgcatc cagataacct tcattgtgga agacgtcaac    960
gacaatcctg ccacagcc    978

<210> SEQ ID NO 13
<211> LENGTH: 978
<212> TYPE: DNA
<213> ORGANISM: Artificial Sequence
<220> FEATURE:
<223> OTHER INFORMATION: CDHR3 EC1-3 W76A

<400> SEQUENCE: 13

```
ctacacctaa tcctcttacc tgctacaggc aatgtggcag agaattctcc acctgggact      60
tcagtgcaca gttttctgt gaagttatca gcatcattgt cacctgtgat cccaggattt     120
ccccagatag tcaactcaaa tcccctcact gaagctttta gggtgaatgc gctgtcaggc    180
acctactttg aggttgtcac cactgggatg aacaactag attttgaaac aggaccaaac    240
atatttgatt tgcagattta tgtgaaggat gaggttggtg tcacagacct tcaagtcctg    300
actgtccagg taacagatgt gaacgagcca cctcagtttc aaggcaactt ggcagaaggt    360
ctacacctct acatagtaga aagagcaaac cctggattca tttaccaggt tgaggccttc    420
gatccagaag acacaagccg aaacattccc ctcagttatt tcctgatttc tcccccaaag    480
agcttcagaa tgtctgctaa tggcaccctc ttctccacaa cagaattgga ctttgaagca    540
ggacacagaa gtttccatct catcgtggag gtgagggaca gtggaggcct caaagcctcc    600
acagagctcc aggtgaacat cgtgaacctc aacgacgaag tccctcgctt taccagcccg    660
acacgagtgt acacagtcct ggaggaactg agtccaggaa ccatcgtggc caatatcaca    720
gcggaggatc ctgatgatga aggttttccc agccacctcc tctacagcat taccactgtt    780
agcaaatatt tcatgataaa tcagttgact ggtacaatcc aagtggccca aaggatagac    840
cgagatgcag gtgaattgag acaaaatccc accatttccc tggaagttct agtgaaggac    900
agaccatatg ggggtcagga gaatcgcatc cagataacct tcattgtgga agacgtcaac    960
gacaatcctg ccacagcc                                                   978
```

<210> SEQ ID NO 14
<211> LENGTH: 669
<212> TYPE: DNA
<213> ORGANISM: Artificial Sequence
<220> FEATURE:
<223> OTHER INFORMATION: CDHR3 EC1+3(delta2)

<400> SEQUENCE: 14

```
ctacacctaa tcctcttacc tgctacaggc aatgtggcag agaattctcc acctgggact      60
tcagtgcaca gttttctgt gaagttatca gcatcattgt cacctgtgat cccaggattt     120
ccccagatag tcaactcaaa tcccctcact gaagctttta gggtgaattg gctgtcaggc    180
acctactttg aggttgtcac cactgggatg aacaactag attttgaaac aggaccaaac    240
atatttgatt tgcagattta tgtgaaggat gaggttggtg tcacagacct tcaagtcctg    300
actgtccagg taacagatgt gaacgaggaa gtccctcgct ttaccagccc gacacgagtg    360
tacacagtcc tggaggaact gagtccagga accatcgtgg ccaatatcac agcggaggat    420
cctgatgatg aaggttttcc cagccacctc ctctacagca ttaccactgt tagcaaatat    480
ttcatgataa atcagttgac tggtacaatc caagtggccc aaaggataga ccgagatgca    540
ggtgaattga gacaaaatcc caccatttcc ctggaagttc tagtgaagga cagaccatat    600
gggggtcagg agaatcgcat ccagataacc ttcattgtgg aagacgtcaa cgacaatcct    660
gccacagcc                                                             669
```

<210> SEQ ID NO 15

```
<211> LENGTH: 5
<212> TYPE: PRT
<213> ORGANISM: Artificial Sequence
<220> FEATURE:
<223> OTHER INFORMATION: CDHR3 Linker 1 (aa 21-25 of SEQ ID NO:1)

<400> SEQUENCE: 15

His Leu Ile Leu Leu
1               5

<210> SEQ ID NO 16
<211> LENGTH: 12
<212> TYPE: PRT
<213> ORGANISM: Artificial Sequence
<220> FEATURE:
<223> OTHER INFORMATION: CDHR3 Linker 2  (aa 129-140 of SEQ ID NO:1)

<400> SEQUENCE: 16

Pro Pro Gln Phe Gln Gly Asn Leu Ala Glu Gly Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: CDHR3 Linker 3  (aa 232-241 of SEQ ID NO:1)

<400> SEQUENCE: 17

Glu Val Pro Arg Phe Thr Ser Pro Thr Arg
1               5                   10

<210> SEQ ID NO 18
<211> LENGTH: 4
<212> TYPE: PRT
<213> ORGANISM: Artificial Sequence
<220> FEATURE:
<223> OTHER INFORMATION: CDHR3 Linker 4 with variable residue
<220> FEATURE:
<221> NAME/KEY: X
<222> LOCATION: (4)..(4)
<223> OTHER INFORMATION: X is A, G, V, L, I, S, or T

<400> SEQUENCE: 18

Pro Ala Thr Xaa
1

<210> SEQ ID NO 19
<211> LENGTH: 132
<212> TYPE: PRT
<213> ORGANISM: Artificial Sequence
<220> FEATURE:
<223> OTHER INFORMATION: FLAG-CDHR3 EC1-His

<400> SEQUENCE: 19

Met Ala Ser Asp Tyr Lys Asp Asp Asp Lys Leu His Leu Ile Leu
1               5                   10                  15

Leu Pro Ala Thr Gly Asn Val Ala Glu Asn Ser Pro Gly Thr Ser
                20                  25                  30

Val His Lys Phe Ser Val Lys Leu Ser Ala Ser Leu Ser Pro Val Ile
                35                  40                  45

Pro Gly Phe Pro Gln Ile Val Asn Ser Asn Pro Leu Thr Glu Ala Phe
    50                  55                  60

Arg Val Asn Trp Leu Ser Gly Thr Tyr Phe Glu Val Val Thr Thr Gly
65                  70                  75                  80
```

```
Met Glu Gln Leu Asp Phe Glu Thr Gly Pro Asn Ile Phe Asp Leu Gln
            85                  90                  95

Ile Tyr Val Lys Asp Glu Val Gly Val Thr Asp Leu Gln Val Leu Thr
            100                 105                 110

Val Gln Val Thr Asp Val Asn Glu Pro Pro Gly Gly Thr Lys His His
            115                 120                 125

His His His His
        130

<210> SEQ ID NO 20
<211> LENGTH: 111
<212> TYPE: PRT
<213> ORGANISM: Artificial Sequence
<220> FEATURE:
<223> OTHER INFORMATION: CDHR3 EC1

<400> SEQUENCE: 20

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Trp Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu Pro Pro
            100                 105                 110

<210> SEQ ID NO 21
<211> LENGTH: 132
<212> TYPE: PRT
<213> ORGANISM: Artificial Sequence
<220> FEATURE:
<223> OTHER INFORMATION: FLAG-CDHR3 EC1-His W76A

<400> SEQUENCE: 21

Met Ala Ser Asp Tyr Lys Asp Asp Asp Lys Leu His Leu Ile Leu Leu
1               5                   10                  15

Leu Pro Ala Thr Gly Asn Val Ala Glu Asn Ser Pro Pro Gly Thr Ser
            20                  25                  30

Val His Lys Phe Ser Val Lys Leu Ser Ala Ser Leu Ser Pro Val Ile
            35                  40                  45

Pro Gly Phe Pro Gln Ile Val Asn Ser Asn Pro Leu Thr Glu Ala Phe
        50                  55                  60

Arg Val Asn Ala Leu Ser Gly Thr Tyr Phe Glu Val Val Thr Thr Gly
65                  70                  75                  80

Met Glu Gln Leu Asp Phe Glu Thr Gly Pro Asn Ile Phe Asp Leu Gln
            85                  90                  95

Ile Tyr Val Lys Asp Glu Val Gly Val Thr Asp Leu Gln Val Leu Thr
            100                 105                 110

Val Gln Val Thr Asp Val Asn Glu Pro Pro Gly Gly Thr Lys His His
            115                 120                 125

His His His His
        130
```

```
<210> SEQ ID NO 22
<211> LENGTH: 111
<212> TYPE: PRT
<213> ORGANISM: Artificial Sequence
<220> FEATURE:
<223> OTHER INFORMATION: CDHR3 EC1 W76A

<400> SEQUENCE: 22
```

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Ala Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu Pro Pro
            100                 105                 110

```
<210> SEQ ID NO 23
<211> LENGTH: 218
<212> TYPE: PRT
<213> ORGANISM: Artificial Sequence
<220> FEATURE:
<223> OTHER INFORMATION: CDHR3 EC1-2

<400> SEQUENCE: 23
```

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Trp Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu Pro Pro Gln
            100                 105                 110

Phe Gln Gly Asn Leu Ala Glu Gly Leu His Leu Tyr Ile Val Glu Arg
        115                 120                 125

Ala Asn Pro Gly Phe Ile Tyr Gln Val Glu Ala Phe Asp Pro Glu Asp
    130                 135                 140

Thr Ser Arg Asn Ile Pro Leu Ser Tyr Phe Leu Ile Ser Pro Pro Lys
145                 150                 155                 160

Ser Phe Arg Met Ser Ala Asn Gly Thr Leu Phe Ser Thr Thr Glu Leu
                165                 170                 175

Asp Phe Glu Ala Gly His Arg Ser Phe His Leu Ile Val Glu Val Arg
            180                 185                 190

Asp Ser Gly Gly Leu Lys Ala Ser Thr Glu Leu Gln Val Asn Ile Val

```
              195                 200                 205
Asn Leu Asn Asp Glu Val Pro Arg Phe Thr
    210                 215
```

<210> SEQ ID NO 24
<211> LENGTH: 326
<212> TYPE: PRT
<213> ORGANISM: Artificial Sequence
<220> FEATURE:
<223> OTHER INFORMATION: CDHR3 EC1-3 C345A

<400> SEQUENCE: 24

```
Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Trp Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu Pro Pro Gln
            100                 105                 110

Phe Gln Gly Asn Leu Ala Glu Gly Leu His Leu Tyr Ile Val Glu Arg
        115                 120                 125

Ala Asn Pro Gly Phe Ile Tyr Gln Val Glu Ala Phe Asp Pro Glu Asp
    130                 135                 140

Thr Ser Arg Asn Ile Pro Leu Ser Tyr Phe Leu Ile Ser Pro Pro Lys
145                 150                 155                 160

Ser Phe Arg Met Ser Ala Asn Gly Thr Leu Phe Ser Thr Thr Glu Leu
                165                 170                 175

Asp Phe Glu Ala Gly His Arg Ser Phe His Leu Ile Val Glu Val Arg
            180                 185                 190

Asp Ser Gly Gly Leu Lys Ala Ser Thr Glu Leu Gln Val Asn Ile Val
        195                 200                 205

Asn Leu Asn Asp Glu Val Pro Arg Phe Thr Ser Pro Thr Arg Val Tyr
    210                 215                 220

Thr Val Leu Glu Glu Leu Ser Pro Gly Thr Ile Val Ala Asn Ile Thr
225                 230                 235                 240

Ala Glu Asp Pro Asp Asp Glu Gly Phe Pro Ser His Leu Leu Tyr Ser
                245                 250                 255

Ile Thr Thr Val Ser Lys Tyr Phe Met Ile Asn Gln Leu Thr Gly Thr
            260                 265                 270

Ile Gln Val Ala Gln Arg Ile Asp Arg Asp Ala Gly Glu Leu Arg Gln
        275                 280                 285

Asn Pro Thr Ile Ser Leu Glu Val Leu Val Lys Asp Arg Pro Tyr Gly
    290                 295                 300

Gly Gln Glu Asn Arg Ile Gln Ile Thr Phe Ile Val Glu Asp Val Asn
305                 310                 315                 320

Asp Asn Pro Ala Thr Ala
                325
```

```
<210> SEQ ID NO 25
<211> LENGTH: 219
<212> TYPE: PRT
<213> ORGANISM: Artificial Sequence
<220> FEATURE:
<223> OTHER INFORMATION: CDHR3 EC1-2 W76A

<400> SEQUENCE: 25

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Ala Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu Pro Pro Gln
            100                 105                 110

Phe Gln Gly Asn Leu Ala Glu Gly Leu His Leu Tyr Ile Val Glu Arg
        115                 120                 125

Ala Asn Pro Gly Phe Ile Tyr Gln Val Glu Ala Phe Asp Pro Glu Asp
    130                 135                 140

Thr Ser Arg Asn Ile Pro Leu Ser Tyr Phe Leu Ile Ser Pro Pro Lys
145                 150                 155                 160

Ser Phe Arg Met Ser Ala Asn Gly Thr Leu Phe Ser Thr Thr Glu Leu
                165                 170                 175

Asp Phe Glu Ala Gly His Arg Ser Phe His Leu Ile Val Glu Val Arg
            180                 185                 190

Asp Ser Gly Gly Leu Lys Ala Ser Thr Glu Leu Gln Val Asn Ile Val
        195                 200                 205

Asn Leu Asn Asp Glu Val Pro Arg Phe Thr Gly
    210                 215

<210> SEQ ID NO 26
<211> LENGTH: 326
<212> TYPE: PRT
<213> ORGANISM: Artificial Sequence
<220> FEATURE:
<223> OTHER INFORMATION: CDHR3 EC1-3 C345A + W76A

<400> SEQUENCE: 26

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Ala Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95
```

```
Leu Gln Val Leu Thr Val Gln Val Thr Asp Val Asn Glu Pro Pro Gln
                100                 105                 110

Phe Gln Gly Asn Leu Ala Glu Gly Leu His Leu Tyr Ile Val Glu Arg
            115                 120                 125

Ala Asn Pro Gly Phe Ile Tyr Gln Val Glu Ala Phe Asp Pro Glu Asp
        130                 135                 140

Thr Ser Arg Asn Ile Pro Leu Ser Tyr Phe Leu Ile Ser Pro Pro Lys
145                 150                 155                 160

Ser Phe Arg Met Ser Ala Asn Gly Thr Leu Phe Ser Thr Thr Glu Leu
                165                 170                 175

Asp Phe Glu Ala Gly His Arg Ser Phe His Leu Ile Val Glu Val Arg
            180                 185                 190

Asp Ser Gly Gly Leu Lys Ala Ser Thr Glu Leu Gln Val Asn Ile Val
        195                 200                 205

Asn Leu Asn Asp Glu Val Pro Arg Phe Thr Ser Pro Thr Arg Val Tyr
210                 215                 220

Thr Val Leu Glu Glu Leu Ser Pro Gly Thr Ile Val Ala Asn Ile Thr
225                 230                 235                 240

Ala Glu Asp Pro Asp Asp Glu Gly Phe Pro Ser His Leu Leu Tyr Ser
                245                 250                 255

Ile Thr Thr Val Ser Lys Tyr Phe Met Ile Asn Gln Leu Thr Gly Thr
            260                 265                 270

Ile Gln Val Ala Gln Arg Ile Asp Arg Asp Ala Gly Glu Leu Arg Gln
        275                 280                 285

Asn Pro Thr Ile Ser Leu Glu Val Leu Val Lys Asp Arg Pro Tyr Gly
290                 295                 300

Gly Gln Glu Asn Arg Ile Gln Ile Thr Phe Ile Val Glu Asp Val Asn
305                 310                 315                 320

Asp Asn Pro Ala Thr Ala
                325

<210> SEQ ID NO 27
<211> LENGTH: 223
<212> TYPE: PRT
<213> ORGANISM: Artificial Sequence
<220> FEATURE:
<223> OTHER INFORMATION: CDHR3 EC1+3(delta2) C345A

<400> SEQUENCE: 27

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
                20                  25                  30

Leu Ser Pro Val Ile Pro Gly Phe Pro Gln Ile Val Asn Ser Asn Pro
            35                  40                  45

Leu Thr Glu Ala Phe Arg Val Asn Trp Leu Ser Gly Thr Tyr Phe Glu
        50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu Glu Val Pro
            100                 105                 110

Arg Phe Thr Ser Pro Thr Arg Val Tyr Thr Val Leu Glu Glu Leu Ser
        115                 120                 125
```

```
Pro Gly Thr Ile Val Ala Asn Ile Thr Ala Glu Asp Pro Asp Asp Glu
    130                 135                 140

Gly Phe Pro Ser His Leu Leu Tyr Ser Ile Thr Thr Val Ser Lys Tyr
145                 150                 155                 160

Phe Met Ile Asn Gln Leu Thr Gly Thr Ile Gln Val Ala Gln Arg Ile
                165                 170                 175

Asp Arg Asp Ala Gly Glu Leu Arg Gln Asn Pro Thr Ile Ser Leu Glu
            180                 185                 190

Val Leu Val Lys Asp Arg Pro Tyr Gly Gly Gln Glu Asn Arg Ile Gln
        195                 200                 205

Ile Thr Phe Ile Val Glu Asp Val Asn Asp Asn Pro Ala Thr Ala
    210                 215                 220

<210> SEQ ID NO 28
<211> LENGTH: 333
<212> TYPE: DNA
<213> ORGANISM: Artificial Sequence
<220> FEATURE:
<223> OTHER INFORMATION: CDHR3 EC1

<400> SEQUENCE: 28
ctacacctaa tcctcttacc tgctacaggc aatgtggcag agaattctcc acctgggact    60
tcagtgcaca gtttctgt gaagttatca gcatcattgt cacctgtgat cccaggattt    120
ccccagatag tcaactcaaa tcccctcact gaagctttta gggtgaattg gctgtcaggc    180
acctactttg aggttgtcac cactgggatg gaacaactag attttgaaac aggaccaaac    240
atatttgatt tgcagattta tgtgaaggat gaggttggtg tcacagacct tcaagtcctg    300
actgtccagg taacagatgt gaacgagcca cct                                 333

<210> SEQ ID NO 29
<211> LENGTH: 333
<212> TYPE: DNA
<213> ORGANISM: Artificial Sequence
<220> FEATURE:
<223> OTHER INFORMATION: CDHR3 EC1 W76A

<400> SEQUENCE: 29
ctacacctaa tcctcttacc tgctacaggc aatgtggcag agaattctcc acctgggact    60
tcagtgcaca gtttctgt gaagttatca gcatcattgt cacctgtgat cccaggattt    120
ccccagatag tcaactcaaa tcccctcact gaagctttta gggtgaatgc gctgtcaggc    180
acctactttg aggttgtcac cactgggatg gaacaactag attttgaaac aggaccaaac    240
atatttgatt tgcagattta tgtgaaggat gaggttggtg tcacagacct tcaagtcctg    300
actgtccagg taacagatgt gaacgagcca cct                                 333

<210> SEQ ID NO 30
<211> LENGTH: 103
<212> TYPE: PRT
<213> ORGANISM: Artificial Sequence
<220> FEATURE:
<223> OTHER INFORMATION: CDHR3 Domain 1 W76A

<400> SEQUENCE: 30

Pro Ala Thr Gly Asn Val Ala Glu Asn Ser Pro Gly Thr Ser Val
1               5                   10                  15

His Lys Phe Ser Val Lys Leu Ser Ala Ser Leu Ser Pro Val Ile Pro
            20                  25                  30

Gly Phe Pro Gln Ile Val Asn Ser Asn Pro Leu Thr Glu Ala Phe Arg
```

```
                35                  40                  45
Val Asn Ala Leu Ser Gly Thr Tyr Phe Glu Val Val Thr Thr Gly Met
         50                  55                  60

Glu Gln Leu Asp Phe Glu Thr Gly Pro Asn Ile Phe Asp Leu Gln Ile
 65                  70                  75                  80

Tyr Val Lys Asp Glu Val Gly Val Thr Asp Leu Gln Val Leu Thr Val
                 85                  90                  95

Gln Val Thr Asp Val Asn Glu
            100

<210> SEQ ID NO 31
<211> LENGTH: 103
<212> TYPE: PRT
<213> ORGANISM: Artificial Sequence
<220> FEATURE:
<223> OTHER INFORMATION: CDHR3 Domain 1 W76X
<220> FEATURE:
<221> NAME/KEY: X
<222> LOCATION: (51)..(51)
<223> OTHER INFORMATION: X is A, G, V, L, I, S, or T
<220> FEATURE:
<221> NAME/KEY: X
<222> LOCATION: (51)..(51)
<223> OTHER INFORMATION: X is A, G, V, L, I, S, or T

<400> SEQUENCE: 31

Pro Ala Thr Gly Asn Val Ala Glu Asn Ser Pro Pro Gly Thr Ser Val
 1               5                  10                  15

His Lys Phe Ser Val Lys Leu Ser Ala Ser Leu Ser Pro Val Ile Pro
                 20                  25                  30

Gly Phe Pro Gln Ile Val Asn Ser Asn Pro Leu Thr Glu Ala Phe Arg
             35                  40                  45

Val Asn Xaa Leu Ser Gly Thr Tyr Phe Glu Val Val Thr Thr Gly Met
         50                  55                  60

Glu Gln Leu Asp Phe Glu Thr Gly Pro Asn Ile Phe Asp Leu Gln Ile
 65                  70                  75                  80

Tyr Val Lys Asp Glu Val Gly Val Thr Asp Leu Gln Val Leu Thr Val
                 85                  90                  95

Gln Val Thr Asp Val Asn Glu
            100

<210> SEQ ID NO 32
<211> LENGTH: 4
<212> TYPE: PRT
<213> ORGANISM: Artificial Sequence
<220> FEATURE:
<223> OTHER INFORMATION: CDHR3 Linker 4

<400> SEQUENCE: 32

Pro Ala Thr Ala
 1

<210> SEQ ID NO 33
<211> LENGTH: 109
<212> TYPE: PRT
<213> ORGANISM: Artificial Sequence
<220> FEATURE:
<223> OTHER INFORMATION: CDHR3 Domain 1 + Linker 1

<400> SEQUENCE: 33

Leu His Leu Ile Leu Leu Pro Ala Thr Gly Asn Val Ala Glu Asn Ser
 1               5                  10                  15
```

```
Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Trp Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu
            100                 105

<210> SEQ ID NO 34
<211> LENGTH: 109
<212> TYPE: PRT
<213> ORGANISM: Artificial Sequence
<220> FEATURE:
<223> OTHER INFORMATION: CDHR3 Domain 1 + Linker 1 W76X
<220> FEATURE:
<221> NAME/KEY: X
<222> LOCATION: (57)..(57)
<223> OTHER INFORMATION: X is A, G, V, L, I, S, or T

<400> SEQUENCE: 34

Leu His Leu Ile Leu Leu Pro Ala Thr Gly Asn Val Ala Glu Asn Ser
1               5                   10                  15

Pro Pro Gly Thr Ser Val His Lys Phe Ser Val Lys Leu Ser Ala Ser
            20                  25                  30

Leu Ser Pro Val Ile Pro Gly Phe Pro Gln Ile Val Asn Ser Asn Pro
        35                  40                  45

Leu Thr Glu Ala Phe Arg Val Asn Xaa Leu Ser Gly Thr Tyr Phe Glu
    50                  55                  60

Val Val Thr Thr Gly Met Glu Gln Leu Asp Phe Glu Thr Gly Pro Asn
65                  70                  75                  80

Ile Phe Asp Leu Gln Ile Tyr Val Lys Asp Glu Val Gly Val Thr Asp
                85                  90                  95

Leu Gln Val Leu Thr Val Gln Val Thr Asp Val Asn Glu
            100                 105

<210> SEQ ID NO 35
<211> LENGTH: 8
<212> TYPE: PRT
<213> ORGANISM: Artificial Sequence
<220> FEATURE:
<223> OTHER INFORMATION: Synthetic- Flag-tag

<400> SEQUENCE: 35

Asp Tyr Lys Asp Asp Asp Asp Lys
1               5
```

UNITED STATES PATENT AND TRADEMARK OFFICE
CERTIFICATE OF CORRECTION

PATENT NO. : 11,667,690 B2
APPLICATION NO. : 17/058934
DATED : June 6, 2023
INVENTOR(S) : Ann Carol Palmenberg et al.

It is certified that error appears in the above-identified patent and that said Letters Patent is hereby corrected as shown below:

In the Specification

Column 4, Line 18, "a-CD HR3" should be --α-CDHR3--.

Column 5, Line 29, "5200" should be --S200--.

Column 5, Line 31, "5200" should be --S200--.

Column 23, Line 31, "5200" should be --S200--.

Column 26, Line 51, "[2]" should be --[23]--.

Column 26, Line 65, "5200" should be --S200--.

Column 27, Line 54, "pCDHR3-FLAG-0529" should be --pCDHR3-FLAG-C529--.

Column 30, Line 4, "ng" should be --µg--.

Column 30, Line 8, "SD S/PAGE" should be --SDS/PAGE--.

Column 31, Line 47, "Glade" should be --clade--.

Column 35, Line 6, "serrpartry" should be --serrpartrv--.

Column 35, Line 9, "vgtniqnfld" should be --vgtniqnfkl--.

In the Claims

Column 76, Claim 16, Line 27, "contra" should be --control--.

Signed and Sealed this
Seventeenth Day of October, 2023

Katherine Kelly Vidal
*Director of the United States Patent and Trademark Office*